(12) United States Patent
McDonald et al.

(10) Patent No.: US 8,778,925 B2
(45) Date of Patent: Jul. 15, 2014

(54) PYRIDINE AND PYRIMIDINE BASED COMPOUNDS AS WNT SIGNALING PATHWAY INHIBITORS FOR THE TREATMENT OF CANCER

(75) Inventors: Edward McDonald, Sutton (GB); Julian Blagg, Sutton (GB); Mark Pichowicz, Sutton (GB); Simon Ross Crumpler, Sutton (GB)

(73) Assignee: Cancer Research Technology Ltd., London (GB)

( * ) Notice: Subject to any disclaimer, the term of this patent is extended or adjusted under 35 U.S.C. 154(b) by 299 days.

(21) Appl. No.: 13/122,555

(22) PCT Filed: Oct. 6, 2009

(86) PCT No.: PCT/GB2009/051319
§ 371 (c)(1),
(2), (4) Date: Apr. 4, 2011

(87) PCT Pub. No.: WO2010/041054
PCT Pub. Date: Apr. 15, 2010

(65) Prior Publication Data
US 2011/0190297 A1    Aug. 4, 2011

(30) Foreign Application Priority Data
Oct. 6, 2008    (GB) .................................. 0818241.2

(51) Int. Cl.
| | | |
|---|---|---|
| *A01N 43/00* | (2006.01) | |
| *A61K 31/00* | (2006.01) | |
| *A61K 31/55* | (2006.01) | |
| *A01N 43/42* | (2006.01) | |
| *A61K 31/44* | (2006.01) | |
| *A01N 43/38* | (2006.01) | |
| *A61K 31/40* | (2006.01) | |
| *C07D 225/04* | (2006.01) | |
| *C07D 223/14* | (2006.01) | |
| *C07D 487/00* | (2006.01) | |
| *C07D 491/00* | (2006.01) | |
| *C07D 513/00* | (2006.01) | |
| *C07D 215/00* | (2006.01) | |
| *C07D 217/00* | (2006.01) | |
| *C07D 219/00* | (2006.01) | |
| *C07D 221/00* | (2006.01) | |
| *C07D 209/96* | (2006.01) | |
| *C07D 495/00* | (2006.01) | |

(52) U.S. Cl.
USPC ............... 514/210.2; 514/212.02; 514/278; 514/409; 540/466; 540/543; 546/16; 548/409

(58) Field of Classification Search
USPC ............ 514/210.19, 212.02, 278, 409, 210.2; 540/466, 543; 546/16; 548/409
See application file for complete search history.

(56) References Cited

U.S. PATENT DOCUMENTS

| | | | |
|---|---|---|---|
| 2002/0107290 A1* | 8/2002 | Nakagawa et al. | ........... 514/619 |
| 2005/0277654 A1 | 12/2005 | Maynard et al. | |
| 2007/0129345 A1 | 6/2007 | Zhuo et al. | |

FOREIGN PATENT DOCUMENTS

| | | |
|---|---|---|
| CA | 2 431 171 | 6/2002 |
| WO | WO 97/06802 | 2/1997 |
| WO | WO 98/06705 | 2/1998 |
| WO | WO 98/35956 | 8/1998 |
| WO | WO 99/64392 | 12/1999 |
| WO | WO 01/27107 | 4/2001 |
| WO | WO 2004/083235 | 9/2004 |
| WO | WO 2005/044192 | 5/2005 |
| WO | WO 2005/068468 | 7/2005 |
| WO | WO 2005/095350 | 10/2005 |
| WO | WO 2006/053024 | 5/2006 |
| WO | WO 2007/008146 | 1/2007 |
| WO | WO 2007/092435 | 8/2007 |
| WO | WO 2007/123269 | 11/2007 |
| WO | WO 2007/135427 | 11/2007 |

OTHER PUBLICATIONS

Fukui et. al., Antimicrobial Agents and Chemotherapy, 2008, American Society for Microbiology, vol. 52, issue 7, pp. 2420-2427.*
Patidar et. al., International Journal of Pharma Research and Development, May 2005, vol. 2, issue 3, pp. 1-12.*
CAS STN registry record, publ. Sep. 14, 1999.*
Triazenes, http://ru.wikipedia.or/wiki, possibly published Apr. 4, 2012 but publication date unclear, with translation.
Barker et al., "Mining the Wnt pathway for cancer therapeutics," Nature Reviews Drug Discovery, (Dec. 2006), vol. 5, p. 997.
Park C. H. et al., Biochem. Biophys. Res. Commun., (Mar. 4, 2005), vol. 328, No. 1, pp. 227-234.

* cited by examiner

*Primary Examiner* — Sarah Pihonak
(74) *Attorney, Agent, or Firm* — The Marbury Law Group, PLLC

(57) ABSTRACT

The present invention relates to pyridine and pyrimidine based compounds, pharmaceutical compositions comprising these compounds and their potential use as therapeutic agents for the treatment and/or prevention of cancer.

11 Claims, No Drawings

PYRIDINE AND PYRIMIDINE BASED COMPOUNDS AS WNT SIGNALING PATHWAY INHIBITORS FOR THE TREATMENT OF CANCER

FIELD OF THE INVENTION

This invention relates to compounds and their use in therapy, in particular in the treatment, prevention or delay of progression of cancer.

BACKGROUND TO THE INVENTION

Oncogenic deregulation of the Wnt signalling pathway is a causal factor in the initiation of cancer in a diverse range of tissues including the colon, breast and liver (see, for example, Barker et al, "Mining the Wnt pathway for cancer therapeutics", Nature Reviews Drug Discovery, December 2006 Vol. 5, 997). There remains a need for effective anti-cancer agents, in particular inhibitors of the Wnt signalling pathway.

WO 01/27107 discloses heterocyclic sodium/proton exchange inhibitors which are useful in the treatment of cardiovascular disorders. Included are pyrimidine compounds which are substituted by an imidazolylpiperidinyl group.

SUMMARY OF THE INVENTION

According to the present invention, there is provided a compound of the formula (I):

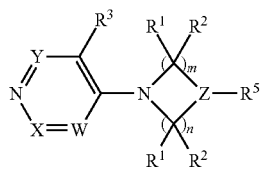

wherein
W, X and Y are each independently CH, C($R^4$) or N;
Z is C($R^6$) or N;
$R^1$ and $R^2$ are each independently hydrogen or $C_{1-6}$ alkyl; or $R^1$ and $R^2$ taken together with the carbon atom to which they are attached may form a 5- or 6-membered carbocycle or heterocycle, either of which is optionally substituted with 1, 2, 3, 4 or 5 $R^a$;
$R^3$ and $R^4$ are each independently halo or a group selected from $C_{1-6}$ alkyl, $C_{1-6}$ alkoxy, carbocyclyl and heterocyclyl, any of which is optionally substituted with 1, 2, 3, 4 or 5 $R^a$;
when Z is N, $R^5$ is $R^7$, —C(O)$R^7$, —C(O)O$R^7$—, —S(O)$_l R^7$, —C(O)N($R^7$)$R^8$, —C(S)N($R^7$)$R^8$—, —S(O)$_l$N($R^7$)$R^8$ or heterocyclyl optionally substituted with 1, 2, 3, 4 or 5 $R^a$;
when Z is C($R^6$), $R^5$ is H, CN, C(O)OH, —C(O)$R^7$, —C(O)O$R^7$—, —S(O)$_l R^7$, —N($R^6$)$R^7$, —C(O)N($R^7$)$R^8$, —C(S)N($R^7$)$R^8$—, —S(O)$_l$N($R^7$)$R^8$, —N($R^7$)C(O)$R^8$, —N($R^7$)S(O)$_l R^8$ or an $C_{1-6}$ alkyl or heterocyclyl group which is optionally substituted with 1, 2, 3, 4 or 5 $R^a$;
$R^6$ is hydrogen, $C_{1-6}$ alkyl, $C_{1-6}$ alkoxy, —OH, $R^5$, (CH$_2$)$_m R^5$ or —N($R^7$)$R^8$;
or $R^5$ and $R^6$ taken together with the carbon atom to which they are attached may form a 5- or 6-membered heterocycle which is optionally substituted with 1, 2, 3, 4 or 5 $R^a$;

$R^7$ and $R^8$ are each independently hydrogen or a group selected from $C_{1-6}$ alkyl optionally containing 1, 2 or 3 heteroatoms selected from N, O and S, carbocyclyl and heterocyclyl, any of which is optionally substituted with 1, 2, 3, 4 or 5 $R^a$;
or $R^7$ and $R^8$ may be linked so that, together with the atoms to which they are attached, they form a 5- or 6-membered heterocycle which is optionally substituted with 1, 2, 3, 4 or 5 $R^a$;
each $R^a$ is independently selected from halogen, trifluoromethyl, cyano, oxo, nitro, —O$R^b$, —C(O)$R^b$, —C(O)O$R^b$, —OC(O)$R^b$, —S(O)$_l R^b$, —N($R^b$)$R^c$, —N($R^b$)C(O)$R^c$, —C(O)N($R^b$)$R^c$, —S(O)$_l$N($R^b$)$R^c$ and $R^d$;
$R^b$ and $R^c$ are each independently hydrogen or $R^d$;
$R^d$ is selected from hydrocarbyl (e.g. $C_{1-6}$alkyl), carbocyclyl, carbocyclyl-$C_{1-6}$alkyl, and heterocyclyl, each of which is optionally substituted with 1, 2, 3, 4 or 5 substituents independently selected from halogen, cyano, amino, hydroxy, $C_{1-6}$ alkyl, $C_{1-6}$ alkoxy;
l is 0, 1 or 2; and
m and n are each independently 1, 2 or 3;
or a pharmaceutically acceptable salt, N-oxide or prodrug thereof.

In a further aspect, the present invention provides a compound of the formula (I):

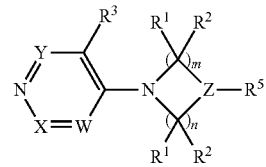

wherein
W, X and Y are each independently =CH—, =C($R^4$)— or =N—;
Z is C($R^6$) or N;
$R^1$ and $R^2$ are each independently hydrogen or $C_{1-6}$ alkyl; or $R^1$ and $R^2$ taken together with the carbon atom to which they are attached may form a 5- or 6-membered carbocycle or heterocycle, either of which is optionally substituted with 1, 2, 3, 4 or 5 $R^a$;
$R^3$ and $R^4$ are each independently halo or a group selected from $C_{1-6}$ alkyl, $C_{1-6}$ alkoxy, carbocyclyl and heterocyclyl, any of which is optionally substituted with 1, 2, 3, 4 or 5 $R^a$;
when Z is N, $R^5$ is $R^7$, —C(O)$R^7$, —S(O)$_l R^7$, —C(O)N($R^7$)$R^8$, —S(O)$_l$N($R^7$)$R^8$ or heterocyclyl optionally substituted with 1, 2, 3, 4 or 5 $R^a$;
when Z is C($R^6$), $R^5$ is H, —CN, C(O)OH, —C(O)$R^7$, —S(O)$_l R^7$, —N($R^6$)$R^7$, —C(O)N($R^7$)$R^8$, —S(O)$_l$N($R^7$)$R^8$, —N($R^7$)C(O)$R^8$, —N($R^7$)S(O)$_l R^8$ or heterocyclyl optionally substituted with 1, 2, 3, 4 or 5 $R^a$;
$R^6$ is hydrogen, $C_{1-6}$ alkyl, $C_{1-6}$ alkoxy, —OH, $R^5$ or —(CH$_2$)$_m R^5$;
or $R^5$ and $R^6$ taken together with the carbon atom to which they are attached may form a 5- or 6-membered heterocycle which is optionally substituted with 1, 2, 3, 4 or 5 $R^a$;
$R^7$ and $R^8$ are each independently hydrogen or a group selected from $C_{1-6}$ alkyl optionally containing 1, 2 or 3 heteroatoms selected from N, O and S, carbocyclyl and heterocyclyl, any of which is optionally substituted with 1, 2, 3, 4 or 5 $R^a$;

each $R^a$ is independently selected from halogen, trifluoromethyl, cyano, oxo, nitro, —$OR^b$, —$C(O)R^b$, —$C(O)OR^b$, —$OC(O)R^b$, —$S(O)_lR^b$, —$N(R^b)R^c$, —$N(R^b)C(O)R^c$, —$C(O)N(R^b)R^c$, —$S(O)_lN(R^b)R^c$ and $R^d$;

$R^b$ and $R^c$ are each independently hydrogen or $R^d$;

$R^d$ is selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;

l is 0, 1 or 2; and m and n are each independently 1, 2 or 3;

or a pharmaceutically acceptable salt, N-oxide or prodrug thereof; for use in the treatment, prevention or delay of progression of cancer.

The invention also provides a pharmaceutical formulation comprising a compound of formula (I), or a pharmaceutically acceptable salt thereof, and a pharmaceutically acceptable carrier or excipient.

In a further aspect, the invention relates to the use of a compound of formula (I), or a pharmaceutically acceptable salt thereof, for the manufacture of a medicament for the treatment, prevention or delay of progression of cancer. A method of treating, preventing or delaying progression of cancer is also provided, which involves administering a therapeutically effective amount of a compound of the invention to a subject.

Compounds of the invention can exist in different forms, such as free acids, free bases, esters, N-oxides and other prodrugs, salts and tautomers, for example, and the disclosure includes all variant forms of the compounds.

Features, integers, characteristics, compounds, chemical moieties or groups described in conjunction with a particular aspect, embodiment or example of the invention are to be understood to be applicable to any other aspect, embodiment or example described herein unless incompatible therewith.

DESCRIPTION OF VARIOUS EMBODIMENTS

Definitions

Hydrocarbyl

The term "hydrocarbyl" as used herein includes reference to moieties consisting exclusively of hydrogen and carbon atoms; such a moiety may comprise an aliphatic and/or an aromatic moiety. The moiety may, for example, comprise 1, 2, 3, 4, 5, 6, 7, 8, 9, 10, 11 or 12 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g cyclopropylmethyl); cycloalkyl (e.g. cyclopropyl, cyclobutyl, cyclopentyl or cyclohexyl); alkenyl (e.g. 2-butenyl); alkynyl (e.g. 2-butynyl); aryl (e.g. phenyl, naphthyl or fluorenyl) and the like.

Alkyl

The terms "alkyl" and "$C_{1-6}$ alkyl" as used herein include reference to a straight or branched chain alkyl moiety having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, alkyl may have 1, 2, 3 or 4 carbon atoms.

Alkenyl

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

Alkynyl

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

Alkoxy

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl

The term "aryl" as used herein includes reference to an aromatic ring system comprising 6, 7, 8, 9 or 10 ring carbon atoms. Aryl is often phenyl but may be a polycyclic ring system, having two or more rings, at least one of which is aromatic. This term includes reference to groups such as phenyl, naphthyl and the like.

Carbocyclyl

The term "carbocyclyl" as used herein includes reference to a saturated (e.g. cycloalkyl) or unsaturated (e.g. aryl) ring moiety having 3, 4, 5, 6, 7, 8, 9 or 10 ring carbon atoms. In particular, carbocyclyl includes a 3- to 10-membered ring or ring system and, in particular, a 5- or 6-membered ring, which may be saturated or unsaturated. A carbocyclic moiety is, for example, selected from cyclopropyl, cyclobutyl, cyclopentyl, cyclohexyl, norbornyl, bicyclo[2.2.2]octyl, phenyl, naphthyl, and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9 or 10 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated.

A heterocyclic moiety is, for example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like.

Heteroaryl

The term "heteroaryl" as used herein includes reference to an aromatic heterocyclic ring system having 5, 6, 7, 8, 9 or 10 ring atoms, at least one of which is selected from nitrogen, oxygen and sulphur. The group may be a polycyclic ring system, having two or more rings, at least one of which is aromatic, but is more often monocyclic. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" as used herein includes reference to F, Cl, Br or I. In a particular, halogen may be F or Cl, of which F is more common.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or unsubstituted.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled man.

Pharmaceutically Acceptable

The term "pharmaceutically acceptable" as used herein includes reference to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. This term includes acceptability for both human and veterinary purposes.

Independently

Where two or more moieties are described as being "each independently" selected from a list of atoms or groups, this means that the moieties may be the same or different. The identity of each moiety is therefore independent of the identities of the one or more other moieties.

Compounds

The present invention provides compounds of the formula (I) and pharmaceutically acceptable salts, N-oxides and prodrugs thereof:

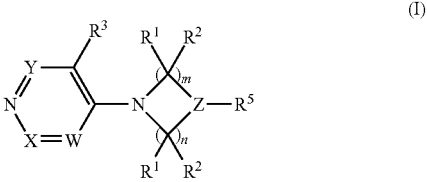

wherein W, X, Y, Z, $R^1$, $R^2$, $R^3$, $R^5$, m and n are as defined herein.

Various embodiments of the invention are described below. It will be appreciated that the features specified in each embodiment may be combined with other specified features, to provide yet further embodiments.

In an embodiment, m and n are each independently selected from 1 or 2.

In an embodiment, m and n are 1.

In an embodiment, one of m and n is 1, and the other is 2.

In an embodiment, m and n are each 2.

In an embodiment, $R^1$ and $R^2$ are each independently hydrogen or methyl; or $R^1$ and $R^2$ taken together with the carbon atom to which they are attached form a 5- or 6-membered heterocycle containing a ring heteroatom selected from O and N.

In an embodiment, $R^1$ and $R^2$ are each independently hydrogen or methyl.

In an embodiment, $R^1$ and $R^2$ are each hydrogen.

In an embodiment, X and Y are each independently selected from CH and $C(R^4)$, and W is selected from CH, $C(R^4)$ and N.

In an embodiment, X and Y are each CH; and W is CH, $C(R^4)$ or N.

In an embodiment, W is CH, $C(R^4)$, or N. In a particular embodiment, W is $C(R^4)$ or N.

In a further embodiment, W is $C(R^4)$. Of particular mention are compounds in which $R^4$ is halo, e.g. chloro or bromo.

In an embodiment, the heteroaryl ring shown in Formula (I) contains at least one ring nitrogen atom in the form of an N-oxide. Suitably, in such embodiments, it is the nitrogen atom disposed between atoms X and Y that is in the form of an N-oxide.

In an embodiment, $R^3$ is halo (e.g. chloro or bromo) or a group selected from $C_{1-6}$ alkyl, aryl and heteroaryl, any of which is optionally substituted with 1, 2, 3, 4 or 5 $R^a$. By way of example, each $R^a$ may be independently selected from halogen, cyano, amino, hydroxy, $C_{1-6}$ alkyl and $C_{1-6}$ alkoxy.

In a further embodiment, $R^3$ is halo (e.g. chloro or bromo) or a group selected from $C_{1-6}$ alkyl, $C_{3-6}$cycloalkyl, phenyl, and a 5- or 6-membered heteroaryl, any of which is optionally substituted with 1, 2, or 3 $R^a$. By way of example, each $R^a$ may be independently selected from halogen, cyano, amino, hydroxy, trifluoromethyl, $C_{1-4}$ alkyl, $NH(C_{1-4}alkyl)$, $N(C_{1-4}alkyl)_2$, $—S(O)_lC_{1-4}alkyl$ (where l is 0, 1 or 2) and $C_{1-4}$ alkoxy.

In an embodiment, $R^3$ is halo (e.g. chloro or bromo) or a group selected from $C_{1-6}$ alkyl (e.g. methyl or ethyl), phenyl, pyrazolyl, triazolyl, oxazolyl, isoxazolyl, pyridinyl, pyridazinyl, pyrimidinyl and thiophenyl, any of which is optionally substituted with 1, 2, 3, 4 or 5 $R^a$. By way of example, each $R^a$ may be independently selected from halogen, cyano, amino, hydroxy, $C_{1-6}$ alkyl and $C_{1-6}$ alkoxy. In an embodiment, $R^3$ is halo. In an embodiment, $R^3$ is $C_{1-6}$ alkoxy.

In an embodiment, $R^3$ is halo (e.g. chloro or bromo) or a group selected from $C_{1-6}$ alkyl (e.g. methyl or ethyl), $C_{3-6}$cycloalkyl (e.g. cyclopropyl), phenyl, pyrazolyl, triazolyl, oxazolyl, isoxazolyl, pyridinyl, pyridazinyl, pyrimidinyl. and thiophenyl, any of which is optionally substituted with 1, 2, or 3 $R^a$. By way of example, each $R^a$ may be independently selected from halogen, cyano, amino, hydroxy, trifluoromethyl, $C_{1-4}$ alkyl, $NH(C_{1-4}alkyl)$, $N(C_{1-4}alkyl)_2$, —S(O)$_l$ $C_{1-4}$alkyl (where l is 0, 1 or 2) and $C_{1-4}$ alkoxy.

In an embodiment, $R^3$ is halo. In an embodiment, $R^3$ is $C_{1-6}$ alkoxy. In an embodiment, $R^3$ is chloro, bromo or phenyl. In a particular embodiment, $R^3$ is chloro or bromo.

In an embodiment, $R^4$ is halo (e.g. chloro or bromo) or a group selected from $C_{1-6}$ alkyl, $C_{3-6}$cycloalkyl, phenyl, and a 5- or 6-membered heteroaryl, any of which is optionally substituted with 1, 2, or 3 $R^a$. In a further embodiment, $R^4$ is halo (e.g. chloro or bromo) or a group selected from $C_{1-6}$ alkyl (e.g. methyl or ethyl), $C_{3-6}$cycloalkyl (e.g. cyclopropyl), phenyl, pyrazolyl, triazolyl, oxazolyl, isoxazolyl, pyridinyl, pyridazinyl, pyrimidinyl. and thiophenyl, any of which is optionally substituted with 1, 2, or 3 $R^a$. By way of example, each $R^a$ may be independently selected from halogen, cyano, amino, hydroxy, trifluoromethyl, $C_{1-4}$ alkyl, $NH(C_{1-4}alkyl)$, $N(C_{1-4}alkyl)_2$, —S(O)$_l$$C_{1-4}$alkyl (where l is 0, 1 or 2) and $C_{1-4}$ alkoxy.

In an embodiment, Z is $C(R^6)$. Of particular mention are compounds in which $R^6$ is hydrogen, methyl, methoxy or methoxymethyl. In an embodiment, $R^6$ is selected from hydrogen, methyl or —N($R^7$)$R^8$. In a particular embodiment, $R^6$ is selected from hydrogen, methyl or —NH-phenyl. In a particular embodiment, $R^6$ is selected from hydrogen or methyl. In a further embodiment, $R^6$ is hydrogen.

In an embodiment, $R^5$ is H, CN, —C(O)OH, —C(O)O$R^7$—, —C(O)N($R^7$)$R^8$ or heterocyclyl. In another embodiment, $R^5$ is —C(O)OH or —CN. In another embodiment, $R^5$ is —CN. In an embodiment, $R^5$ is —C(O)N($R^6$)$R^7$. Of particular mention are compounds in which $R^5$ is —C(O)NH$_2$.

In an embodiment, $R^5$ and $R^6$ taken together with the carbon atom to which they are attached form a heterocycle optionally substituted with 1, 2, 3, 4 or 5 $R^a$. In a particular embodiment, $R^5$ and $R^6$ taken together with the carbon atom to which they are attached form a heterocycle comprising a ring amide group, e.g. oxazolidone or 2-oxopyrrolidine, wherein the heterocycle is optionally substituted with 1, 2, 3, 4 or 5 $R^a$. By way of example, each $R^a$ may be independently selected from halogen, cyano, amino, hydroxy, $C_{1-6}$ alkyl and $C_{1-6}$ alkoxy.

In an embodiment, $R^5$ is not an optionally substituted imidazolyl group.

In a further embodiment, when Z is N, $R^5$ is $R^7$, —C(O)$R^7$, —C(O)O$R^7$—, —C(O)N($R^7$)$R^8$ or a 5- or 6-membered heterocyclyl optionally substituted with 1, 2, 3, 4 or 5 $R^a$. In a further embodiment, when Z is N, $R^5$ is $C_{1-6}$ alkyl optionally substituted with one or more $R^a$, —C(O)$R^7$ or —C(O)N($R^7$)$R^8$.

In an embodiment, when Z is $C(R^6)$, $R^5$ is H, CN, C(O)OH, —C(O)$R^7$, —C(O)O$R^7$—, —S(O)$_l$$R^7$, —N($R^7$)$R^8$, —C(O)N($R^7$)$R^8$, —C(S)N($R^7$)$R^8$, —S(O)$_l$N($R^7$)$R^8$, —N($R^7$)C(O)$R^8$, —N($R^7$)S(O)$_l$$R^8$ or an $C_{1-6}$ alkyl, phenyl or 5- or 6-membered heterocyclyl group which is optionally substituted with 1, 2, 3, 4 or 5 $R^a$.

In a further embodiment, when Z is $C(R^6)$, $R^5$ is H, CN, C(O)OH, —C(O)$R^7$, —C(O)O$R^7$—, —N($R^7$)$R^8$, —C(O)N($R^7$)$R^8$, —C(S)N($R^7$)$R^8$, —S(O)$_l$N($R^7$)$R^8$, —N($R^7$)C(O)$R^8$, —N($R^7$)S(O)$_l$$R^8$ or an $C_{1-6}$ alkyl or 5- or 6-membered heterocyclyl group which is optionally substituted with 1, 2, or 3 $R^a$.

In a further embodiment, when Z is $C(R^6)$, $R^5$ is CN, C(O)OH, —C(O)$R^7$, —C(O)O$R^7$—, —N($R^7$)$R^8$, —C(O)N($R^7$)$R^8$, —C(S)N($R^7$)$R^8$, —N($R^7$)C(O)$R^8$, or an $C_{1-4}$ alkyl or 5- or 6-membered heterocyclyl group which is optionally substituted with 1, 2, or 3 $R^a$.

In an embodiment, $R^5$ and $R^6$ are linked so that, together with the carbon atom to which they are attached, they form a 5- or 6-membered heterocycle which is optionally substituted with 1, 2, or 3 $R^a$. In an embodiment, $R^5$ and $R^6$ together form a group —C(O)—N($R^7$)—(CH$_2$)$_q$—, where q is 2 or 3.

In an embodiment, $R^7$ and $R^8$ are each independently hydrogen or a group selected from $C_{1-6}$ alkyl, carbocyclyl and heterocyclyl, any of which is optionally substituted with 1, 2, 3, 4 or 5 $R^a$.

In a further embodiment, $R^7$ and $R^8$ are each independently hydrogen or a group selected from $C_{1-6}$ alkyl, phenyl and 5- or 6-membered heterocyclyl, any of which is optionally substituted with 1, 2 or 3 $R^a$. In a further embodiment, at least one of $R^7$ and $R^8$ is hydrogen.

In an embodiment, $R^7$ and $R^8$ are connected to a common nitrogen atom and are linked so that, together with the nitrogen atom to which they are attached, they form a 5- or 6-membered heterocycle which is optionally substituted with 1, 2, 3, 4 or 5 $R^a$. In a particular embodiment, $R^7$ and $R^8$ are linked so that, together with the nitrogen atom to which they are attached, they form a pyrrolidine, piperidine, piperazine, or morpholine ring which is optionally substituted with 1, 2 or 3 $R^a$.

In an embodiment, each $R^a$ group is independently selected from halogen, trifluoromethyl, cyano, oxo, nitro, —O$R^b$, —C(O)$R^b$, —C(O)O$R^b$, —OC(O)$R^b$, —S(O)$_l$$R^b$, —N($R^b$) $R^c$, —N($R^b$)C(O)$R^c$, —C(O)N($R^b$)$R^c$, —S(O)$_l$N($R^b$)$R^c$ and $R^d$. In a further embodiment, each $R^a$ group is independently selected from halogen, trifluoromethyl, oxo, —O$R^b$, —C(O)$R^b$, —S(O)$_l$$R^b$, —N($R^b$)$R^c$, —N($R^b$)C(O)$R^c$, —C(O)N($R^b$)$R^c$ and $R^d$.

In an embodiment, $R^d$ is selected from $C_{1-6}$alkyl, $C_{3-6}$cycloalkyl, phenyl and a 5- or 6-membered heterocyclyl, each of which is optionally substituted with 1, 2, 3, 4 or 5 substituents independently selected from halogen, cyano, amino, hydroxy, $C_{1-6}$ alkyl and $C_{1-6}$ alkoxy.

In a further embodiment, $R^d$ is selected from $C_{1-6}$alkyl, $C_{3-6}$cycloalkyl, phenyl and a 5- or 6-membered heterocyclyl, each of which is optionally substituted with 1, 2 or 3 substituents independently selected from halogen, cyano, amino, hydroxy, $C_{1-4}$ alkyl and $C_{1-4}$ alkoxy.

In an embodiment, the compound is of the following formula:

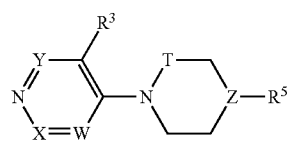

wherein T is a bond or —CH$_2$—.

In an embodiment, the compound is of the following formula:

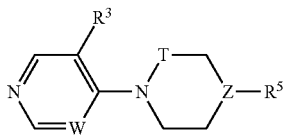

In an embodiment, the compound is of the following formula:

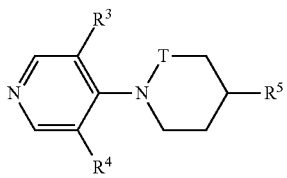

In an embodiment, the compound is of the following formula:

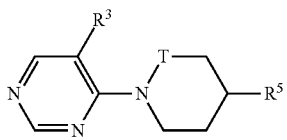

In an embodiment, the compound is of the following formula:

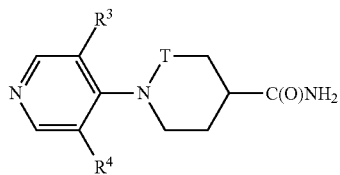

In an embodiment, the compound is of the following formula:

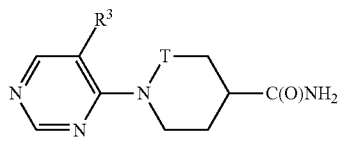

In an embodiment, the compound is of the following formula:

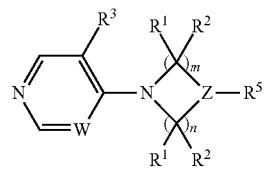

wherein
W is $=C(R^4)-$ or $=N-$;
Z is $C(R^6)$;
$R^1$ and $R^2$ are each hydrogen;
$R^3$ and $R^4$ are each independently halo or a group selected from $C_{1-6}$ alkyl, $C_{1-6}$ alkoxy, carbocyclyl and heterocyclyl, any of which is optionally substituted with 1, 2, 3, 4 or 5 $R^a$;
$R^5$ is H, CN, $-C(O)OH$, $-C(O)N(R^7)R^8$, or heterocyclyl;
$R^6$ is hydrogen, $C_{1-6}$ alkyl, $C_{1-6}$ alkoxy, $-OH$, $R^5$; or $(CH_2)_m R^5$;
or $R^5$ and $R^6$ taken together with the carbon atom to which they are attached form a 5- or 6-membered heterocycle which is optionally substituted with 1, 2, 3, 4 or 5 $R^a$;
$R^7$ and $R^8$ are each independently hydrogen or a group selected from $C_{1-6}$ alkyl optionally containing 1, 2 or 3 heteroatoms selected from N and O, carbocyclyl and heterocyclyl;
each $R^a$ is independently selected from halogen, trifluoromethyl, cyano, oxo, nitro, $-OR^b$, $-C(O)R^b$, $-C(O)OR^b$, $-OC(O)R^b$, $-S(O)_l R^b$, $-N(R^b)R^c$, $-N(R^b)C(O)R^c$, $-C(O)N(R^b)R^c$, $-S(O)_l N(R^b)R^c$ and $R^d$;
$R^b$ and $R^c$ are each independently hydrogen or $R^d$;
$R^d$ is selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;
l is 0, 1 or 2; and
m and n are each independently 1 or 2;
or a pharmaceutically acceptable salt, N-oxide or prodrug thereof.

In a further aspect, the present invention provides any one of the compounds listed in the accompanying examples.

Compounds of the invention may be in the form of pharmaceutically acceptable salts. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts may be found in *Remington's Pharmaceutical Sciences*, 17th ed., Mack Publishing Company, Easton, Pa., US, 1985, p. 1418, the disclosure of which is hereby incorporated by reference; see also Stahl et al, Eds, "*Handbook of Pharmaceutical Salts Properties Selection and Use*", Verlag Helvetica Chimica Acta and Wiley-VCH, 2002.

The invention thus includes pharmaceutically-acceptable salts of the disclosed compounds wherein the parent compound is modified by making acid or base salts thereof, for example the conventional non-toxic salts or the quaternary ammonium salts which are formed, e.g. from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention includes prodrugs for the active pharmaceutical species of the invention, for example in which one or more functional groups are protected or derivatised but can be converted in vivo to the functional group, as in the case of esters of carboxylic acids convertible in vivo to the free acid, or in the case of protected amines, to the free amino group. The term "prodrug," as used herein, represents in particular compounds which are rapidly transformed in vivo to the parent compound, for example, by hydrolysis in blood. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Pro-drugs, Elsevier, 1985; and Judkins, et al. Synthetic Communications, 26(23), 4351-4367 (1996), each of which is incorporated herein by reference.

Prodrugs therefore include drugs having a functional group which has been transformed into a reversible derivative thereof. Typically, such prodrugs are transformed to the active drug by hydrolysis. Examples of such groups include carboxylic groups (reversible derivatives including esters, e.g. acyloxyalkyl esters and amides), alcohol groups (reversible derivatives including sulfates, phosphates and carboxylic acid esters), amine groups (reversible derivatives including amides, carbamates, imines and enamines) and carbonyl groups, e.g. aldehyde and ketone groups (reversible derivatives including imines, oximes, acetals/ketals, enol esters, oxazolidines and thiazoxolidines).

Prodrugs also include compounds convertible to the active drug by an oxidative or reductive reaction. As examples of oxidative activation may be mentioned N- and O-dealkylation, oxidative deamination, N-oxidation and epoxidation. As examples of reductive activation may be mentioned azo reduction, sulfoxide reduction, disulfide reduction, bioreductive alkylation and nitro reduction.

Also to be mentioned as metabolic activations of prodrugs are nucleotide activation, phosphorylation activation and decarboxylation activation. For additional information, see "The Organic Chemistry of Drug Design and Drug Action", R B Silverman (particularly Chapter 8, pages 497 to 546), incorporated herein by reference.

The use of protecting groups is fully described in 'Protective Groups in Organic Chemistry', edited by J W F McOmie, Plenum Press (1973), and 'Protective Groups in Organic Synthesis', $2^{nd}$ edition, T W Greene & P G M Wutz, Wiley-Interscience (1991).

Thus, it will be appreciated by those skilled in the art that, although protected derivatives of compounds of the disclosure may not possess pharmacological activity as such, they may be administered, for example parenterally or orally, and thereafter metabolised in the body to form compounds of the invention which are pharmacologically active. Such derivatives are therefore examples of "prodrugs". All prodrugs of the described compounds are included within the scope of the disclosure.

Some groups mentioned herein (especially those containing heteroatoms and conjugated bonds) may exist in tautomeric forms and all these tautomers are included in the scope of the disclosure. More generally, many species may exist in equilibrium, as for example in the case of organic acids and their counterpart anions; a reference herein to a species accordingly includes reference to all equilibrium forms thereof.

The compounds of the disclosure may also contain one or more asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the disclosure. Where a single enantiomer or diasteromer is disclosed, the disclosure also covers the other enantiomers or diastereomers, and also racemates; in this regard, particular reference is made to the specific compounds listed herein.

Geometric isomers may also exist in the compounds of the present disclosure. The present disclosure contemplates the various geometric isomers and mixtures thereof resulting from the arrangement of substituents around a carbon-carbon double bond and designates such isomers as of the Z or E configuration, wherein the term "Z" represents substituents on the same side of the carbon-carbon double bond and the term "E" represents substituents on opposite sides of the carbon-carbon double bond.

The disclosure therefore includes all variant forms of the defined compounds, for example any tautomer or any pharmaceutically acceptable salt, ester, acid or other variant of the defined compounds and their tautomers as well as substances which, upon administration, are capable of providing directly or indirectly a compound as defined above or providing a species which is capable of existing in equilibrium with such a compound.

Synthesis

A compound of the invention may be prepared according to the processes described herein. It will be understood that these processes are solely for the purpose of illustrating the invention and should not be construed as limiting. A process utilising similar or analogous reagents and/or conditions known to one skilled in the art may also be used to obtain a compound of the invention.

Any mixtures of final products or intermediates obtained can be separated on the basis of the physico-chemical differences of the constituents, in a known manner, into the pure final products or intermediates, for example by chromatography, distillation, fractional crystallisation, or by the formation of a salt if appropriate or possible under the circumstances.

Administration & Pharmaceutical Formulations

The compounds of the invention will normally be administered orally, intravenously, subcutaneously, buccally, rectally, dermally, nasally, tracheally, bronchially, by any other parenteral route, as an oral or nasal spray or via inhalation, The compounds may be administered in the form of pharmaceutical preparations comprising prodrug or active compound either as a free compound or, for example, a pharmaceutically acceptable non-toxic organic or inorganic acid or base addition salt, in a pharmaceutically acceptable dosage form. Depending upon the disorder and patient to be treated and the route of administration, the compositions may be administered at varying doses.

Typically, therefore, the pharmaceutical compounds of the invention may be administered orally or parenterally ("parenterally" as used herein, refers to modes of administration which include intravenous, intramuscular, intraperitoneal, intrasternal, subcutaneous and intraarticular injection and infusion) to a host. In the case of larger animals, such as humans, the compounds may be administered alone or as compositions in combination with pharmaceutically acceptable diluents, excipients or carriers.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

In certain embodiments, an appropriate dosage level will generally be about 0.01 to 500 mg per kg patient body weight per day which can be administered in single or multiple doses. In a particular embodiment, the dosage level is about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0 and 1000.0 milligrams of the active ingredient for the symptomatic adjustment of the dosage to the patient to be treated. The compounds may be administered on a regimen of 1 to 4 times per day, e.g. once or twice per day. The dosage regimen may be adjusted to provide the optimal therapeutic response.

According to a further aspect of the invention there is thus provided a pharmaceutical composition including a compound of the invention, in admixture with a pharmaceutically acceptable adjuvant, diluent or carrier.

Pharmaceutical compositions of this invention for parenteral injection suitably comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms may be ensured by the inclusion of various antibacterial and antifungal agents, for example, paraben, chlorobutanol or phenol sorbic acid. It may also be desirable to include isotonic agents such as sugars or sodium chloride, for example. Prolonged absorption of the injectable pharmaceutical form may be brought about by the inclusion of agents (for example aluminum monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are suitably made by forming microencapsule matrices of the drug in biodegradable polymers, for example polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the active compound is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, oral formulations contain a dissolution aid. The dissolution aid is not limited as to its identity so long as it is pharmaceutically acceptable. Examples include nonionic surface active agents, such as sucrose fatty acid esters, glycerol fatty acid esters, sorbitan fatty acid esters (e.g. sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g. chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions include polymeric substances and waxes.

The active compounds may also be in micro-encapsulated form, if appropriate, with one or more of the above-mentioned excipients.

The active compounds may be in finely divided form, for example they may be micronised.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and the phosphatidyl cholines (lecithins), both natural and synthetic. Methods to form liposomes are known in the art, for example, Prescott, Ed., Methods in Cell Biology, Volume XIV, Academic Press, New York, N.Y. (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which may be required. Ophthalmic formulations, eye ointments, powders and solutions are also contemplated as being within the scope of this invention.

Use

Compounds of the invention may be useful in the therapy of a variety of diseases and conditions. The subject of said therapy may be a human or an animal. Compounds of the invention may exhibit desirable potency, selectivity and microsomal stability.

In particular, compounds of the invention may be useful in the treatment or prevention of cancer, such as cancer of the colon, breast or liver.

The following Examples illustrate the invention.

General Synthesis

Example compounds were prepared according to the following reaction schemes.

A 3-step procedure consisting of coupling of N-Boc-isonipecotic acid with a series of amines utilising HATU as the coupling reagent. Deprotection of the resultant piperidine under acidic conditions, followed by microwave mediated $S_NAr$ coupling furnished amide analogues A in good yield.

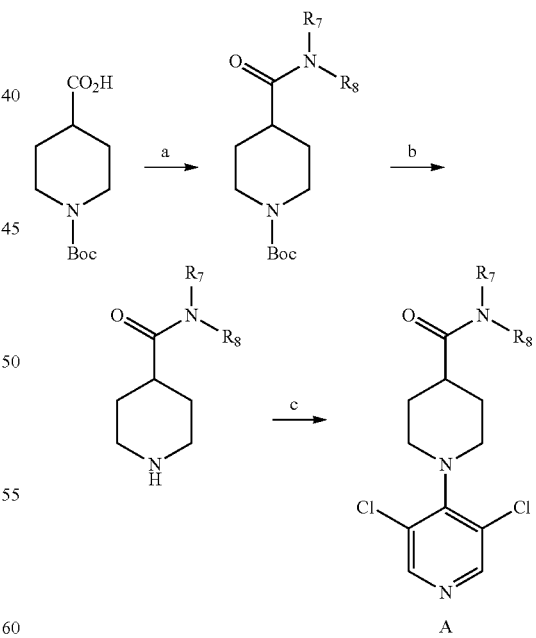

Reagents and conditions: a) RR'NH, HATU, DIPEA, DMF; b) 4M HCl-dioxane, MeOH 1:1; c) 3,4,5-trichloropyridine, NEt₃, NMP, 220° C., 60 min.

Both 4-chloropyridine and 3,4-dichloropyridine were commercially available as their hydrochloride salts. The reaction was carried out in water using an excess of isonipecotamide, leading to excellent conversion into the desired products B & C. The products were found to crystallise upon cooling the reaction mixture to 0° C.

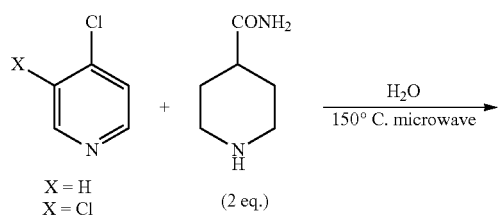

Amides of the piperidine were first synthesised then coupled to the pyridine fragment. Thus, 1-Boc-4-aminopiperidine was coupled with carboxylic acids to furnish amides. N-deprotection generated free piperidines, which underwent S$_N$Ar coupling with 3,4,5-trichloropyridine to give analogues D.

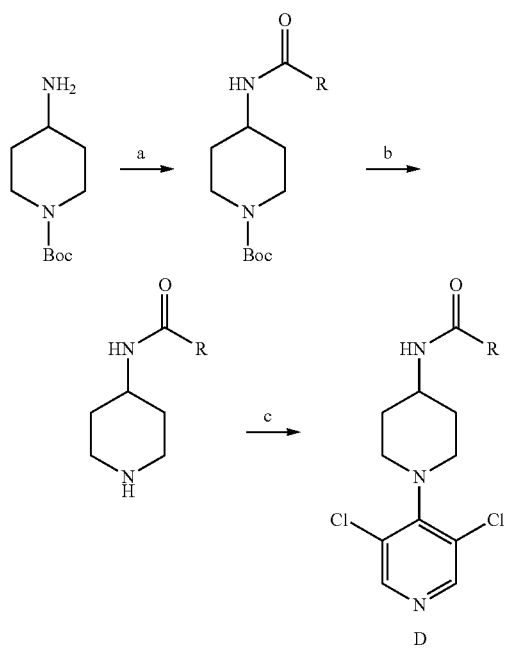

Reagents and Conditions: a) RCO$_2$H, HATU, DIPEA, DMF; b) 4M HCl-dioxane, MeOH 1:1; c)3,4,5-trichloropyridine, NEt$_3$, NMP, 220° C., 60 min.

The intermediate 4-chloro-3,5-dimethylpyridine was synthesised by the selective chlorination of 3,5-lutidine as reported by Wurster et al (J. Med. Chem. 2006, 49, 6351):

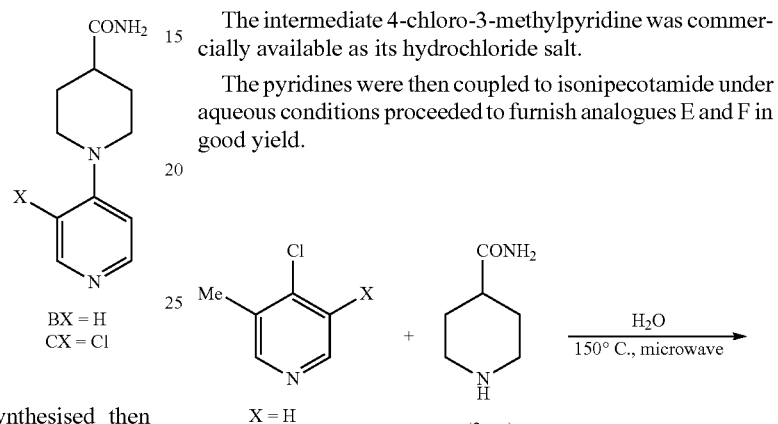

The intermediate 4-chloro-3-methylpyridine was commercially available as its hydrochloride salt.

The pyridines were then coupled to isonipecotamide under aqueous conditions proceeded to furnish analogues E and F in good yield.

Oxidation of the pyridine ring may be achieved using the conditions developed by Caron et al (Tetrahedron Lett. 2000, 41, 2299) for the oxidation of electron deficient pyridines. The highly reactive oxidising agent pertrifluoroacetic acid is generated in-situ from hydrogen peroxide-urea complex and trifluoroacetic anhydride.

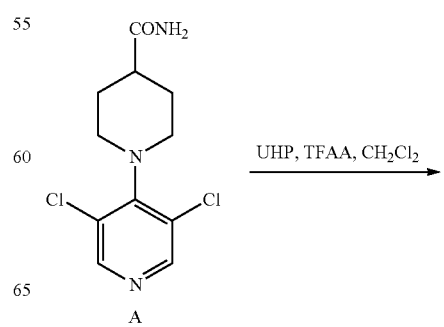

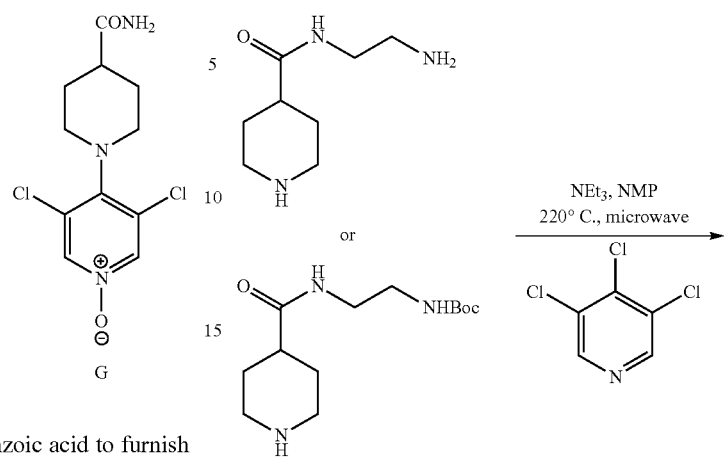

N-Boc-piperazine was coupled to benzoic acid to furnish the amide which was subsequently deprotected and coupled to 3,4,5-trichloropyridine to give H. Similarly 3,4,5-trichloropyridine has been coupled to commercially available N-acetyl, N-methyl and N-ethyl piperazines to furnish compounds I, J, K respectively.

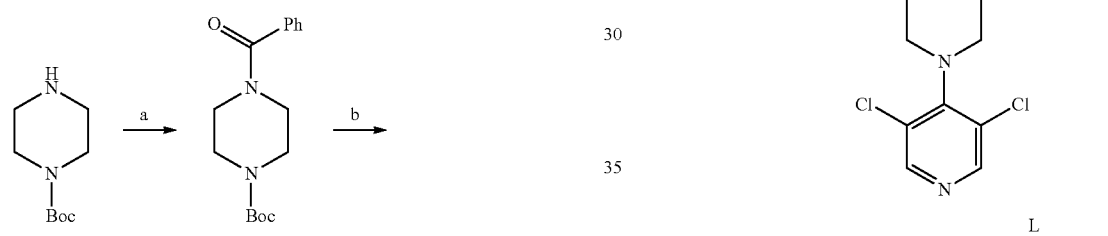

21

HX = O, R = Ph
IX = O, R = Me
JX = H₂, R = H
KX = H₂, R = Me

Reagents and Conditions: a) PhCO₂H, HATU, DIPEA, DMF; b) 4M HCl-dioxane, MeOH 1:1; c) 3,4,5-trichloropyridine, NEt₃, NMP, 220° C., 60 min.

This scheme was used to synthesise amide analogues derived from ethylenediamine. The tert-butoxycarbonyl protecting group was thermally removed during the coupling reaction, leading to bis-coupled product L.

Carboxybenzyl derivative M was synthesised according to the scheme below, however attempts at deprotection via hydrogenation led to hydrogenation of the chloride groups, to furnish N.

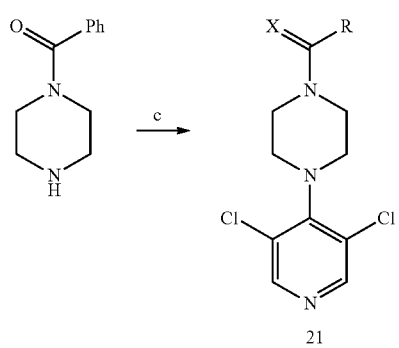

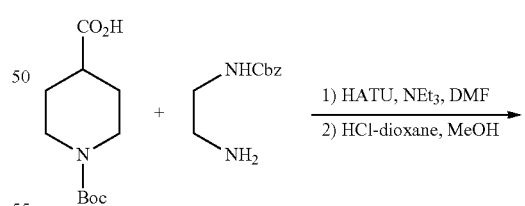

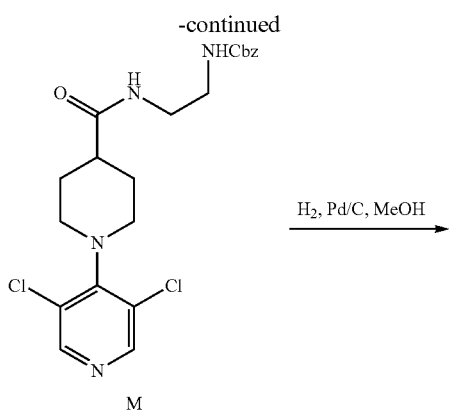

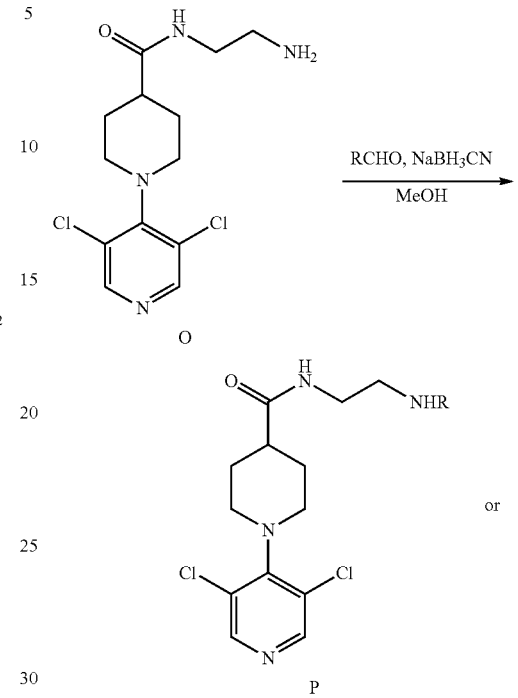

To this end, the Lewis acid mediated cleavage conditions as reported by Stammer et al (*J. Chem. Soc., Chem. Comm.* 1979, 495) were used to selectively cleave the protecting group using trimethylsilyl iodide to furnish O in good yield.

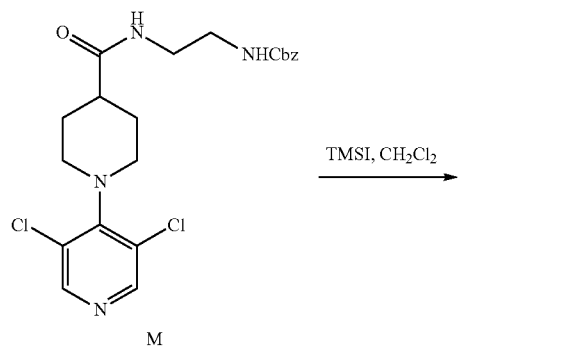

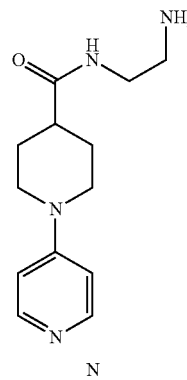

Compound O was then subjected to reductive amination utilising a diverse set of aldehydes to furnish further analogues P where stoichiometric amounts of aldehyde were employed or Q when an excess of aldehyde was used.

A series of analogues of the primary amide functionality were synthesised by conventional methods. Thus, treatment of the primary amide with Lawesson's reagent furnished the thioamide R, whilst treatment with vinylene carbonate furnished oxazolone S. Thioamide R could be further converted into thiazole T upon treatment with chloroacetaldehyde.

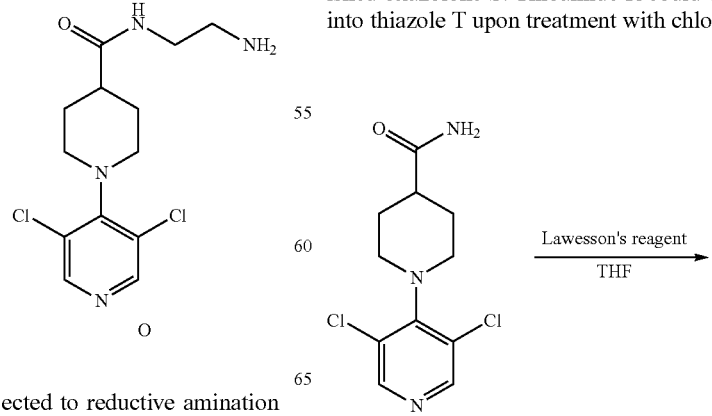

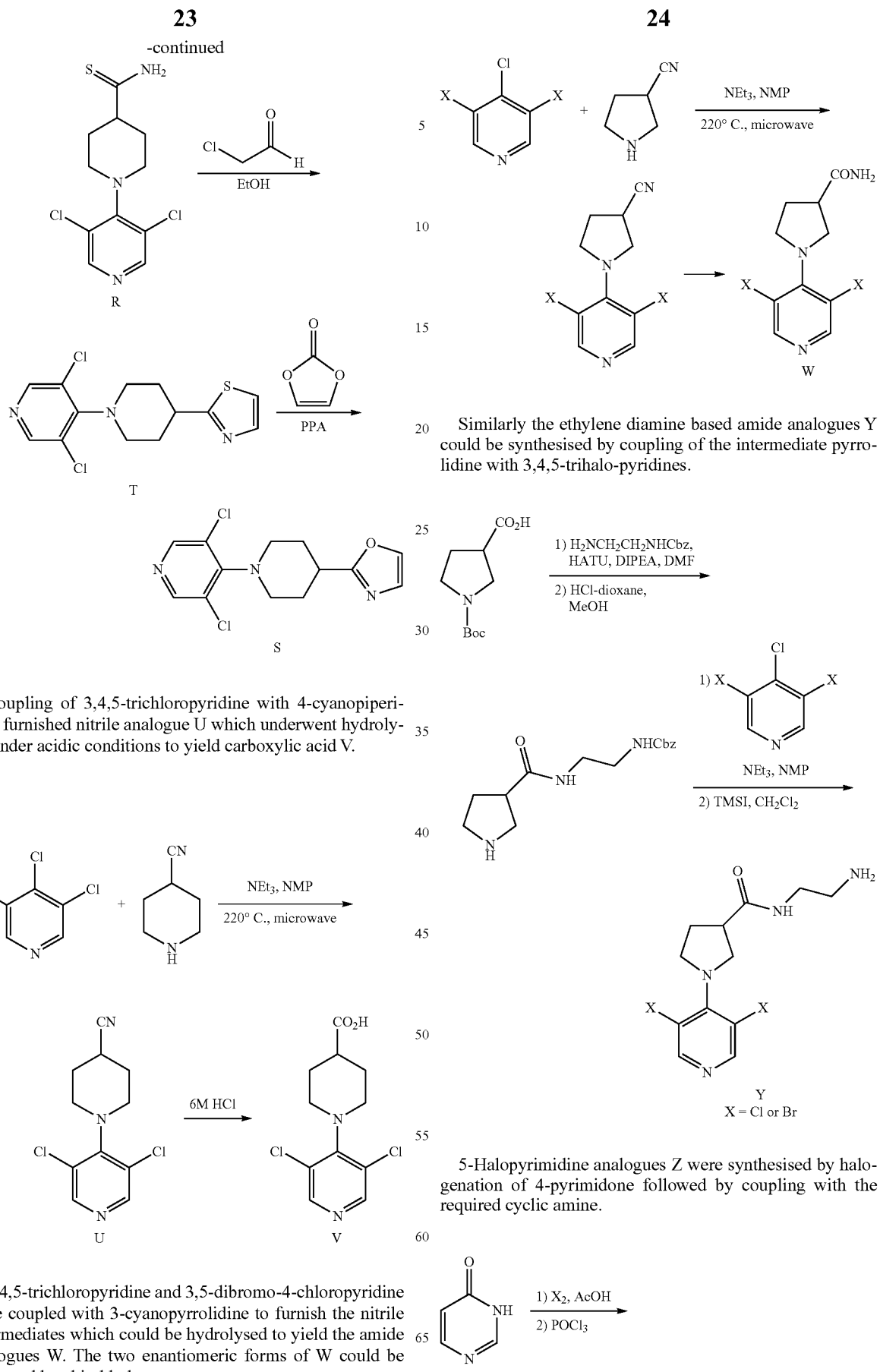

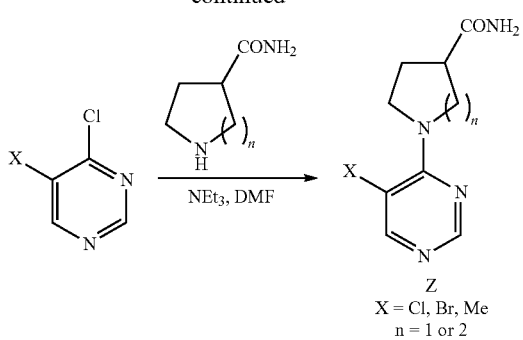

A more robust route was also established in which the 2-chloro pyrimidine intermediate was first synthesised and then subjected to hydrogenolysis. The intermediate 5-bromopyrimidine also underwent Suzuki reaction to furnish aryl analogues AA.

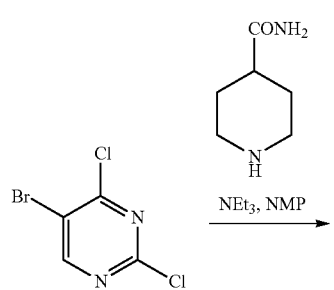

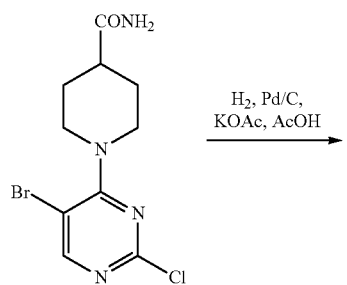

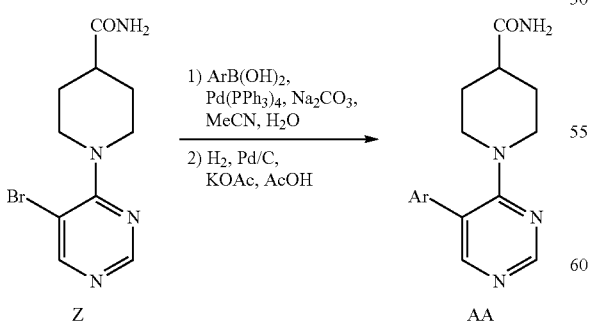

Similarly, Suzuki reaction with aryl and heteroaryl boronic acids and 5-bromopyridine analogue furnished aryl analogues BB in excellent yield.

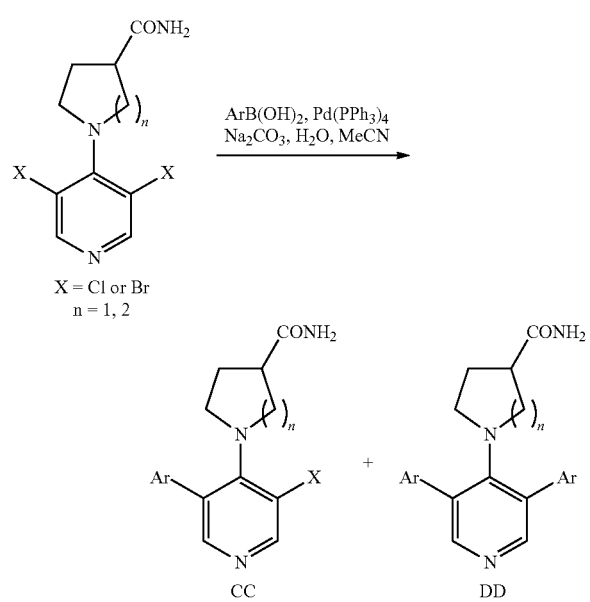

In the same way, 3-halo-5-aryl pyridine analogues CC were prepared from the dichloro- and dibromo-pyridines taking care to avoid double coupling. By using an excess of the boronic acids the double Suzuki reaction to furnish only the bis-aryl analogues DD could also be performed successfully.

Intermediate 1: tert-butyl-4-(methylcarbamoyl)piperidine-1-carboxylate 1

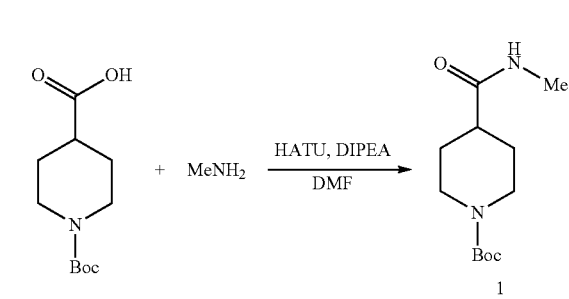

General Procedure A

To a solution of N-Boc-isonipecotic acid (0.20 g, 0.86 mmol) and HATU (0.43 g, 1.1 mmol) in DMF (4 mL) was added DIPEA (0.76 mL, 4.4 mmol). After stirring the solution for 5 min, methylamine hydrochloride (76 mg, 1.1 mmol) was added. After allowing the solution to stir for a further 16 h, it was poured into a 1 M solution of sodium hydroxide (50 mL) and extracted with EtOAc (2×50 mL). The combined organic extracts were washed with water (50 mL), 1 M hydrochloric acid (50 mL), water (50 mL) and brine (50 mL). The organic phase was dried (MgSO$_4$) and the solvent was evaporated under reduced pressure to yield the title compound as a pale yellow oil (69 mg, 33%), u$_{max}$ (CHCl$_3$)/cm$^{-1}$ 3009, 2932, 1677, 1522, 1429, 1279, 1166; m/z (ESI) C$_{12}$H$_{22}$N$_2$NaO$_3$ requires 265.1523, found [M+Na]$^+$ 265.1525.

Intermediate 2: tert-butyl-4-(dimethylcarbamoyl) piperidine-1-carboxylate 2

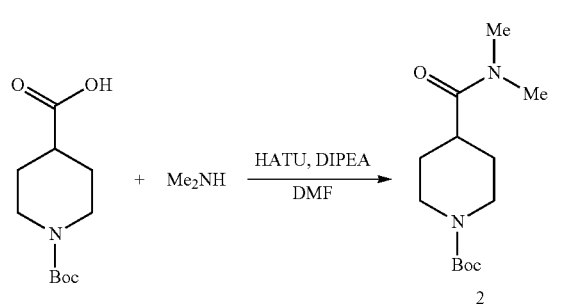

General procedure A was followed using N-Boc-isonipecotic acid (0.20 g, 0.86 mmol), HATU (0.43 g, 1.1 mmol), DIPEA (0.76 mL, 4.4 mmol), dimethylamine hydrochloride (92 mg, 1.1 mmol) and DMF (4 mL) to furnish the title compound as a pale brown oil (156 mg, 70%), u$_{max}$(CHCl$_3$)/cm$^{-1}$ 3020, 2861, 1684, 1631, 1417, 1367, 1151, 1030; m/z (ESI) C$_{13}$H$_{24}$N$_2$NaO$_3$ requires 279.1679, found [M+Na]$^+$ 279.1677.

Intermediate 3: tert-butyl-4-(2-(tert-butoxycarbonylamino)ethylcarbamoyl)piperidine-1-carboxylate 3

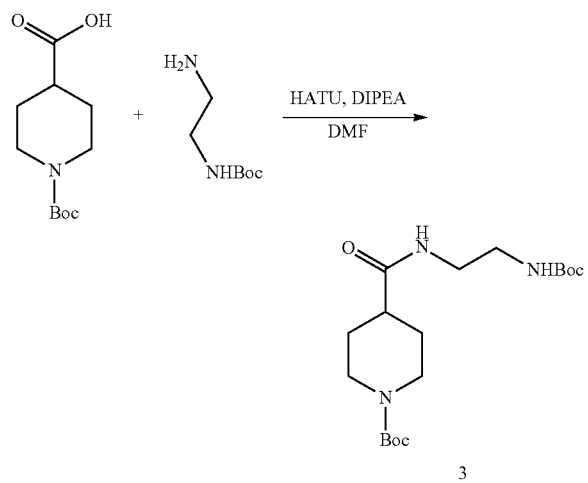

General procedure A was followed using N-Boc-isonipecotic acid (0.20 g, 0.86 mmol), HATU (0.43 g, 1.1 mmol), DIPEA (0.76 mL, 4.4 mmol), N-Boc-ethylenediamine (0.18 g, 1.1 mmol) and DMF (4 mL) to furnish the title compound as a beige solid (311 mg, 96%), m.p. 172-174° C.; u$_{max}$ (CHCl$_3$)/cm$^{-1}$ 3022, 2981, 1684, 1671, 1507, 1367, 1241, 1165; m/z (ESI) C$_{18}$H$_{33}$N$_3$NaO$_5$ requires 394.2312, found [M+Na]$^+$ 394.2310.

Intermediate 4: tert-butyl-4-(2-(benzyloxycarbonylamino)ethylcarbamoyl)piperidine-1-carboxylate 4

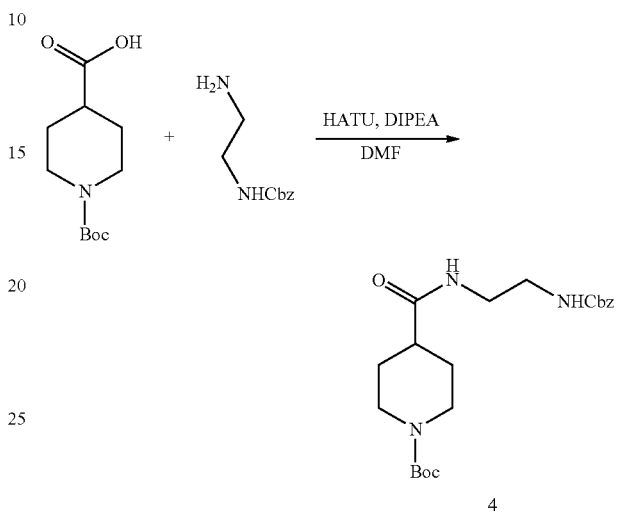

General procedure A was followed using N-Boc-isonipecotic acid (0.10 g, 0.44 mmol), HATU (0.22 g, 0.57 mmol), DIPEA (0.38 mL, 2.2 mmol), N-Cbz-ethylenediamine (0.11 g, 0.57 mmol) and DMF (2 mL) to furnish the title compound as a yellow wax (170 mg, 96%), u$_{max}$ (CHCl$_3$)/cm$^{-1}$ 3361, 3024, 2943, 1713, 1683, 1519, 1428, 1236, 1166; m/z (ESI) C$_{21}$H$_{32}$N$_3$O$_5$ requires 406.2337, found [M+H]$^+$ 406.2330.

Intermediate 5: N-methylpiperidine-4-carboxamide 5

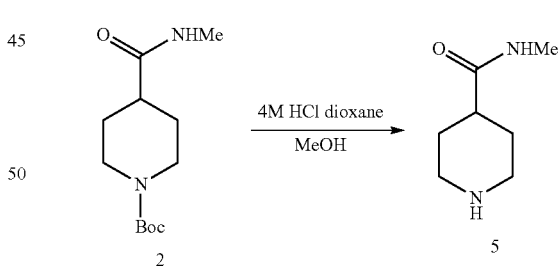

General Procedure B

To a solution of tert-butyl-4-(methylcarbamoyl)piperidine-1-carboxylate 1 (68 mg, 0.28 mmol) in MeOH (2 mL), cooled to 0° C., was added a 4 M solution of hydrogen chloride in 1,4-dioxane (2 mL). After stirring for 15 min, the solution was allowed to warm to room temperature and after stirring for a further period of further 3 h, the solvent was removed under reduced pressure. The crude product was purified by chromatography on a SCX-2 cartridge (MeOH followed by 0.5 M NH$_3$ in MeOH) to furnish the title compound as a colourless oil (41 mg, 99%), u$_{max}$ (CHCl$_3$)/cm$^{-1}$ 3008, 2948, 1663, 1525, 1227, 1199; m/z (ESI) $C_7H_{15}N_2O$ requires 143.1179, found $[M+H]^+$ 143.1178.

Intermediate 6: N,N-dimethylpiperidine-4-carboxamide 6

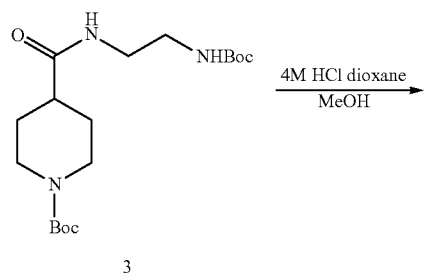

General procedure B was followed using tert-butyl-4-(dimethylcarbamoyl)piperidine-1-carboxylate 2 (0.16 g, 0.60 mmol), MeOH (2.5 mL) and a 4 M solution of hydrogen chloride in 1,4-dioxane (2.5 mL) to furnish the title compound as a pale yellow oil (67 mg, 71%), $u_{max}$ $(CHCl_3)/cm^{-1}$ 3003, 2947, 1625, 1497, 1401, 1320, 1240, 1137, 1105; m/z (ESI) $C_8H_{17}N_2O$ requires 157.1335, found $[M+H]^+$ 157.1338.

Intermediate 7: N-(2-aminoethyl)piperidine-4-carboxamide 7

$u_{max}$ $cm^{-1}$ 3284, 3940, 1647, 1550, 1139, 1035; m/z (ESI) $C_8H_{18}N_3O$ requires 172.1444, found $[M+H]^+$ 172.1445.

Intermediate 8: benzyl 2-(piperidine-4-carboxamido)ethylcarbamate 8

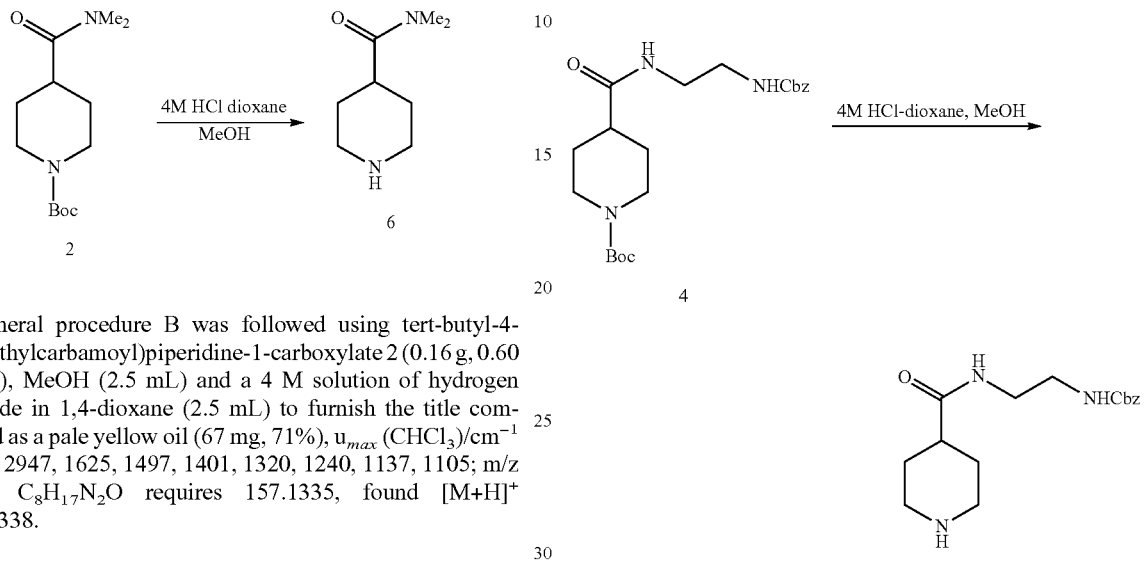

General procedure B was followed tert-butyl-4-(2(benzyloxycarbonylamino) ethylcarbamoyl)piperidine-1-carboxylate 4 (0.19 g, 0.46 mmol), MeOH (3 mL) and a 4 M solution of hydrogen chloride in 1,4-dioxane (3 mL) to furnish the title compound as a colourless oil (108 mg, 76%), m.p. 165-167° C.; $u_{max}$ $(CHCl_3)/cm^{-1}$ 3013, 2946, 1713, 1661, 1519, 1260, 1226, 1140, 1014; m/z (ESI) $C_{16}H_{24}N_3O_3$ requires 306.1812, found $[MH]^+$ 306.1808.

Intermediate 9: tert-butyl 4-benzoylpiperazine-1-carboxylate 9

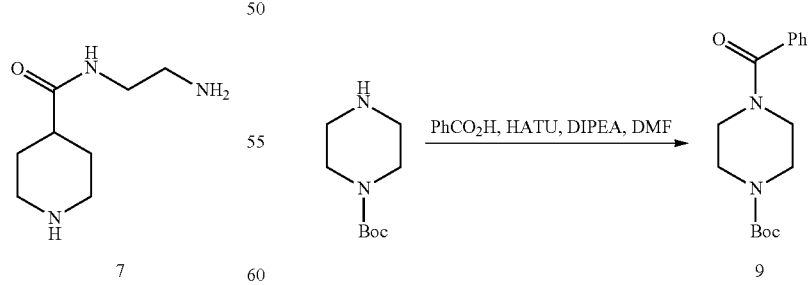

General procedure B was followed tert-butyl-4-(2-(tert-butoxycarbonylamino)ethyl carbamoyl)piperidine-1-carboxylate 3 (0.31 g, 0.83 mmol), MeOH (5 mL) and a 4 M solution of hydrogen chloride in 1,4-dioxane (5 mL) to furnish the title compound as a colourless oil (109 mg, 76%), General procedure A was followed using 1-Boc-piperazine (50 mg, 0.27 mmol), benzoic acid (43 mg, 0.35 mmol), HATU (0.14 g, 0.35 mmol), DIPEA (0.23 ml 1.4 mmol) and DMF (2 mL) to furnish the title compound as a beige solid (75 mg, 98%), m.p. 105-107° C.; $u_{max}$ $(CHCl_3)/cm^{-1}$ 3011, 2930, 2866, 1691, 1626, 1421, 1249, 1158; m/z (ESI) $C_{16}H_{22}N_2NaO_3$ requires 313.1523, found $[M+Na]^+$ 313.1528.

Intermediate 10: 4-benzoylpiperazine-1-carboxylate 10

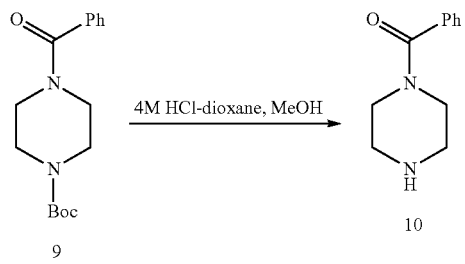 [SMILES: CC(C)(C)OC(=O)N1CCN(C(=O)c2ccccc2)CC1 ; O=C(c1ccccc1)N1CCNCC1]

General procedure B was followed using tert-butyl 4-benzoylpiperazine-1-carboxylate 9 (75 mg, 0.26 mmol), MeOH (2 mL) and a 4 M solution of hydrogen chloride in 1,4-dioxane (2 mL) to furnish the title compound as a colourless oil (47 mg, 96%), $u_{max}$ $(CHCl_3)/cm^{-1}$ 3015, 2954, 1622, 1435, 1290, 1136, 1018; m/z (ESI) $C_{11}H_{15}N_2O$ requires 191.1179, found $[M+H]^+$ 191.1179.

Intermediate 11: benzyl-2-(1-(3,5-dichloropyridin-4-yl)piperidine-4-carboxamido) ethyl carbamate 11

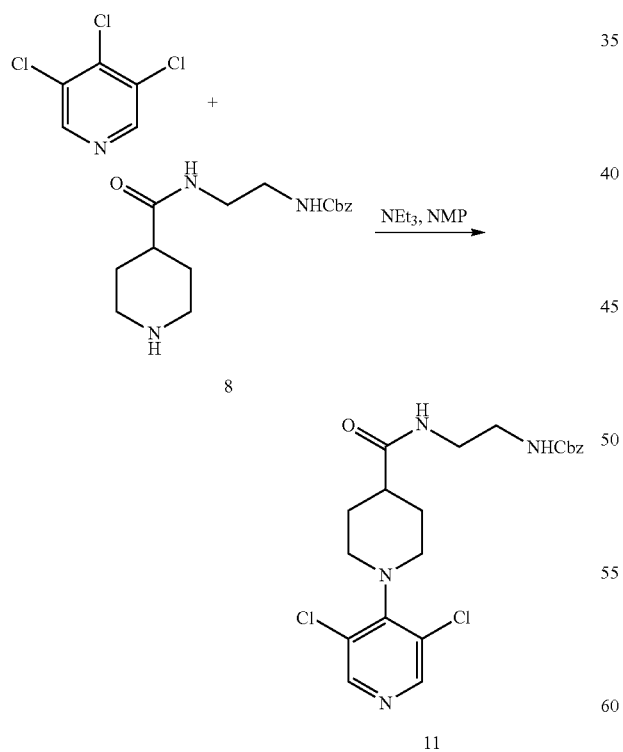

General procedure C (See Example 1) was followed using benzyl-2-(piperidine-4-carboxamido)ethylcarbamate 14 (59 mg, 0.19 mmol), 3,4,5-trichloropyridine (35 mg, 0.19 mmol), triethylamine (27 µL, 0.58 mmol) and NMP (1.5 mL). The crude product was purified by flash column chromatography on silica gel (hexane/EtOAc, 1:1) to furnish the title compound as a white solid (42 mg, 48%), m.p. 147-149° C.; $u_{max}$ $(CHCl_3)/cm^{-1}$ 3453, 3009, 2853, 1713, 1668, 1516, 1260, 1147, 1013; m/z (ESI) $C_{21}H_{25}Cl_2N_4O_3$ requires 451.1298, found $[M+H]^+$ 451.1301.

Intermediate 12: Benzyl 4-(piperidine-4-carbonyl)piperazine-1-carboxylate 12

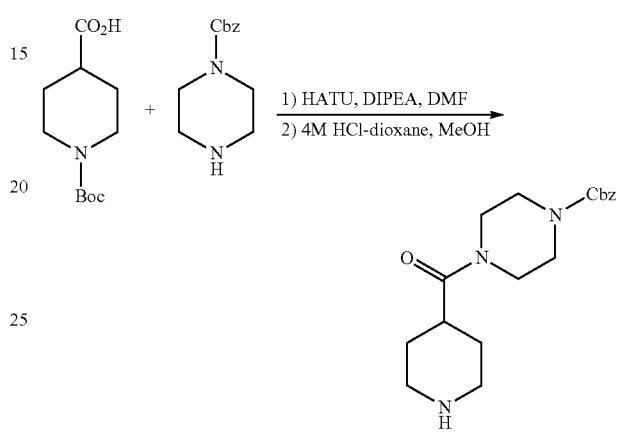

General procedure A was followed using N-Boc-isonipecotic acid (0.25 g, 1.1 mmol), HATU (0.46 g, 1.2 mmol), DIPEA (0.57 mL, 3.3 mmol), 1-Cbz-piperazine (0.21 mL, 1.1 mmol) and DMF (5 mL) to furnish the intermediate compound benzyl-4-(1-(tert-butoxycarbonyl)piperidine-4-carbonyl)piperazine-1-carboxylate as a white solid (339 mg, 72%), $u_{max}$ $(CHCl_3)/cm^{-1}$ 3014, 2863, 1688, 1644, 1427, 1367, 1205, 1168.

General procedure B was subsequently followed using benzyl-4-(1-(tert-butoxycarbonyl)piperidine-4-carbonyl) piperazine-1-carboxylate (330 mg), MeOH (10 mL) and a 4 M solution of hydrogen chloride in 1,4-dioxane (10 mL) to furnish the title compound 12 as a white solid (120 mg, 46%), $u_{max}$ $(CHCl_3)/cm^{-1}$ 3016, 2949, 1699, 1639, 1431, 1250, 1227, 1125, 1019; m/z (ESI) $C_{18}H_{26}N_3O_3$ requires 332.1969, found $[M+H]^+$ 332.1968.

Intermediate 13: benzyl-4-(1-(3,5-dichloropyridin-4-yl)piperidine-4-carbonyl)piperazine-1-carboxylate 13

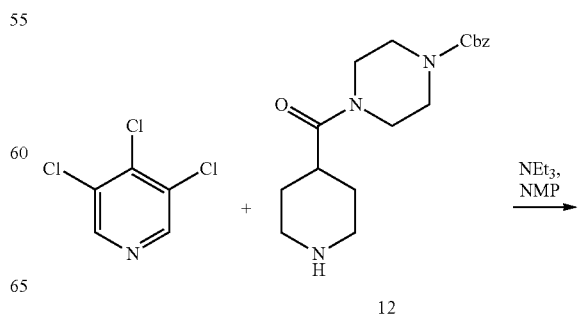

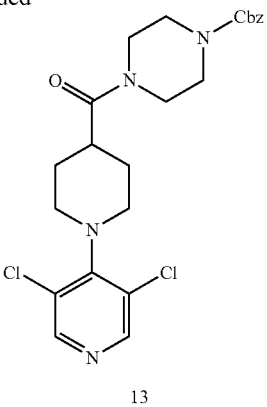

13

General procedure C (See Example 1) was followed using benzyl-4-(piperidine-4-carbonyl)piperazine-1-carboxylate 12 (0.11 g, 0.33 mmol), 3,4,5-trichloropyridine (61 mg, 0.33 mmol), NMP (2.5 mL) and triethylamine (93 μL, 0.66 mmol). The crude product was purified by flash column chromatography on silica gel (hexane, EtOAc, 1:1) to furnish the title compound 13 as a white solid (58 mg, 36%), $u_{max}$ (CHCl$_3$)/cm$^{-1}$ 3023, 1699, 1635, 1559, 1432, 1285, 1232, 1015; m/z (ESI) $C_{23}H_{27}Cl_2N_4O_3$ requires 477.1455, found [M+H]$^+$ 477.1457.

Intermediate 14: (R,S)-1-(3,5-dichloropyridin-4-yl) pyrrolidine-3-carbonitrile 14

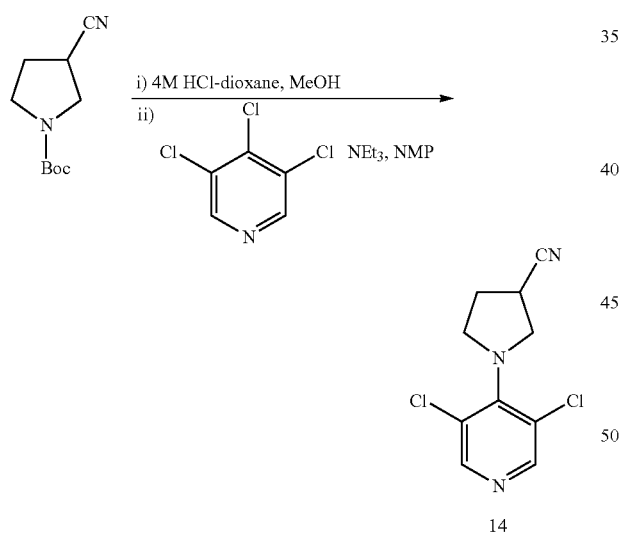

14 i) To a solution of (R,S)—N-Boc-3-cyanopyrrolidine (0.25 g, 1.3 mmol) in MeOH (5 mL) was added hydrogen chloride (5 mL of a 4 M solution in dioxane) and the mixture was stirred for 3 hours, after which time the solvent was removed under reduced pressure. The crude product was purified on an SCX-2 cartridge (MeOH followed by 0.5 M NH$_3$ in MeOH) to furnish (R,S)-3-cyanopyrrolidine as a colourless oil (136 mg, 100%).

ii) To a solution of (R,S)-3-cyanopyrrolidine (0.12 g, 1.3 mmol) and 3,4,5-trichloropyridine (0.23 g, 1.3 mmol), in NMP (8 mL) was added triethylamine (0.36 mL, 2.6 mmol). The mixture was heated at 220° C. for 60 min in a microwave reactor, poured into a saturated solution of sodium hydrogen carbonate (50 mL) and extracted with EtOAc (2×100 mL). The combined organic extracts were washed with water (50 mL), brine (50 mL), dried (MgSO$_4$) and concentrated under reduced pressure. The crude product was purified by flash column chromatography on silica gel (CH$_2$Cl$_2$, MeOH, 99:1) to furnish the title compound as a colourless oil (155 mg, 50%), $u_{max}$ (CHCl$_3$)/cm$^{-1}$ 3053, 2245, 1558, 1468, 1402; m/z (ESI) $C_{10}H_{10}Cl_2N_3$ requires 242.0246 found [M+H]$^+$ 242.0249.

Intermediate 15: (R,S)-3-(2-benzyloxycarbony-lamino-ethylcarbamoyl)pyrrolidine-1-carboxylic acid tert-butyl ester 15

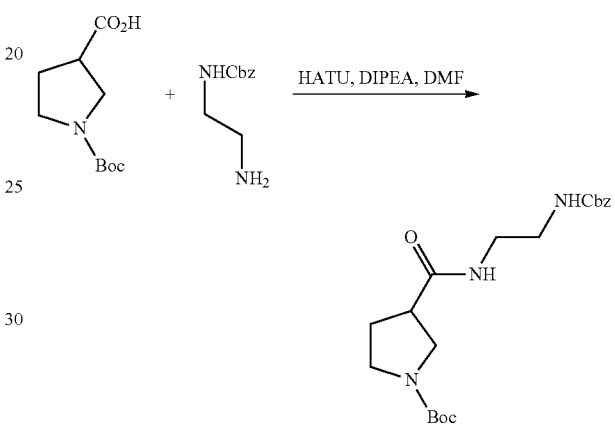

15

To a solution of (R,S)-1-Boc-pyrrolidine-3-carboxylic acid (0.22 g, 2.2 mmol), N—Z-ethylenediamine hydrochloride (0.50 g, 2.2 mmol) and HATU (0.82 g, 2.2 mmol) in DMF (15 mL) was added DIPEA (1.9 mL, 11 mmol) and the solution was stirred at r.t. for 16 h. The mixture was poured into a saturated solution of sodium hydrogen carbonate (50 mL) and extracted with EtOAc (2×40 mL). The combined organic extracts were washed with water (50 mL), a saturated solution of citric acid (50 mL), water (50 mL) and brine (50 mL), dried (MgSO$_4$) and concentrated under reduced pressure to furnish the title compound 15 as a colourless oil (0.43 g, 100%). This compound was used directly, without further purification.

Intermediate 16: {2-[(pyrrolidine-3-carbonyl)-amino]-ethyl}-carbamic acid benzyl ester 16

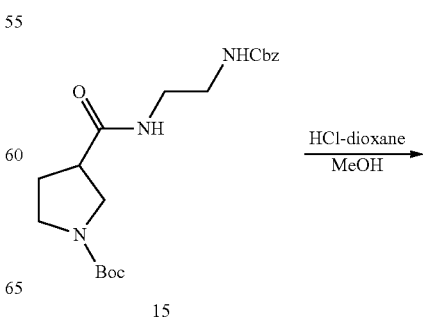

15

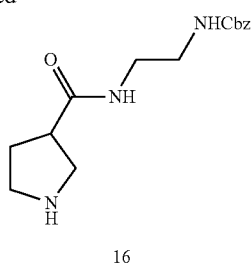

16

To a solution of (R,S)-3-(2-benzyloxycarbonylamino-ethylcarbamoyl)pyrrolidine-1-carboxylic acid tert-butyl ester 15 (430 mg, 1.10 mmol) in MeOH (5 mL) was added a 4 M solution of hydrogen chloride in 1,4-dioxane (5 mL). After stirring for 2 h, the mixture was concentrated under reduced pressure and the crude product was purified on an SCX-2 cartridge (MeOH followed by 0.5 M $NH_3$ in MeOH) to furnish the title compound as a white solid (260 mg, 81%), m.p. 129-131° C.; $u_{max}$ $(CHCl_3)/cm^{-1}$ 3451, 3014, 1714, 1663, 1517, 1227; m/z (ESI) $C_{15}H_{22}N_3O_3$ requires 292.1656, found $[M+H]^+$ 292.1654.

Intermediate 17: (R,S)-(2-{[1-(3,5-dichloro-pyridin-4-yl)-pyrrolidine-3-carbonyl]-amino}-ethyl)-carbamic acid benzyl ester 17

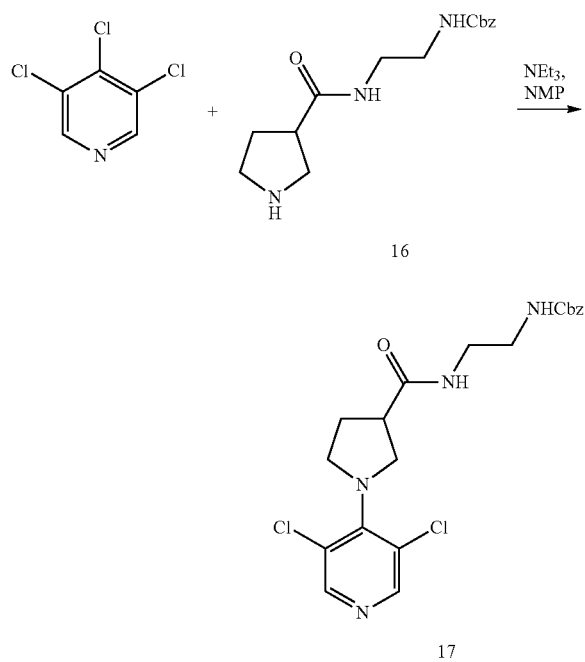

General procedure C was followed using 3,4,5-trichloro-pyridine (50 mg, 0.27 mmol), (R,S)-{2-[(pyrrolidine-3-carbonyl)-amino]-ethyl}-carbamic acid benzyl ester 16 (80 mg, 0.27 mmol), NMP (3 mL) and triethylamine (0.11 mL, 0.82 mmol). The crude product was purified by flash column chromatography on silica gel ($CH_2Cl_2$, MeOH, 99:1) to furnish the title compound as a white solid (61 mg, 51%), m.p. 148-150° C.; $u_{max}$ $(CHCl_3)/cm^{-1}$ 3028, 1716, 1668, 1515, 1464, 1221; m/z (ESI) $C_{20}H_{23}Cl_2N_4O_3$ requires 437.1141, found $[M+H]^+$ 437.1142.

Intermediate 18: 3,5-dibromo-4-chloropyridine 18

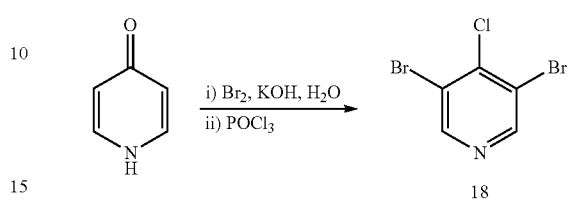

To a solution of 4-(1H)-pyridone (0.95 g, 10 mmol) and potassium hydroxide (1.1 g, 20 mmol) in water (20 mL) cooled to 0° C. was added bromine (3.2 g, 20 mmol). After stirring at this temperature for 75 min, the mixture was filtered and the cake was washed with washed with cold water (3×50 mL) and hexane (3×20 mL) to furnish 3,5-dibromo-4-(1H)-pyridone as a white solid (2.09 g, 83%).

To 3,5-dibromo-4-(1H)-pyridone (0.25 g, 1.0 mmol) was added $POCl_3$ (2 mL) and the mixture was heated at 100° C. for 2 h. The mixture was poured into ice/water (25 g) and basified by the addition of a saturated solution of sodium hydrogen carbonate. The mixture was extracted with $CH_2Cl_2$ (2×20 mL), the combined organic extracts were washed with brine (25 mL), dried ($MgSO_4$) and concentrated under reduced pressure to furnish the title compound as a white solid (275 mg, 100%), m.p. 101-103° C.; m/z 272 (100%, $[M+H]^+$);

Intermediate 19: (R,S)-(2-{[1-(3,5-dibromo-pyridin-4-yl)-pyrrolidine-3-carbonyl]-amino}-ethyl)-carbamic acid benzyl ester 19

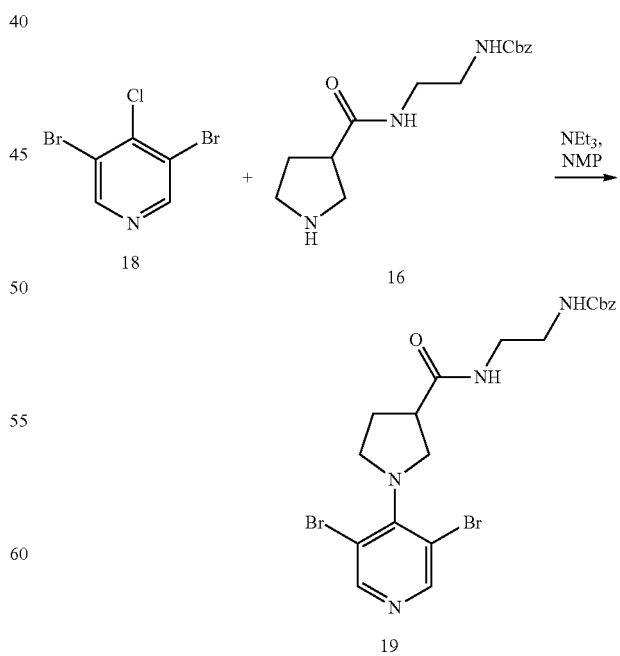

General procedure C (See Example 1) was followed using 3,5-dibromo-4-chloropyridine 18 (74 mg, 0.27 mmol), (R,S)-

3-(2-benzyloxycarbonylamino-ethylcarbamoyl)pyrrolidine-1-carboxylic acid tert-butyl ester 16 (80 mg, 0.27 mmol), NMP (3 mL) and triethylamine (0.11 mL, 0.82 mmol). The crude product was purified by flash column chromatography on silica gel (CH$_2$Cl$_2$, MeOH, 99:1) to furnish the title compound as a white solid (86 mg, 60%), m.p. 132-134° C.; u$_{max}$ (CHCl$_3$)/cm-1 3029, 3024, 1729, 1665, 1518, 1446, 1249, 1229, 1046, 1016; m/z (ESI) C$_{20}$H$_{22}$Br$_2$N$_4$NaO$_3$ requires 546.9951, found [M+Na]$^+$ 546.9946.

Intermediate 20: 4,5-dichloropyrimidine hydrochloride 20

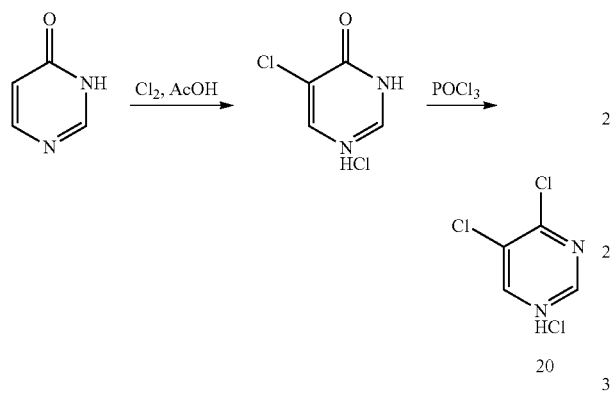

Chlorine was bubbled through a solution of 4-pyrimidone (1.9 g, 20 mmol) in glacial acetic acid (20 mL) for 1 h and the reaction mixture was stirred for a further 2 h. Chlorine was bubbled through the solution for a further 15 min and the mixture stirred for a further 90 min. The mixture was filtered and the cake was washed with hexane (3×25 mL) to furnish the title compound as a white solid (2.28 g).

A suspension of 5-chloropyrimidone hydrochloride (1.0 g, 6.0 mmol) in phosphorous oxychloride (4 mL) was heated at 90° C. for 90 min then cooled to room temperature and filtered. The crude product was purified by sublimation under reduced pressure to furnish the title compound 20 as a crystalline white solid (273 mg). This compound was unstable to air and was used immediately in the next step.

Intermediate 21: 5-bromo-4-chloropyrimidine hydrochloride 21

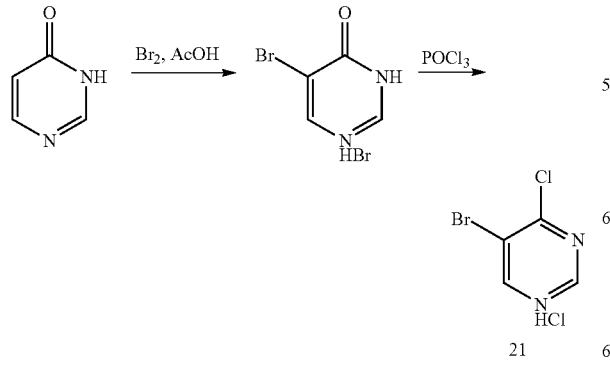

A solution of bromine (1.0 mL, 20 mmol) in glacial acetic acid (10 mL) was added over 15 min via cannula to a solution of 4-pyrimidone (1.9 g, 20 mmol) in glacial acetic acid (20 mL). After stirring for 5 h, the mixture was filtered and the cake was washed with hexane (2×20 mL) to furnish the title compound as a white solid (1.52 g).

A suspension of 5-bromopyrimidone hydrobromide (1.0 g, 3.9 mmol) in phosphorous oxychloride (4 mL) was heated at 90° C. for 1 h then cooled 0° C. The mixture was filtered, washed with POCl$_3$ (2×2 mL) to furnish the title compound as a cream solid (388 mg). This compound was unstable to air and was used immediately in the next step.

Intermediate 22: 4-chloro-5-methylpyrimidine hydrochloride 22

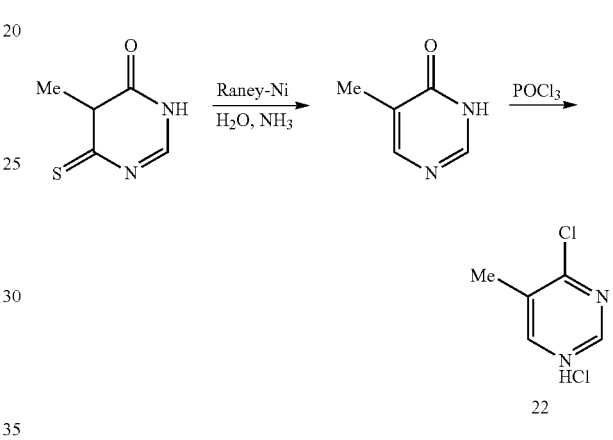

To a suspension of 4-hydroxy-2-mercapto-5-methylpyrimidine (1.0 g, 7.0 mmol) in water (50 mL) and ammonia (3 mL) was added a suspension of Raney Nickel in water (20 mL).

The mixture was heated at reflux for 16 h, then hot filtered through celite (10 g) and washed with water (3×25 mL). The filtrate was evaporated and the resultant solid was azeotroped with toluene (2×50 mL) to furnish a white solid (0.75 g, 97%).

A mixture of 5-methyl-3H-pyrimidin-4-one (0.60 g, 3.6 mmol) and phosphorous oxychloride (2.0 mL) was heated at 90° C. for 2.5 h. The mixture was evaporated to dryness under reduced pressure and the resultant solid was purified by sublimation under reduced pressure to furnish the title compound as a white solid. This compound was unstable to air and was used immediately in the next step.

Intermediate 23: 1-(3,5-dichloropyridin-4-yl)piperidine-4-carboxamide 23

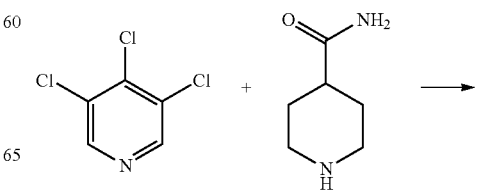

-continued

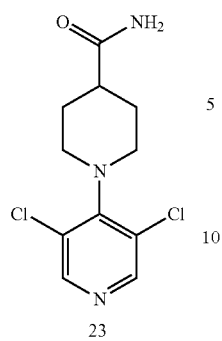

23

General procedure C (See Example 1) was followed using isonipecotamide (380 mg, 3.0 mmol), 3,4,5-trichloropyridine (600 mg, 3.3 mmol), triethylamine (0.84 mL, 6.0 mmol) and NMP (18 mL). The crude product was purified by flash column chromatography on silica gel (CH$_2$Cl$_2$/EtOH, 95:5-91:9) to furnish the title compound as a white solid (0.676 g, 83%); LC-MS (ESI, 4 min) R$_t$ 1.46 min, m/z 274 (100%, [M+H]$^+$); m/z (ESI) C$_{11}$H$_{13}$N$_3$OCl$_2$ requires 273.0436, found [M+H]$^+$ 273.0446.

Intermediate 24: 1-(3,5-dichloropyridin-4-yl)piperidine-4-carbothioamide 24

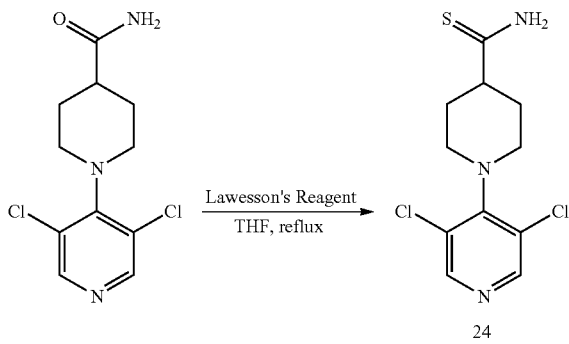 [SMILES: NC(=O)C1CCN(c2c(Cl)cncc2Cl)CC1 ; NC(=S)C1CCN(c2c(Cl)cncc2Cl)CC1]

24

To a solution of 1-(3,5-dichloropyridin-4-yl)piperidine-4-carboxamide 23 (40 mg, 0.15 mmol) in THF (2 mL) was added Lawesson's reagent (71 mg, 0.18 mmol) and the mixture was heated at reflux for 2.5 h. After cooling to r.t. the mixture was poured into a saturated solution of sodium hydrogen carbonate (20 mL) and extracted with EtOAc (2×20 mL). The combined organic extracts were washed with water (20 mL), brine (20 mL), dried (MgSO$_4$) and concentrated under reduced pressure. The crude product was purified by flash column chromatography on silica gel (CH$_2$Cl$_2$, MeOH, 99:1) to furnish the title compound as a white solid (21 mg, 40%), m/z (ESI) C$_{11}$H$_{14}$Cl$_2$N$_2$S requires 290.0280 found [M+H]$^+$ 290.0280.

Example 1

1-(3,5-dichloropyridin-4-yl)-N-methylpiperidine-4-carboxamide E1

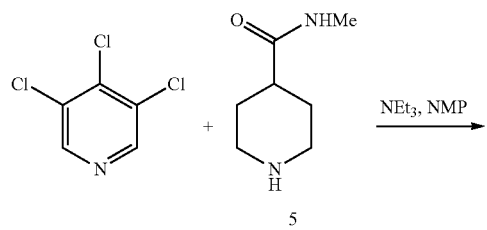

-continued

E1

General Procedure C

To a solution of N-methylpiperidine-4-carboxamide 5 (26 mg, 0.18 mmol) and 3,4,5-trichloropyridine (33 mg, 0.18 mmol) in NMP (1.5 mL) was added triethylamine (76 μL, 0.54 mmol). The mixture was heated in a microwave reactor at 220° C. for 60 min, cooled to r.t. and then poured into a saturated solution of sodium hydrogen carbonate (50 mL). The solution was extracted with EtOAc (2×25 mL), the combined organic extracts were washed with water (50 mL), brine (50 mL), dried (MgSO$_4$) and the solvent was removed under reduced pressure. The crude product was purified by flash column chromatography on silica gel (hexane/EtOAc, 1:1) to furnish the title compound as a white solid (46 mg, 88%), m.p. 175-177° C.; u$_{max}$ (CHCl$_3$)/cm$^{-1}$ 3462, 3006, 2853, 1665, 1558, 1385, 1146, 1096; m/z (ESI) C$_{12}$H$_{16}$Cl$_2$N$_3$O requires 288.0665, found [M+H]$^+$288.0664.

Example 2

1-(3,5-dichloropyridin-4-yl)-N,N-dimethylpiperidine-4-carboxamide E2

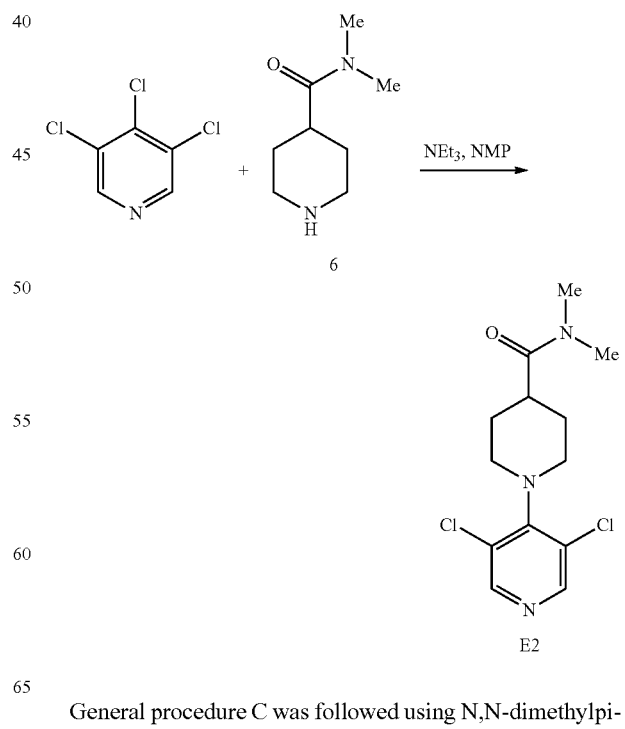

E2

General procedure C was followed using N,N-dimethylpiperidine-4-carboxamide 6 (43 mg, 0.27 mmol), 3,4,5-trichloropyridine (50 mg, 0.27 mmol), triethylamine (76 μL, 0.54 mmol) and NMP (1.5 mL). The crude product was purified by flash column chromatography on silica gel (hexane/EtOAc, 1:1) to furnish the title compound as a white solid (66 mg, 80%), m.p. 120-122° C.; $u_{max}$ (CHCl$_3$)/cm$^{-1}$ 3026, 2850, 1631, 1559, 1140, 1092, 934; m/z (ESI) C$_{13}$H$_{18}$Cl$_2$N$_3$O requires 302.0821, found [M+H]$^+$ 302.0823.

Example 3

(1-(3,5-dichloropyridin-4-yl)piperidin-4-yl)(morpholino) methanone E3

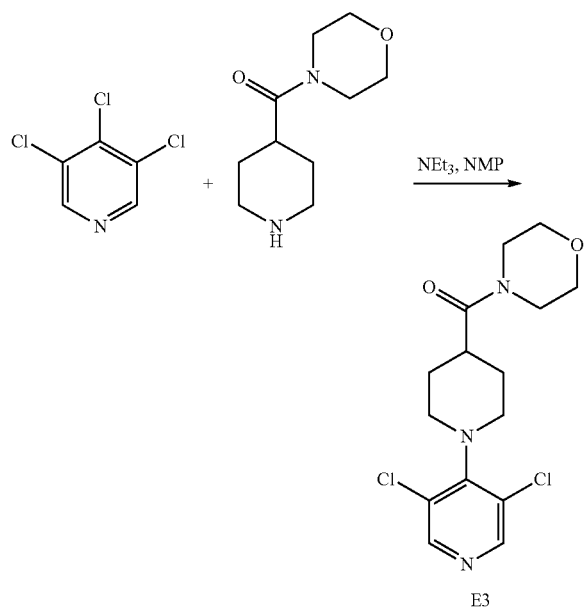

General procedure C was followed using morpholino(piperidin-4-yl)methanone (21 mg, 0.12 mmol), 3,4,5-trichloropyridine (23 mg, 0.12 mmol), triethylamine (32 μL, 0.23 mmol) and NMP (1 mL). The crude product was purified by flash column chromatography on silica gel (hexane/EtOAc, 1:1) to furnish the title compound as a white solid (15 mg, 35%), m.p. 172-174° C.; $u_{max}$ (CHCl$_3$)/cm$^{-1}$ 3006, 2858, 1632, 1559, 1448, 1116, 1020; m/z (ESI) C$_{15}$H$_{20}$Cl$_2$N$_3$O$_2$ requires 344.0927, found [M+H]$^+$ 344.0929.

Example 4

1-(3-chloro-5-(3,4-dimethoxyphenyl)pyridin-4-yl)piperidine-4-carboxamide E4

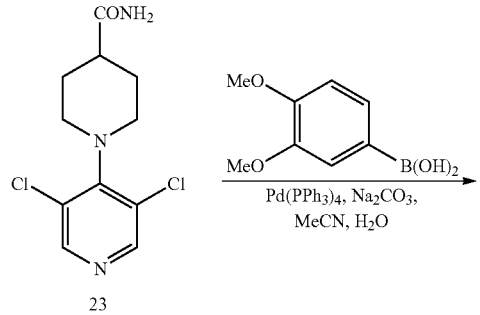

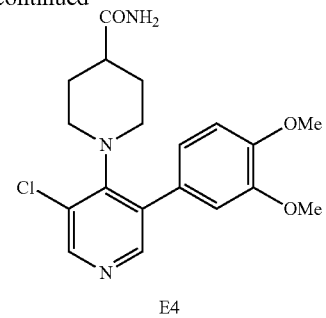

General Procedure D

To a mixture of 1-(3,5-dichloropyridin-4-yl)piperidine-4-carboxamide 23 (24 mg, 0.088 mmol), 3,4-diimethoxyphenyllboronic acid (19 mg, 0.11 mmol), and tetrakis (triphenylphosphine)palladium(0) (5 mg, 5 mol %) in acetonitrile (1 mL) was added a 0.5 M aqueous solution of sodium carbonate (0.25 mL, 0.12 mmol). The mixture was heated at 150° C. in a microwave reactor for 45 min, then cooled to r.t. and purified on an SCX-2 cartridge (MeOH followed by 0.5 M NH$_3$ in MeOH). The crude product was purified by preparative tlc on silica gel (CH$_2$Cl$_2$, MeOH, 10:1) to give impure title compound (7 mg). Further purification by preparative hplc (H$_2$O, MeCN, 90:10-10:90, 30 min) furnished the title compound as a white solid, LC-MS (ESI, 3.5 min) R$_t$ 1.60 min, m/z 376 (100%, [M+H]$^+$); m/z (ESI) C$_{19}$H$_{23}$ClN$_3$O$_3$ requires 376.1428 found [M+H]$^+$ 376.1421.

Example 5

1-(3,5-dichloropyridin-4-yl)-N-(2-(3,5-dichloropyridin-4-ylamino)ethyl)piperidine-4-carboxamide E5

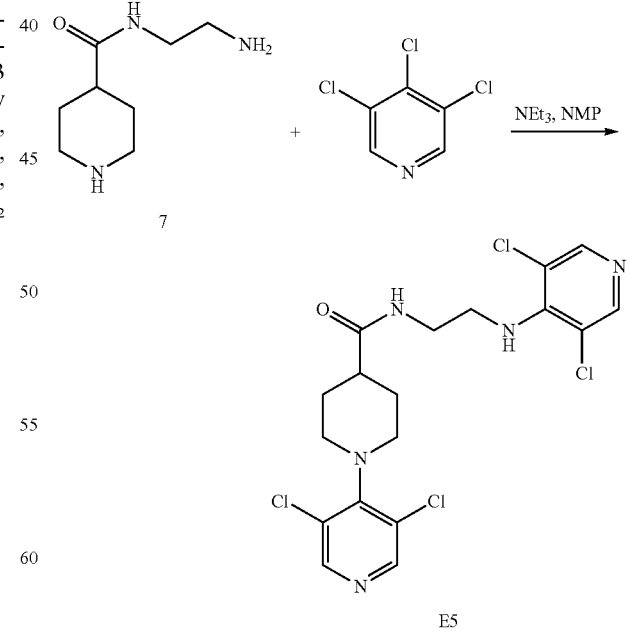

General procedure C was followed using benzyl-N-(amino-ethyl)piperidine-4-carboxamide 7 (47 mg, 0.27 mmol), 3,4,5-trichloropyridine (50 mg, 0.27 mmol), triethylamine (76 μL, 0.54 mmol) and NMP (1.5 mL). The crude product was purified by flash column chromatography on silica gel (hexane/EtOAc, 1:1) to furnish the title compound as a white solid (81 mg, 64%), m.p. 157-159° C.; u$_{max}$ (CHCl$_3$)/cm$^{-1}$ 3013, 1670, 1574, 1510, 1231, 1092; m/z (ESI) C$_{18}$H$_{20}$Cl$_4$N$_5$O requires 462.0417, found [M+H]$^+$ 462.0421.

Example 6

4-(3-methylpyridin-4-yl)cyclohexanecarboxamide E6

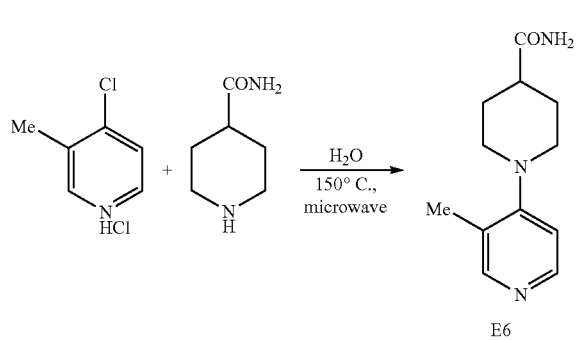

A solution of 4-chloro-3-methylpyridine hydrochloride (50 mg, 30 mmol) and isonipecotamide (0.12 g, 0.91 mmol) in water (1 mL) was heated at 100° C. for 45 min in a microwave reactor. The reaction mixture was cooled to 0° C. and the mixture was filtered and washed with Et$_2$O (2×10 mL) to furnish the title compound as a colourless, crystalline solid (33 mg, 49%), m.p. 175-177° C.; m/z (ESI) C$_{12}$H$_{18}$CN$_3$O requires 220.1444, found [M+H]$^+$ 220.1445.

Example 7

4-(4-carbamoylpiperidin-1-yl)-3,5-dichloropyridine 1-oxide E7

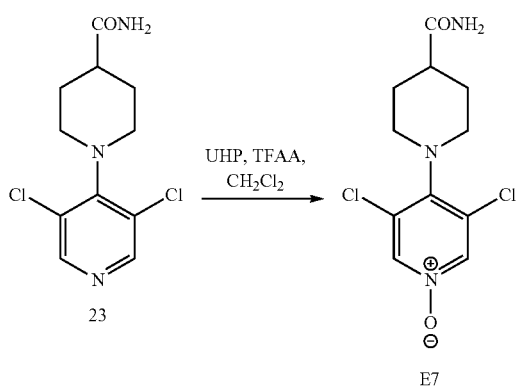 [SMILES: NC(=O)C1CCN(c2c(Cl)cncc2Cl)CC1 ; NC(=O)C1CCN(c2c(Cl)c[n+]([O-])cc2Cl)CC1]

To a solution of 1-(3,5-dichloropyridin-4-yl)piperidine-4-carboxamide 23 (100 mg, 0.36 mmol) and hydrogen peroxide.urea complex (72 mg, 0.77 mmol) in CH$_2$Cl$_2$ (2 mL) cooled to 0° C. was added trifluoroacetic anhydride (0.10 mL, 0.73 mmol). After 30 min the solution was warmed to r.t., after a further 16 hours a saturated solution of Na$_2$S$_2$O$_5$ (10 mL) was added. The mixture was extracted with CH$_2$Cl$_2$ (2×20 mL), the combined organic extracts were washed with a saturated solution of NaHCO$_3$ (20 mL), brine (20 mL), dried (MgSO$_4$) and the solvent removed under reduced pressure. The crude product was purified by flash column chromatography on silica gel (CH$_2$Cl$_2$/MeOH, 98:2) to furnish the title compound as a white solid (20 mg, 19%), m.p. 130-133° C.; u$_{max}$ (CHCl$_3$)/cm$^{-1}$ 3026. 2855, 1724, 1452, 1273, 1107.

Example 8

(4-(3,5-dichloropyridin-4-yl)piperazin-1-yl)(phenyl)methanone E8

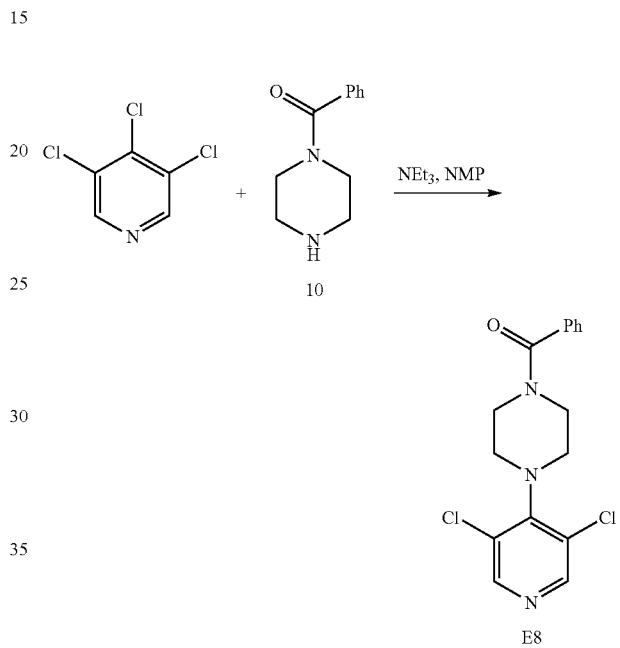

General procedure C was followed using 4-benzoylpiperazine 10 (47 mg, 0.25 mmol), 3,4,5-trichloropyridine (72 mg, 0.39 mmol), triethylamine (0.11 mL, 0.78 mmol) and NMP (1.5 mL). The crude product was purified by flash column chromatography on silica gel (hexane/EtOAc, 1:1) to furnish the title compound as a white solid (19 mg, 23%), m.p. 132-134° C.; u$_{max}$ (CHCl$_3$)/cm$^{-1}$ 3005, 1627, 1435, 1286, 1153, 1010; m/z (ESI) C$_{16}$H$_{16}$Cl$_2$N$_3$O requires 336.0665, found [M+H]$^+$ 336.0661.

Example 9

1-(4-(3,5-dichloropyridin-4-yl)piperazin-1-yl)ethanone E9

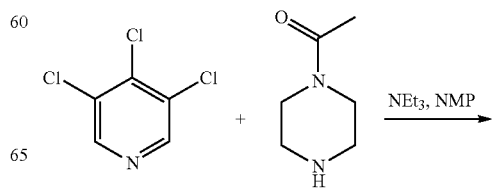

-continued

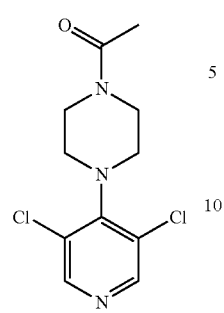

E9

General procedure C was followed using acetylpiperazine (35 mg, 0.27 mmol), 3,4,5-trichloropyridine (50 mg, 0.27 mmol), triethylamine (0.76 µL, 0.54 mmol) and NMP (1.5 mL). The crude product was purified by flash column chromatography on silica gel (hexane/EtOAc, 1:1) to furnish the title compound as a white solid (18 mg, 24%), m.p. 144-146° C.; $u_{max}$ (CHCl$_3$)/cm$^{-1}$ 3008, 2909, 2856, 1638, 1558, 1470, 1441, 1282, 1240, 1152, 1098; m/z (ESI) $C_{11}H_{14}Cl_2N_3O$ requires 274.0508, found [M+H]$^+$ 274.0513.

Example 10

1-(3,5-dichloropyridin-4-yl)-4-methylpiperazine E10

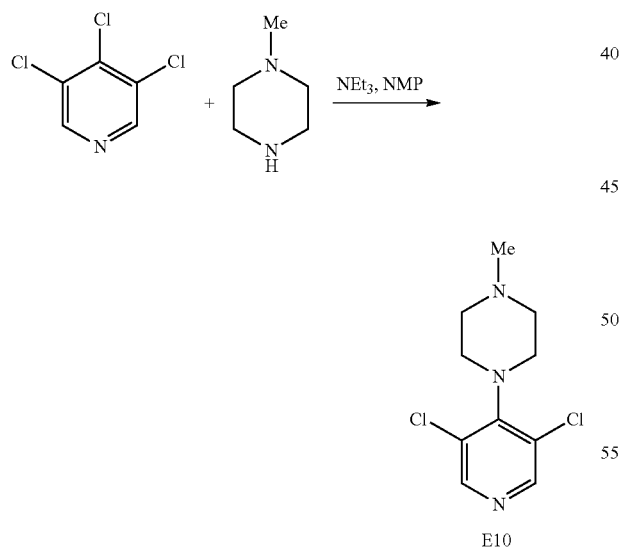

E10

General procedure C was followed using N-methylpiperazine (27 mg, 0.27 mmol), 3,4,5-trichloropyridine (50 mg, 0.27 mmol), triethylamine (0.76 µL, 0.54 mmol) and NMP (1.5 mL). The crude product was purified by flash column chromatography on silica gel (hexane/EtOAc, 1:1) to furnish the title compound as a colourless oil (44 mg, 65%), $u_{max}$ (CHCl$_3$)/cm$^{-1}$ 2942, 2849, 2803, 1558, 1449, 1289, 1151; m/z (ESI) $C_{10}H_{14}Cl_2N_3$ requires 246.0559, found [M+H]$^+$ 246.0560.

Example 11

1-(3,5-dichloropyridin-4-yl)-4-ethylpiperazine E11

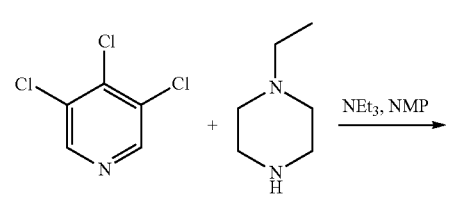

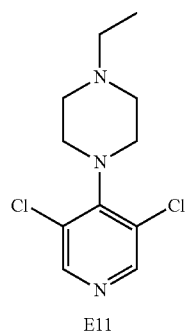

E11

General procedure C was followed using N-ethylpiperazine (31 mg, 0.27 mmol), 3,4,5-trichloropyridine (50 mg, 0.27 mmol), triethylamine (0.76 µL, 0.54 mmol) and NMP (1.5 mL). The crude product was purified by flash column chromatography on silica gel (hexane/EtOAc, 1:1) to furnish the title compound as a colourless oil (47 mg, 66%), $u_{max}$ (CHCl$_3$)/cm$^{-1}$ 2975, 2820, 1559, 1448, 1245, 1151, 957; m/z (ESI) $C_{11}H_{16}Cl_2N_3$ requires 260.0716, found [M+H]$^+$ 260.0719.

Example 12

1-(3-chloropyridin-4-yl)piperidine-4-carboxamide E12

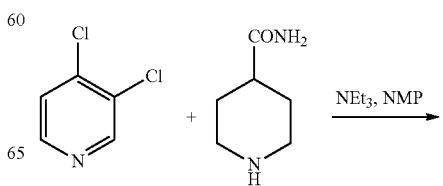

-continued

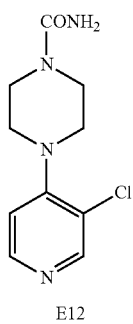

E12

General procedure C was followed using isonipecotamide (43 mg, 0.34 mmol), 3,4,dichloropyridine (50 mg, 0.34 mmol), triethylamine (0.14 mL, 1.0 mmol) and NMP (1.5 mL). The crude product was purified by flash column chromatography on silica gel (hexane/EtOAc, 1:1) to furnish the title compound as a colourless oil (18 mg, 22%), m.p. 210-212° C.; $u_{max}$ (CHCl$_3$)/cm$^{-1}$ 2360, 2342, 1653, 1581 1382, 1223, 1135, 1041; m/z (ESI) $C_{11}H_{15}ClN_3O$ requires 240.0898, found [M+H]$^+$ 240.0899.

Example 13

N-(2-aminoethyl)-1-(3,5-dichloropyridin-4-yl)piperidine-4-carboxamide E13

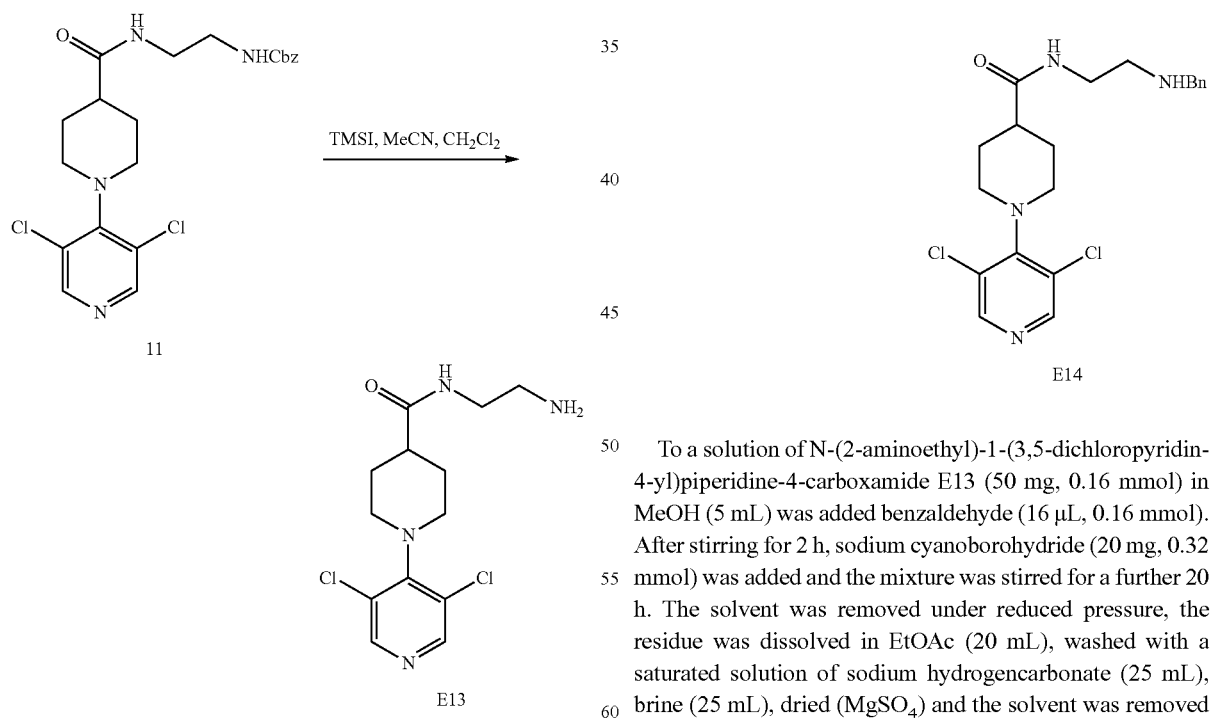

To a solution of benzyl-2-(1-(3,5-dichloropyridin-4-yl)piperidine-4-carboxamido) ethylcarbamate 11 (0.45 g, 1.0 mmol) in acetonitrile and dichloromethane (1:1 mixture, 40 mL), cooled to 0° C. was added trimethylsilyl iodide (0.57 mL, 4.0 mmol). After stirring for 60 min, the solvent was removed under reduced pressure and the crude product was purified by flash column chromatography on silica gel (CH$_2$Cl$_2$/MeOH, 98:2) to furnish the title compound as a colourless oil (193 mg, 61%), $u_{max}$ (CHCl$_3$)/cm$^{-1}$ 3002, 2853, 1663, 1559, 1512, 1457, 1264, 1146; m/z (ESI) $C_{13}H_{19}Cl_2N_4O$ requires 317.0930, found [M+H]$^+$ 317.0928.

Example 14

N-(2-(benzylamino)ethyl)-1-(3,5-dichloropyridin-4-yl)piperidine-4-carboxamide E14

To a solution of N-(2-aminoethyl)-1-(3,5-dichloropyridin-4-yl)piperidine-4-carboxamide E13 (50 mg, 0.16 mmol) in MeOH (5 mL) was added benzaldehyde (16 µL, 0.16 mmol). After stirring for 2 h, sodium cyanoborohydride (20 mg, 0.32 mmol) was added and the mixture was stirred for a further 20 h. The solvent was removed under reduced pressure, the residue was dissolved in EtOAc (20 mL), washed with a saturated solution of sodium hydrogencarbonate (25 mL), brine (25 mL), dried (MgSO$_4$) and the solvent was removed under reduced pressure. The crude product was purified by preparative tlc on silica gel (CH$_2$Cl$_2$, MeOH, 9:1) to furnish the title compound as a colourless oil (19 mg, 30%), $u_{max}$ (CHCl$_3$)/cm$^{-1}$ 3015, 2850, 1659, 1558, 1512, 1236, 1146, 1036, 934; m/z (ESI) $C_{20}H_{25}Cl_2N_4O$ requires 407.1400, found [M+H]$^+$ 407.1401.

Example 15

1-(3,5-dichloropyridin-4-yl)-N-(2-(4-methoxybenzylamino)ethyl)piperidine-4-carboxamide E15

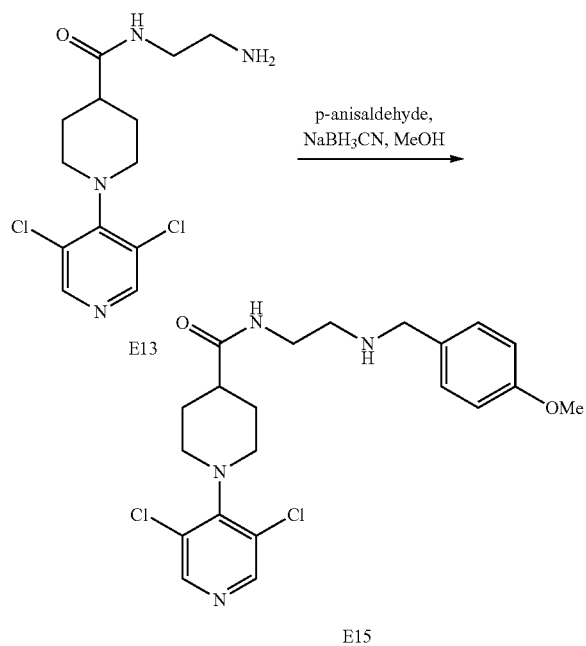

To a solution of N-(2-aminoethyl)-1-(3,5-dichloropyridin-4-yl)piperidine-4-carboxamide E13 (50 mg, 0.16 mmol) in MeOH (5 mL) was added anisaldehyde (19 μL, 0.16 mmol). After stirring for 2 h, sodium cyanoborohydride (20 mg, 0.32 mmol) was added and the mixture was stirred for a further 20 h. The solvent was removed under reduced pressure, the residue was dissolved in EtOAc (20 mL), washed with a saturated solution of sodium hydrogencarbonate (25 mL), brine (25 mL), dried (MgSO$_4$) and the solvent was removed under reduced pressure. The crude product was purified by preparative tlc on silica gel (CH$_2$Cl$_2$, MeOH, 9:1) to furnish the title compound as a colourless oil (13 mg, 19%), u$_{max}$ (CHCl$_3$)/cm$^{-1}$ 3008, 2839, 1660, 1513, 1249, 1174, 1036; m/z (ESI) C$_{21}$H$_{27}$Cl$_2$N$_4$O$_2$ requires 437.1506, found [M+H]$^+$ 437.1508.

Example 16

N-(2-(cyclohexylmethylamino)ethyl)-1-(3,5-dichloropyridin-4-yl)piperidine-4-carboxamide E16

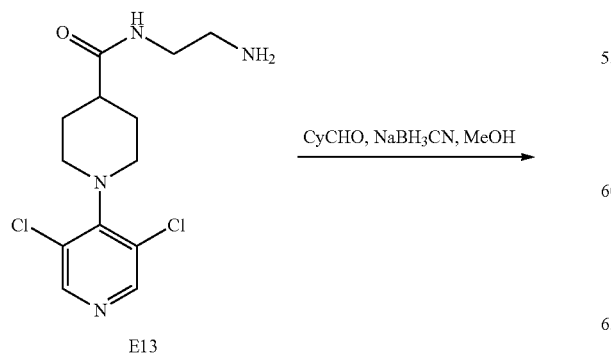

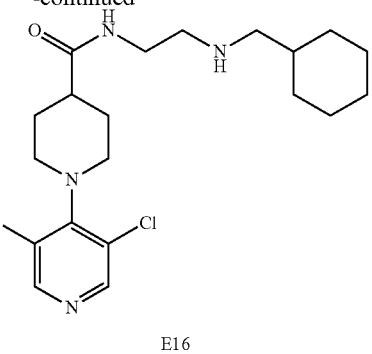

To a solution of N-(2-aminoethyl)-1-(3,5-dichloropyridin-4-yl)piperidine-4-carboxamide E13 (50 mg, 0.16 mmol) in MeOH (5 mL) was added cyclohexanecarbaldehyde (19 μL, 0.16 mmol). After stirring for 2 h, sodium cyanoborohydride (20 mg, 0.32 mmol) was added and the mixture was stirred for a further 16 h. The solvent was removed under reduced pressure, the residue was dissolved in EtOAc (20 mL), washed with a saturated solution of sodium hydrogencarbonate (25 mL), brine (25 mL), dried (MgSO$_4$) and the solvent was removed under reduced pressure. The crude product was purified by preparative tlc on silica gel (CH$_2$Cl$_2$, MeOH, 9:1) to furnish the title compound as a white solid (15 mg, 23%), m.p. 174-177° C.; u$_{max}$ (CHCl$_3$)/cm$^{-1}$ 2932, 2856, 1665, 1558, 1457, 1236, 1146, 1037; m/z (ESI) C$_{20}$H$_{31}$Cl2$_2$N$_4$O requires 413.1869, found [M+H]$^+$ 413.1875.

Example 17

N-(2-(dibenzylamino)ethyl)-1-(3,5-dichloropyridin-4-yl)piperidine-4-carboxamide E17

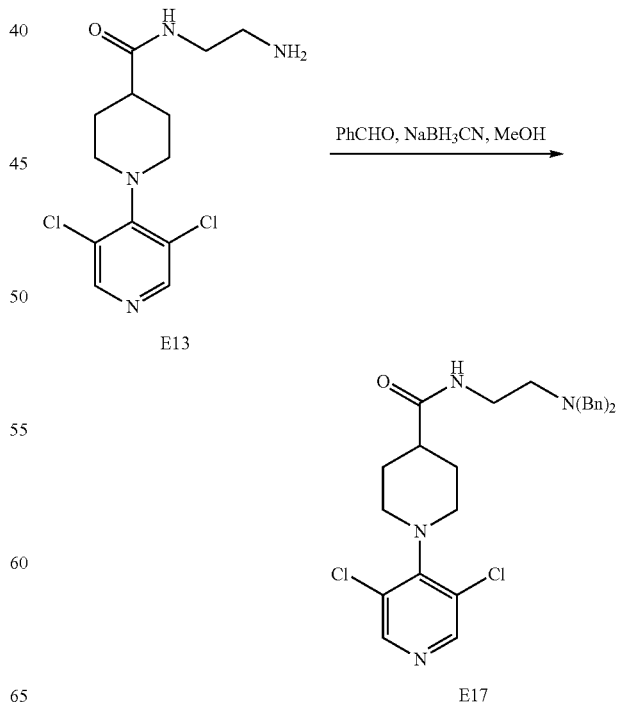

To a solution of N-(2-aminoethyl)-1-(3,5-dichloropyridin-4-yl)piperidine-4-carboxamide E13 (20 mg, 0.060 mmol) in MeOH (2 mL) was added benzaldehyde (19 μL, 0.19 mmol). After stirring for 45 min, sodium cyanoborohydride (12 mg, 0.19 mmol) was added and the mixture was stirred for a further 16 h. The solvent was removed under reduced pressure, the residue was dissolved in EtOAc (20 mL), washed with a saturated solution of sodium hydrogencarbonate (25 mL), brine (25 mL), dried (MgSO$_4$) and the solvent was removed under reduced pressure. The crude product was purified by preparative tlc on silica gel (CH$_2$Cl$_2$, MeOH, 9:1) to furnish the title compound as a white solid (14 mg, 54%), m.p. 147-149° C.; u$_{max}$ (CHCl$_3$)/cm$^{-1}$ 3007, 2837, 1658, 1558, 1509, 1457, 1146; m/z (ESI) C$_{27}$H$_{31}$Cl$_2$N$_4$O requires 497.1869, found [M+H]$^+$ 497.1872.

Example 18

N-(2-(bis(cyclohexylmethyl)amino)ethyl)-1-(3,5-dichloropyridin-4-yl)piperidine-4-carboxamide E18

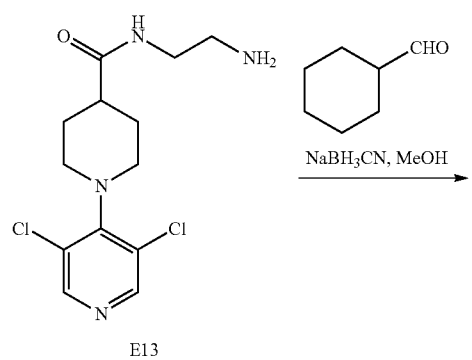

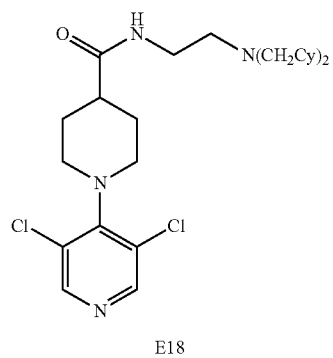

To a solution of N-(2-aminoethyl)-1-(3,5-dichloropyridin-4-yl)piperidine-4-carboxamide E13 (20 mg, 0.060 mmol) in MeOH (2 mL) was added cyclohexanecarbaldehyde (23 μL, 0.19 mmol). After stirring for 30 min, sodium cyanoborohydride (12 mg, 0.19 mmol) was added and the mixture was stirred for a further 16 h. The solvent was removed under reduced pressure, the residue was dissolved in EtOAc (20 mL), washed with a saturated solution of sodium hydrogencarbonate (25 mL), brine (25 mL), dried (MgSO$_4$) and the solvent was removed under reduced pressure. The crude product was purified by preparative tlc on silica gel (CH$_2$Cl$_2$, MeOH, 9:1) to furnish the title compound as a white solid (28 mg, 87%), m.p. 236-238° C.; u$_{max}$ (CHCl$_3$)/cm$^{-1}$ 2926, 2852, 1656, 1510, 1384, 1099; m/z (ESI) C$_{27}$H$_{42}$Cl$_2$N$_4$O requires 509.2808, found [M+H]$^+$ 509.2808.

Example 19

N-(2-benzamidoethyl)-1-(3,5-dichloropyridin-4-yl)piperidine-4-carboxamide E19

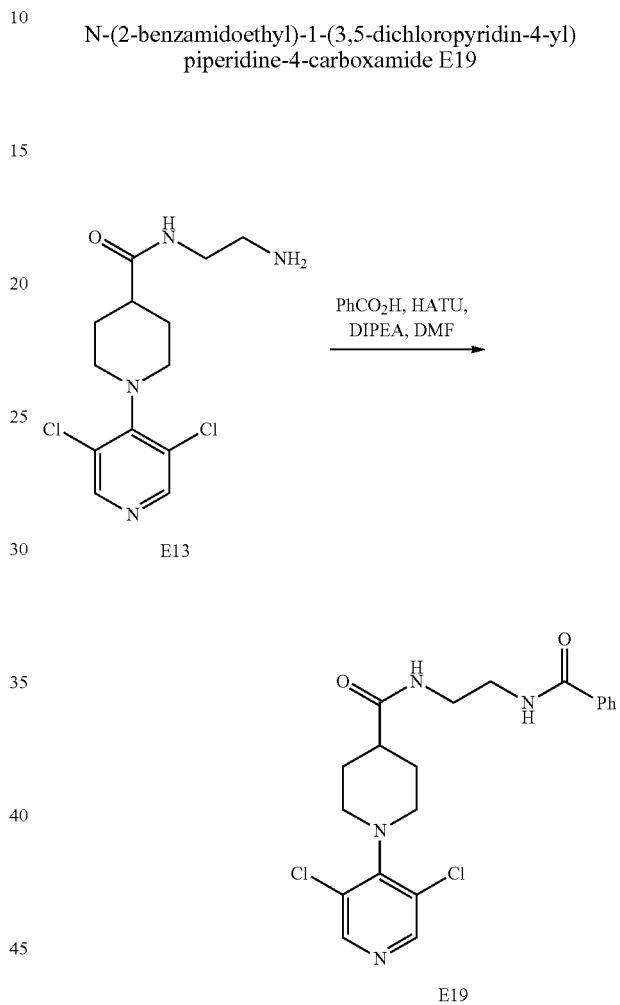

To a solution of N-(2-aminoethyl)-1-(3,5-dichloropyridin-4-yl)piperidine-4-carboxamide E13 (50 mg, 0.16 mmol), benzoic acid (23 mg, 0.19 mmol) and HATU (72 mg, 0.19 mmol) in DMF (1 mL) was added DIPEA (82 μL, 0.47 mmol). After 16 h the mixture was poured into a saturated solution of sodium hydrogen carbonate (50 mL) and extracted with EtOAc (2×25 mL). The combined organic extracts were washed with water (50 mL), a saturated solution of citric acid (50 mL) water (50 mL) and brine (50 mL), dried (MgSO$_4$) and concentrated under reduced pressure. The crude product was purified by preparative tlc on silica gel (CH$_2$Cl$_2$, MeOH, 9:1) to furnish the title compound as a white solid (24 mg, 36%), m.p. 209-211° C.; u$_{max}$ (CHCl$_3$)/cm$^{-1}$ 3029, 3006, 1656, 1523, 1385, 1228, 1017; m/z (ESI) C$_{20}$H$_{22}$Cl$_2$N$_4$NaO$_2$ requires 443.1012, found [M+Na]$^+$ 443.1013.

Example 20

(1-(3,5-dichloropyridin-4-yl)piperidin-4-yl)(piperazin-1-yl)methanone E20

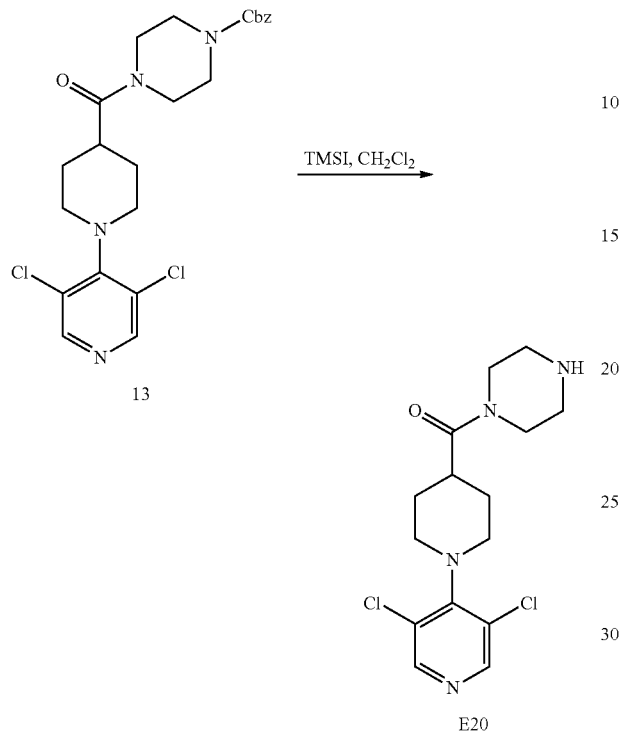

To a solution of benzyl-4-(1-(3,5-dichloropyridin-4-yl)piperidine-4-carbonyl)piperazine-1-carboxylate 13 (40 mg, 0.080 mmol) in DCM (1 mL), cooled to 0° C. was added trimethylsilyliodide (24 μL, 0.16 mmol) and the solution was stirred at this temperature for 90 min, after which time trimethylsilyl iodide (48 μL, 0.32 mmol) was added and the mixture warmed to room temperature. After stirring for a further 45 min, the solution was concentrated under reduced pressure and the crude product was purified on an SCX-2 cartridge (MeOH followed by 0.5 M $NH^3$ in MeOH) to furnish the title compound as a yellow solid (27 mg, 94%), m.p. 256-258° C.; m/z (ESI) $C_{15}H_{20}C_{12}N_4NaO$ requires 365.0906, found $[M+Na]^+$ 365.0909.

Example 21

1-(3,5-dichloropyridin-4-yl)pyrrolidine-3-carboxamide E21

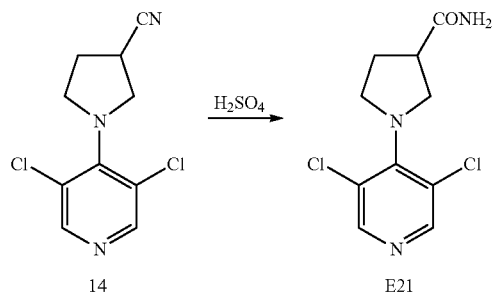

A solution of 1-(3,5-dichloropyridin-4-yl)pyrrolidine-3-carbonitrile 14 (83 mg, 0.34 mmol) in sulphuric acid (3 mL) was stirred for 90 min and then poured onto ice/water (100 g). The mixture was made basic by the addition of a 2 M solution of sodium hydroxide and extracted with EtOAc (2×50 mL). The combined organic extracts were washed with water (50 mL), brine (50 mL), dried ($MgSO_4$) and concentrated under reduced pressure, to furnish the title compound as a white solid (65 mg, 73%), m.p. 161-163° C.; $u_{max}$ ($CHCl_3$)/$cm^{-1}$ 3053, 2985, 1689, 1558, 1465; m/z (ESI) $C_{10}H_{12}Cl_2N_3O$ requires 260.0352 found $[M+H]^+$ 260.0355.

Example 22

1-(3,5-dibromopyridin-4-yl)pyrrolidine-3-carboxamide E22 and

Example 23

1-(3,5-dibromopyridin-4-yl)pyrrolidine-3-carbonitrile E23

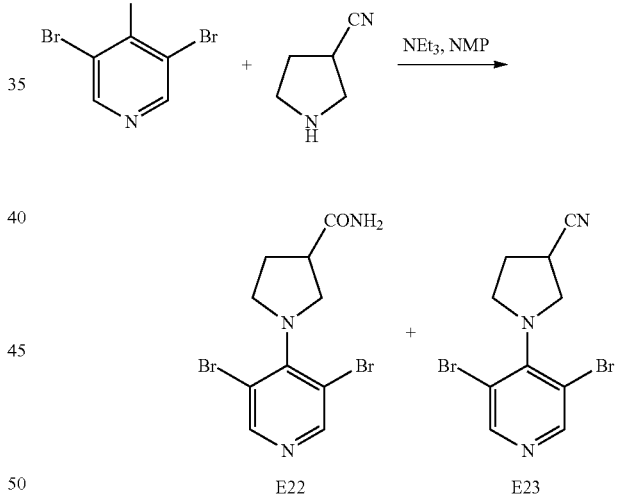

General procedure C was followed using 3,5-dibromo-4-chloropyridine (71 mg, 0.26 mmol), 3-cyanopyrrolidine (25 mg, 0.26 mmol), NMP (3 mL) and triethylamine (72 μL, 0.52 mmol). The crude product was purified by flash column chromatography on silica gel ($CH_2Cl_2$, MeOH, 99:1) to furnish the title compound E22 as a white solid (9 mg, 10%), m.p. 159-161° C.; $u_{max}$ ($CHCl_3$)/$cm^{-1}$ 3022, 3008, 1678, 1591, 1446, 1235; m/z (ESI) $C_{10}H_{12}Br_2N_3O$ requires 347.9342, found $[M+H]^+$ 347.9339.

Also isolated from the purification procedure was 1-(3,5-dibromopyridin-4-yl)pyrrolidine-3-carbonitrile E23 as a colourless oil (13 mg, 15%), $u_{max}$ ($CHCl_3$)/$cm^{-1}$ 3014, 2988, 2246, 1731m 1451m 1374, 1248, 1045, 1016; m/z (ESI) $C_{10}H_{10}Br_2N_3$ requires 329.9236, found $[M+H]^+$ 329.9238.

Example 24

(R,S)-1-(3,5-dichloro-pyridin-4-yl)-pyrrolidine-3-carboxylic acid (2-amino-ethyl)-amide E24

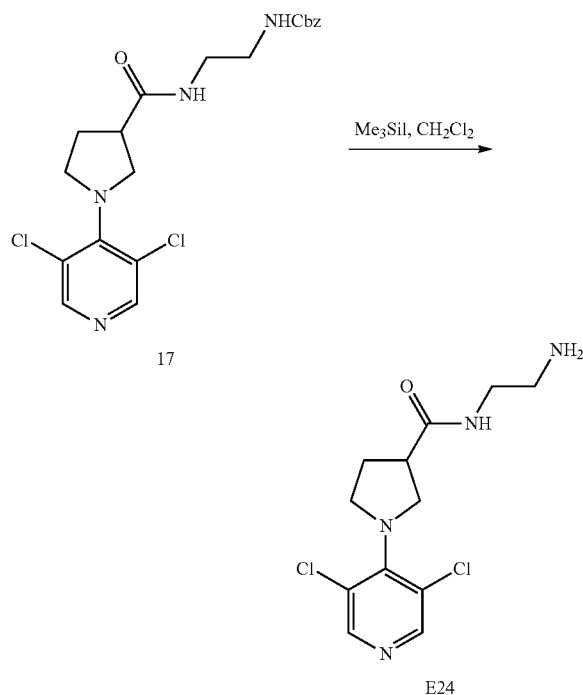

To a solution of (R,S)-(2-{[1-(3,5-dichloro-pyridin-4-yl)-pyrrolidine-3-carbonyl]-amino}-ethyl)-carbamic acid benzyl ester 17 (50 mg, 0.11 mmol) in dichloromethane (2 mL), cooled to 0° C., was added iodotrimethylsilane (66 µL, 0.46 mmol). After stirring at this temperature for 2 h, the solvent was removed under reduced pressure and the crude product was purified on an SCX-2 cartridge (MeOH followed by 0.5 M NH$_3$ in MeOH) to furnish the title compound as a colourless oil (16 mg, 46%), u$_{max}$ (CHCl$_3$)/cm$^{-1}$ 3014, 1731, 1664, 1559, 1519, 1465, 1248, 1046; m/z (ESI) C$_{12}$H$_{16}$Cl$_2$N$_4$NaO requires 325.0593, found [M+Na]$^+$ 325.0595.

Example 25

1-(3,5-dibromo-pyridin-4-yl)-pyrrolidine-3-carboxylic acid (2-amino-ethyl)-amide E25

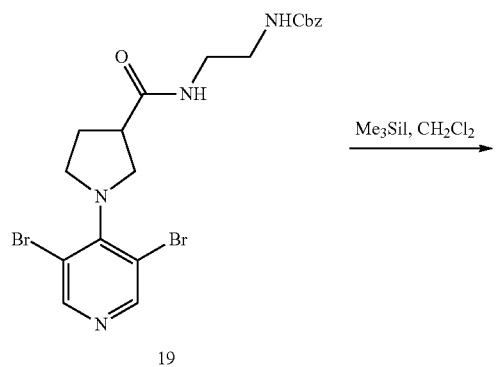

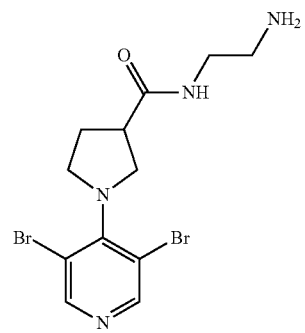

To a solution of benzyl-2-(1-(3,5-dibromopyridin-4-yl) pyrrolidine-3-carboxamido) ethylcarbamate 19 (65 mg, 0.12 mmol) in dichloromethane (2 mL), cooled to 0° C., was added iodotrimethylsilane (70 µL, 0.49 mmol). After stirring at this temperature for 2 h, the solvent was removed under reduced pressure and the crude product was purified on an SCX-2 cartridge (MeOH followed by 0.5 M NH$_3$ in MeOH) to furnish the title compound as a colourless oil (40 mg, 83%), u$_{max}$ (CHCl$_3$)/cm$^{-1}$ 3022, 2871, 1664, 1556, 1450, 1399; m/z (ESI) C$_{12}$H$_{16}$Br$_2$N$_4$NaO requires 412.9583, found [M+H]$^+$ 412.9582.

Example 26

4-(3,5-dimethylpyridin-4-yl)cyclohexanecarboxamide E26

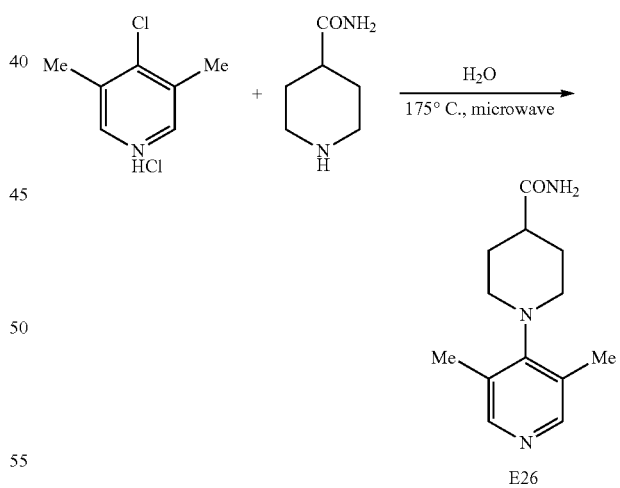

A solution of 4-chloro-3,5-dimethylpyridine hydrochloride (0.10 g, 0.56 mmol) and isonipecotamide (0.22 mg, 1.7 mmol) in water (1.5 mL) was heated at 175° C. for 60 min, in a microwave reactor. The mixture was poured into a saturated solution of sodium hydrogen carbonate (20 mL), extracted with EtOAc (2×20 mL). The combined organic extracts were dried (MgSO$_4$) and concentrated under reduced pressure. The crude product was purified by flash column chromatography on silica gel (CH$_2$Cl$_2$, MeOH, 95:5) to furnish the title compound as a white solid (5 mg, 4%), m/z 234 (100%, [M+H]⁺); m/z (ESI) $C_{13}H_{20}N_3O$ requires 234.1601 found [M+H]⁺ 234.1600.

Example 27

1-(3,5-dibromopyridin-4-yl)piperidine-4-carboxamide E27

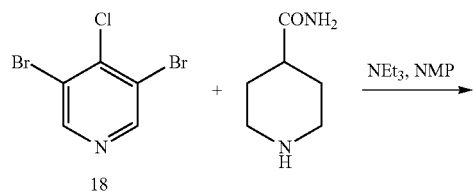

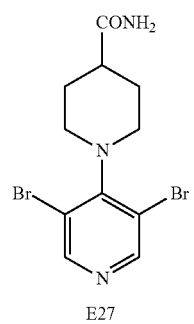

General procedure C was followed using 3,5-dibromo-4-chloropyridine 18 (50 mg, 0.18 mmol), isonipecotamide (24 mg, 0.18 mmol), NMP (2 mL) and triethylamine (51 μL, 0.37 mmol). The crude product was purified by preparative tlc on silica gel (CH₂Cl₂, MeOH, 9:1) to furnish the title compound as a pale yellow solid (29 mg, 43%), m.p. 158-160° C.; u$_{max}$ (CHCl₃)/cm⁻¹ 3053, 2985, 1687, 1591; m/z (ESI) $C_{11}H_{14}Br_2N_3O$ requires 361.9498 found [M+H]⁺ 361.9500.

Example 28

1-(5-chloropyrimidin-4-yl)piperidine-4-carboxamide E28

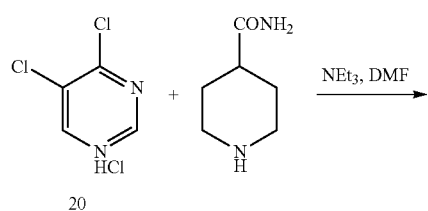

-continued

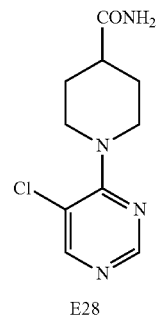

To a solution of 4,5-dichloropyrimidne hydrochloride 20 (0.20 g, 1.1 mmol) in DMF (4 mL) was added triethylamine (1.5 mL, 10 mmol). After stirring for 30 min, a solution of isonipecotamide (0.42 mg, 3.3 mmol) in DMF (4 mL) was added and the mixture was stirred at r.t. for a further 16 h. The mixture was poured into a saturated solution of sodium hydrogen carbonate (50 mL) and extracted with EtOAc (2×25 mL). The combined organic extracts were washed with water (25 mL), brine (25 mL), dried (MgSO₄) and concentrated under reduced pressure. The crude product was purified by flash column chromatography on silica gel (CH₂Cl₂, MeOH, gradient 98:2-96:4) to furnish the title compound as a white solid (51 mg, 20%), m.p. 201-202° C.; u$_{max}$ (CHCl₃)/cm⁻¹ 3023, 3014, 1724, 1682, 1448, 1360, 1219, 1037; m/z (ESI) $C_{10}H_{14}ClN_4O$ requires 241.0851, found [M+H]⁺ 241.0851.

Example 29

1-(5-bromopyrimidin-4-yl)piperidine-4-carboxamide E29

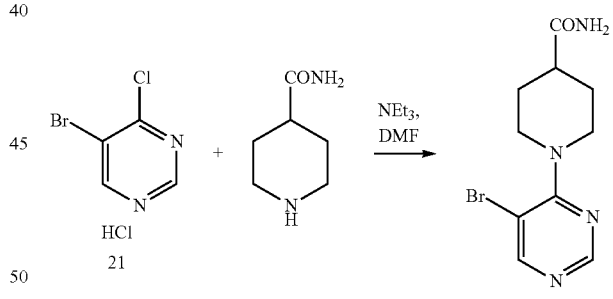

To a solution of 5-bromo-4-chloropyrimidine hydrochloride 21 (0.10 g, 0.36 mmol) in DMF (2 mL) was added triethylamine (0.51 mL, 3.6 mmol). After stirring for 30 min, a solution of isonipecotamide (0.14 g, 1.1 mmol) in DMF (2 mL) was added and the mixture was stirred at r.t. for a further 16 h. The mixture was poured into a saturated solution of sodium hydrogen carbonate (50 mL) and extracted with EtOAc (2×25 mL). The combined organic extracts were washed with water (25 mL), brine (25 mL), dried (MgSO₄) and concentrated under reduced pressure. The crude product was purified by flash column chromatography on silica gel (CH₂Cl₂, MeOH, 98:2) to furnish the title compound as a white solid (60 mg, 58%), m.p. 188-190° C.; u$_{max}$ (CHCl₃)/ cm⁻¹ 3012, 2853, 1682, 1566, 1447, 1359, 1144, 1017, 950; m/z (ESI) $C_{10}H_{14}BrN_4O$ requires 285.0346, found [M+H]⁺ 285.0344.

Example 30

1-(5-methylpyrimidin-4-yl)piperidine-4-carboxamide E30

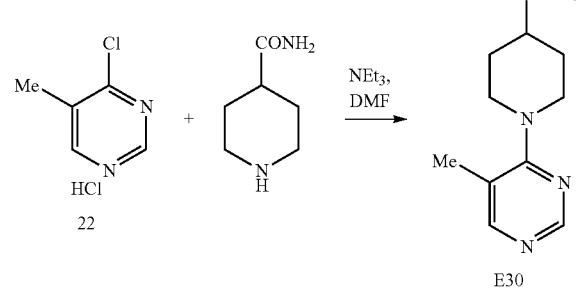

To a solution of 5-methyl-4-chloropyrimidne hydrochloride 22 (75 mg, 0.45 mmol) in DMF (2 mL) was added triethylamine (0.63 mL, 4.5 mmol). After stirring for 15 min, a solution of isonipecotamide (64 mg, 0.50 mmol) in DMF (2 mL) was added and the mixture was stirred at r.t. for a further 20 h. The mixture was poured into a saturated solution of sodium hydrogen carbonate (50 mL) and extracted with EtOAc (2×25 mL). The combined organic extracts were washed with water (25 mL), brine (25 mL), dried (MgSO₄) and concentrated under reduced pressure. The crude product was purified by flash column chromatography on silica gel (CH₂Cl₂, MeOH, gradient 98:2 to 9:1) to furnish the title compound as a white solid (25 mg, 25%), m.p. 182-184° C.; $u_{max}$ (CHCl₃)/cm⁻¹ 3024, 1678, 1581, 1439, 1359, 1147, 948; m/z (ESI) $C_{11}H_{17}N_4O$ requires 221.1397, found [M+H]⁺ 221.1394.

Example 31

1-(5-bromo-2-chloropyrimidin-4-yl)piperidine-4-carboxamide E31

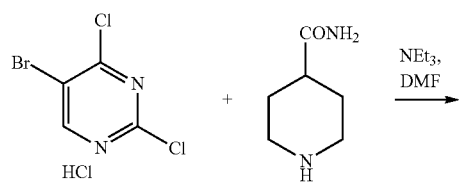

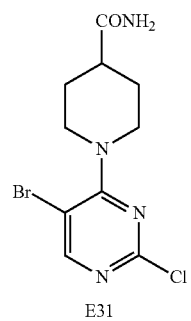

To a solution of 5-bromo-2,4-dichloropyrimidine (0.11 g, 0.50 mmol) and isonipecotamide (77 mg, 0.60 mmol) in DMF (2 mL) was added triethylamine (77 μL, 0.55 mmol) and the mixture was stirred at r.t. for 4.5 h. The mixture was poured into a saturated solution of sodium hydrogen carbonate (10 mL) and extracted with EtOAc (2×10 mL). The combined organic extracts were washed with water (10 mL), brine (10 mL), dried (MgSO₄) and concentrated under reduced pressure. The crude product was purified by flash column chromatography on silica gel (CH₂Cl₂, MeOH, 98:2) to furnish the title compound as a white solid (174 mg, 95%), m/z (ESI) $C_{10}H_{12}BrClN_4NaO$ requires 340.9775 found [M+Na]⁺ 340.9776.

Example 32

1-(2-chloro-5-phenylpyrimidin-4-yl)piperidine-4-carboxamide E32

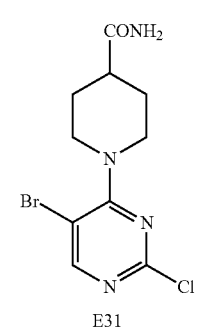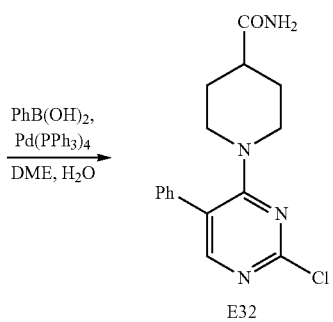

To a solution of 1-(5-bromo-2-chloropyrimidin-4-yl)piperidine-4-carboxamide E31 (0.10 g, 0.31 mmol), benzene boronic acid (46 mg, 0.38 mmol) and tetrakis(triphenylphosphine)palladium(0) (20 mg, 5 mol %) in DME (8 mL) was added a 0.5 M solution of sodium carbonate. The mixture was heated at relfux for 22 h, then cooled to r.t. and purified on an SCX-2 cartridge (MeOH, followed by 0.5 M NH₃ in MeOH). The crude product was purified by chromatography on silica gel (CH₂Cl₂, MeOH, 98:2) to furnish the title compound as a white solid (58 mg, 59%), m/z 317 (100%, MH⁺); m/z (ESI) $C_{16}H_{18}BrClN_4O$ requires 317.1165 found [M+H]⁺ 317.1161.

Example 33

1-(5-phenylpyrimidin-4-yl)piperidine-4-carboxamide E33

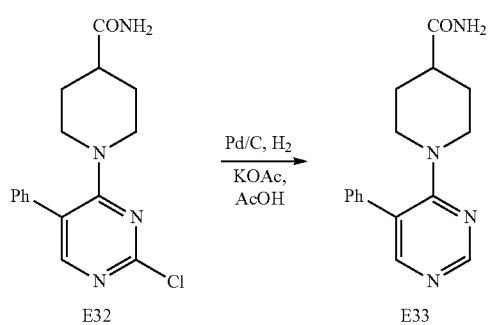 [SMILES: NC(=O)C1CCN(c2nc(Cl)ncc2-c2ccccc2)CC1 ; NC(=O)C1CCN(c2ncncc2-c2ccccc2)CC1]

A mixture of 1-(2-chloro-5-phenylpyrimidin-4-yl)piperidine-4-carboxamide E32 (35 mg, 0.11 mmol), potassium acetate (22 mg, 0.22 mmol) and 10% wt palladium on carbon (3.5 mg) in acetic acid (2 mL) was stirred under an atmosphere of hydrogen (1 atm) for 18 h. The mixture was filtered through celite, washed with AcOH (2×10 mL) and concentrated under reduced pressure. The crude product was purified by preparative tlc on silica gel (CH$_2$Cl$_2$/MeOH, 10:1) to furnish the title compound as a white solid (9 mg, 29%) m/z 283 (100%, [M+H]$^+$); m/z (ESI) C$_{16}$H$_{19}$N$_4$O requires 283.1553 found [M+H]$^+$ 283.1549.

Example 35

2-(1-(3,5-dichloropyridin-4-yl)piperidin-4-yl)thiazole E34

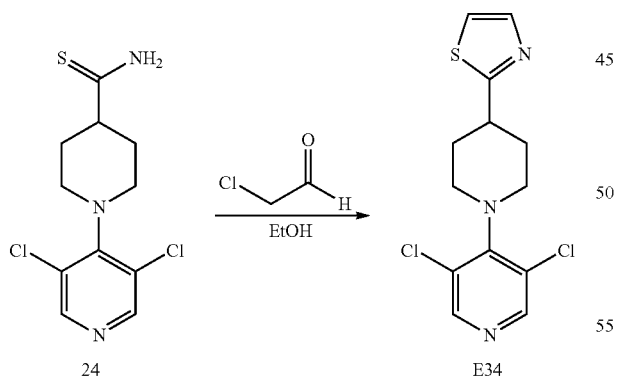

To a solution of 1-(3,5-dichloropyridin-4-yl)piperidine-4-carbothioamide 24 (23 mg, 0.079 mmol) in ethanol (2 mL) was added chloroacetaldehyde (50% wt in H$_2$O) (0.26 mL, 0.16 mmol) and the mixture was heated at reflux for 17 h. The mixture was concentrated and chloroform (10 mL) was added to the residue. The solution was washed with water (10 mL) and extracted with chloroform (10 mL). The combined organic extracts were washed with brine (10 mL), dried (MgSO$_4$) and concentrated under reduced pressure to furnish a brown oil (40 mg). The crude product was purified by preparative tlc on silica gel (CH$_2$Cl$_2$, MeOH, 10:1, then hexane, EtOAc, 1:1) to furnish the title compound as a pale brown solid (5 mg, 20%), LC-MS (ESI) R$_t$ 2.79 min, m/z 314 (100%, M$^+$).

Example 35

2-(1-(3,5-dichloropyridin-4-yl)piperidin-4-yl)oxazole E35

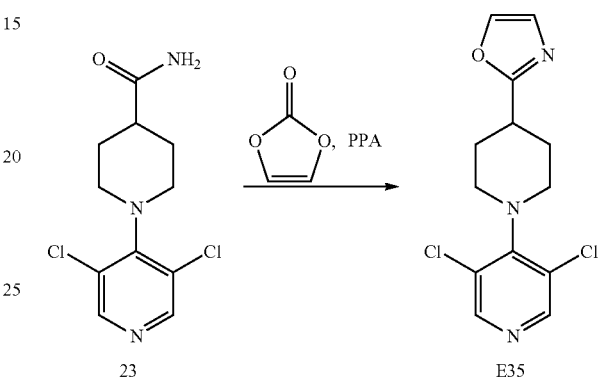

To a solution of 1-(3,5-dichloropyridin-4-yl)piperidine-4-carboxamide 23 (0.10 g, 0.36 mmol) in polyphosphoric acid (5 mL) at 80° C. was added vinylene carbonate (35 mg, 0.40 mmol). The mixture was heated at 170° C. for 4 hours, cooled to r.t. and poured into water (200 mL). The mixture was extracted with ethyl acetate (3×50 mL) and the combined organic extracts were washed with water (100 mL), a saturated solution of sodium hydrogen carbonate (50 mL), water (50 mL), brine (50 mL), dried (MgSO$_4$) and concentrated under reduced pressure to furnish a colourless oil (12 mg). The crude product was purified by preparative tlc on silica gel (CH$_2$Cl$_2$, MeOH, 10:1 then hexane, EtOAc, 1:1) to furnish the title compound as a white solid (13 mg, 12%), LC-MS (ESI) R$_t$ 2.66 min, m/z 298 (100%, W); m/z (ESI) C$_{13}$H$_{14}$Cl$_2$N$_3$O requires 298.0508 found [M+H]$^+$ 298.0507.

Example 36

1-(3-bromopyridin-4-yl)piperidine-4-carboxamide E36

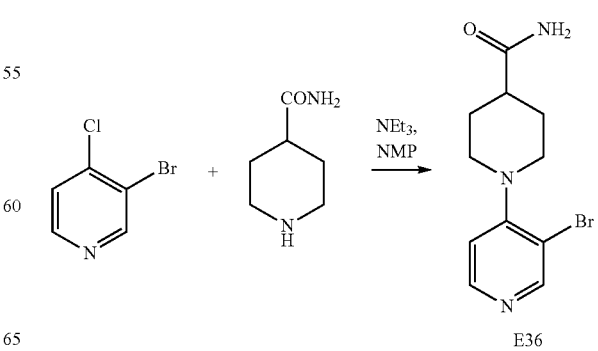

General procedure C was followed using 3-bromo-4-chloro-pyridine (0.10 g, 0.52 mmol) and isonipecotamide (67 mg, 0.52 mmol) NMP (2 mL) and triethylamine (0.14 mL, 1.0 mmol). The crude product was purified by flash column chromatography on silica gel (CH$_2$Cl$_2$, MeOH, gradient 99:1 to 95:5) to furnish the title compound as a white solid (49 mg, 33%), LC-MS (ESI) R$_t$ 0.80 min, m/z 284 (100%, [M+H]$^+$); m/z (ESI) C$_{11}$H$_{15}$BrN$_3$O requires 284.0393 found [M+H]$^+$ 284.0392.

Example 37

1-(3-(4-methoxyphenyl)pyridin-4-yl)piperidine-4-carboxamide E37

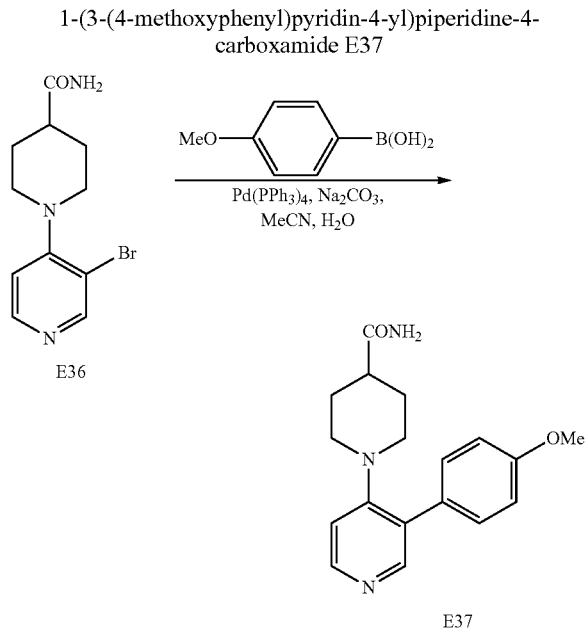

General procedure D (See Example 4) was followed using 1-(3-bromopyridin-4-yl)piperidine-4-carboxamide E36 (50 mg, 0.17 mmol), 4-methoxyphenylboronic acid (32 mg, 0.21 mmol), tetrakis (triphenylphosphine)palladium(0) (10 mg, 5 mol %), acetonitrile (1.2 mL) and 0.5 M sodium carbonate (0.49 mL, 0.25 mmol) for 50 min. The crude product was purified by flash column chromatography on silica gel (CH$_2$Cl$_2$, MeOH, gradient 97:3 to 95:5) to furnish the title compound as a white solid (49 mg, 89%), LC-MS (ESI) R$_t$ 1.28 min, m/z 312 (100%, [M+H]$^+$); m/z (ESI) C$_{18}$H$_{22}$N$_3$O$_2$ requires 312.1706 found [M+H]$^+$ 312.1705.

Example 38

1-(3-(thiophen-2-yl)pyridin-4-yl)piperidine-4-carboxamide E38

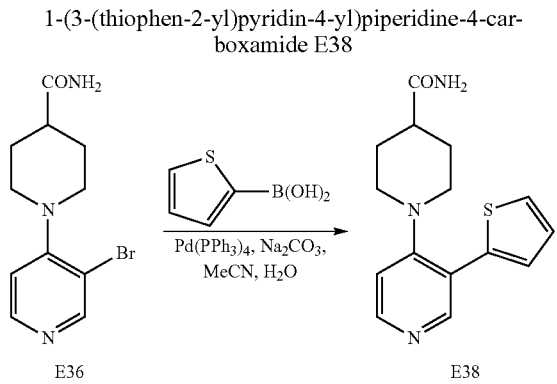

General procedure D (See Example 4) was followed using 1-(3-bromopyridin-4-yl)piperidine-4-carboxamide E36 (25 mg, 0.088 mmol), thiophene-2-boronic acid (13 mg, 0.11 mmol), tetrakis (triphenylphosphine)palladium(0) (5 mg, 5 mol %), acetonitrile (1 mL) and 0.5 M sodium carbonate (0.25 mL, 0.12 mmol) for 30 min. The crude product was purified by preparative tlc on silica gel (CH$_2$Cl$_2$, MeOH, 10:1) to furnish the title compound as a white solid (23 mg, 91%), LC-MS (ESI) R$_t$ 1.17 min, m/z 288 (100%, [M+H]$^+$); m/z (ESI) C$_{15}$H$_{18}$N$_3$OS requires 288.1165 found [M+H]$^+$ 288.1163.

Examples 39 and 40

1-(3-bromo-5-phenylpyridin-4-yl)piperidine-4-carboxamide E39 and 1-(3,5-diphenylpyridin-4-yl)piperidine-4-carboxamide E40

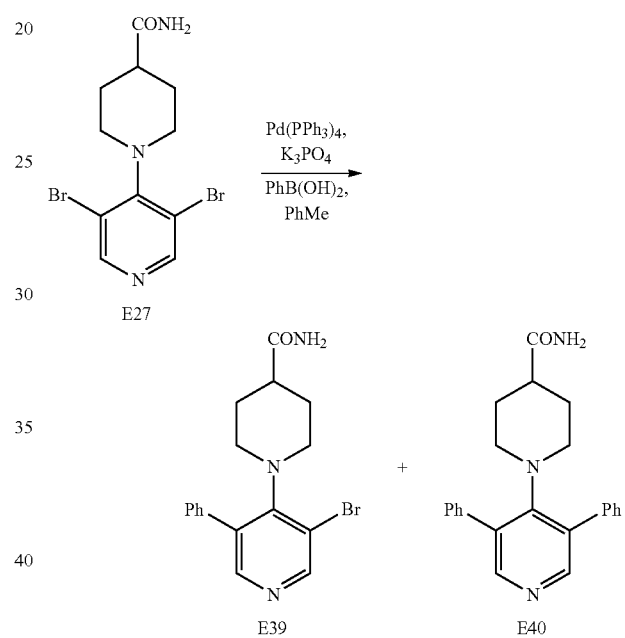

To a solution of 1-(3,5-dibromopyridin-4-yl)piperidine-4-carboxamide E27 (50 mg, 0.14 mmol), benzene boronic acid (70 mg, 0.58 mmol) and potassium phosphate (0.20 g, 0.96 mmol) in toluene (1.5 mL) was added tetrakis(triphenylphosphine)palladium(0) (18 mg, 0.014 mmol). The mixture was heated at 170° C. in a microwave reactor for 45 min, then poured into a saturated solution of sodium hydrogen carbonate (25 mL). The mixture was extracted with EtOAc (2×25 mL) and the combined organic extracts were washed with water (25 mL), brine (25 mL), dried (MgSO$_4$) and the solvent was removed under reduced pressure. The crude product was purified by flash column chromatography on silica gel (CH$_2$Cl$_2$, MeOH, 98:2) to furnish a 2:3 mixture of mono- and bis-coupled products. Analytical samples were further purified by preparative HPLC (MeCN, H$_2$O 5:95):

1-(3-bromo-5-phenylpyridin-4-yl)piperidine-4-carboxamide E39: (4.2 mg, 8%), m.p. 220-222° C.; u$_{max}$ (CHCl$_3$)/cm$^{-1}$ 3029, 1684, 1441, 1383; m/z (ESI) C$_{17}$H$_{19}$BrN$_3$O requires 360.0706, found [M+H]$^+$ 360.0706.

1-(3,5-diphenylpyridin-4-yl)piperidine-4-carboxamide E40: (14 mg, 28%), u$_{max}$ (CHCl$_3$)/cm$^{-1}$ 3039, 1731, 1375, 1249, 1045, 1016; m/z (ESI) C$_{23}$H$_{24}$N$_3$O requires 358.1914, found [M+H]$^+$ 358.1911.

Example 41

1-(3-bromo-5-(4-(trifluoromethyl)phenyl)pyridin-4-yl)piperidine-4-carboxamide E41

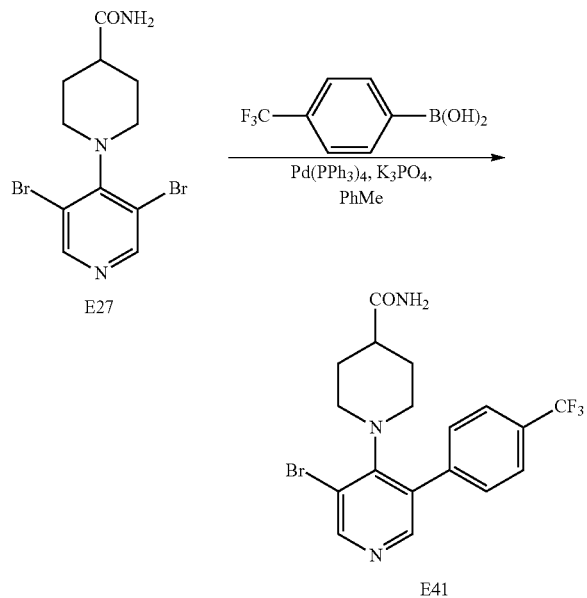

To a solution of 1-(3,5-dibromopyridin-4-yl)piperidine-4-carboxamide E27 (50 mg, 0.14 mmol), 4-trifluoromethylbenzene boronic acid (0.11 g, 0.56 mmol) and potassium phosphate (0.20 g, 0.96 mmol) in toluene (4 mL) was added tetrakis(triphenylphosphine)palladium(0) (18 mg, 10 mol %). The mixture was heated at 170° C. in a microwave reactor for 60 min, then poured into a saturated solution of sodium hydrogencarbonate (25 mL). The mixture was extracted with EtOAc (2×20 mL) and the combined organic extracts were washed with water (25 mL), brine (25 mL), dried (MgSO$_4$) and the solvent was removed under reduced pressure. The crude product was purified by flash column chromatography on silica gel (CH$_2$Cl$_2$, MeOH, 98:2) and further purified preparative hplc (H$_2$O, MeCN, gradient 90:10 to 10:90 over 30 min) (11 mg, 9%), m/z (ESI) C$_{18}$H$_{18}$BrF$_3$N$_3$O requires 428.0580 found [M+H]$^+$ 428.0574.

Example 42

1-(3-chloro-5-phenylpyridin-4-yl)piperidine-4-carboxamide E42

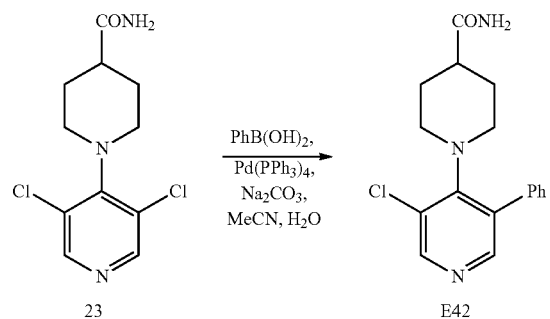

General procedure D (See Example 4) was followed using 1-(3,5-dichloropyridin-4-yl)piperidine-4-carboxamide 23 (24 mg, 0.088 mmol), benzene boronic acid (13 mg, 0.11 mmol), tetrakis(triphenylphosphine)palladium(0) (5 mg, 5 mol %), acetonitrile (1 mL) and 0.5 M sodium carbonate (0.25 mL, 0.12 mmol) for 30 min. The crude product was purified by preparative hplc (H$_2$O, MeCN, gradient 90:10 to 10:90 over 30 min) to furnish the title compound as a white solid (6 mg, 22%), LC-MS (ESI) R$_t$ 1.63 min, m/z 316 (100%, [M+H]$^+$); m/z (ESI) C$_{17}$H$_{18}$ClN$_3$NaO requires 338.1031 found [M+Na]$^+$ 338.1030.

Example 43

1-(3-chloro-5-(4-methoxyphenyl)pyridin-4-yl)piperidine-4-carboxamide E43

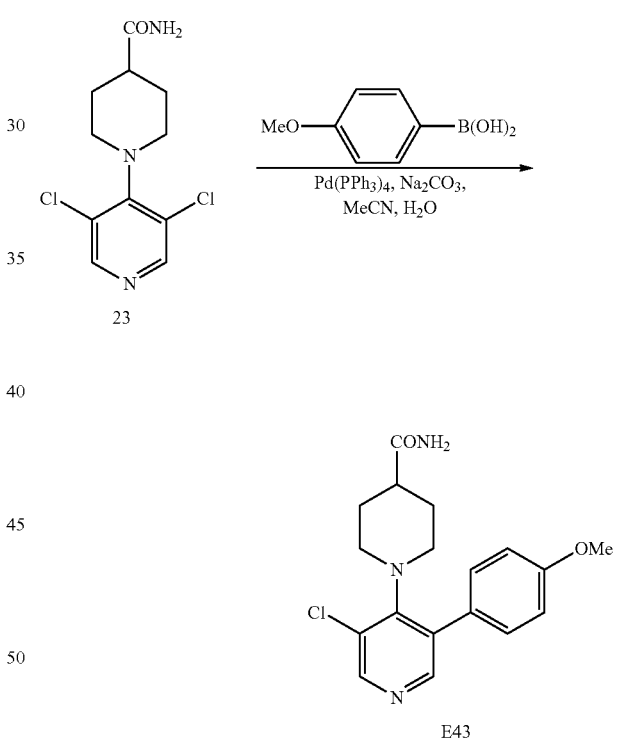

General procedure D (See Example 4) was followed using 1-(3,5-dichloropyridin-4-yl)piperidine-4-carboxamide (24 mg, 0.088 mmol), 4-methoxybenzene boronic acid (16 mg, 0.11 mmol), tetrakis(triphenylphosphine)palladium(0) (5 mg, 5 mol %), acetonitrile (1 mL) and 0.5 M sodium carbonate (0.25 mL, 0.12 mmol) for 30 min. The crude product was purified by preparative hplc (CH$_3$CN, H$_2$O, 23:77) to furnish the title compound as a white solid (9 mg, 30%), LC-MS (ESI) R$_t$ 1.67 min, m/z 346 (100%, [M+H]$^+$); m/z (ESI) C$_{18}$H$_{21}$ClN$_3$O$_2$ requires 346.1317 found [M+H]$^+$ 346.1317.

Example 44

1-(3-chloro-5-(1H-pyrazol-5-yl)pyridin-4-yl)piperidine-4-carboxamide E44

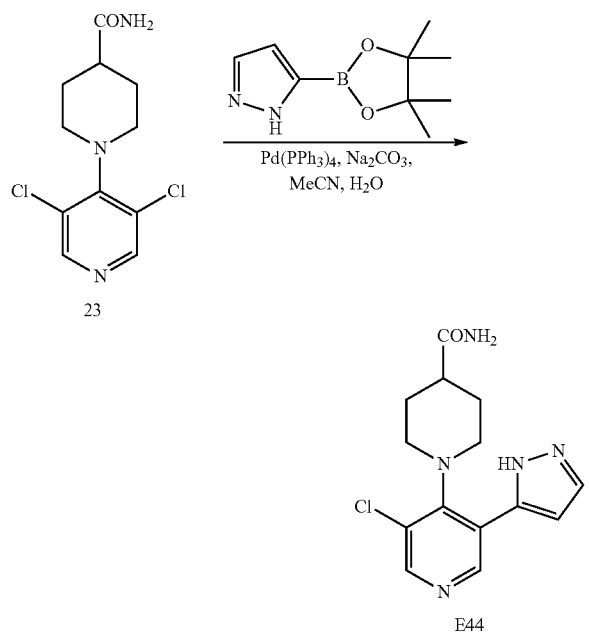

General procedure D (See Example 4) was followed using 1-(3,5-dichloropyridin-4-yl)piperidine-4-carboxamide (24 mg, 0.088 mmol), 1H-pyrazole-5-boronic acid pinacol ester (19 mg, 0.11 mmol), tetrakis(triphenylphosphine)palladium (0) (5 mg, 5 mol %), acetonitrile (1 mL) and 0.5 M sodium carbonate (0.25 mL, 0.12 mmol) for 30 min. The crude product was purified by preparative tlc on silica gel (CH$_2$Cl$_2$, MeOH, 10:1) to furnish the title compound as a white solid (18 mg, 67%), LC-MS (ESI) R$_t$ 1.06 min, m/z 306 (100%, [M+H]$^+$); m/z (ESI) C$_{14}$H$_{17}$ClN$_5$O requires 306.1116 found [M+H]$^+$ 306.1114.

Example 45

1-(3-chloro-5-(1,5-dimethyl-1H-pyrazol-4-yl)pyridin-4-yl)piperidine-4-carboxamide E45

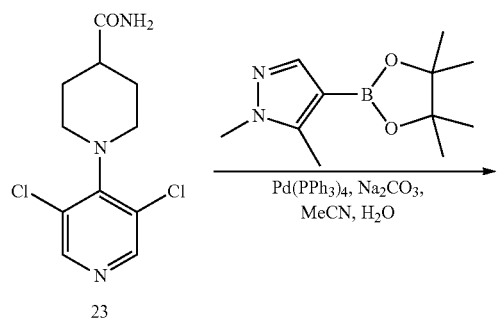

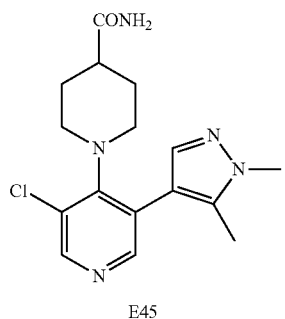

General Procedure E

To a suspension of 1-(3,5-dichloropyridin-4-yl)piperidine-4-carboxamide 23 (75 mg, 0.27 mmol), 1,5-dimethyl-4-pyrazole boronic acid pinacol ester (76 mg, 0.34 mmol) and tetrakis(triphenylphosphine)palladium(0) (16 mg, 5 mol %) in acetonitrile (3 mL) was added 0.5 M solution of sodium carbonate (0.77 mL, 0.38 mmol). The mixture was heated to in a microwave reactor at 150° C. for 45 min. Once cooled the reaction was concentrated in vacuo and dry loaded onto silica. The crude product was purified by flash column chromatography on silica gel (CH$_2$Cl$_2$, EtOH, 97:3-80:20, biotage 25+S) to furnish the title compound as a clear colourless oil (24 mg, 26%), LC-MS (ESI, 4 min) R$_t$ 1.49 min, m/z 334 (100%, [M+H]$^+$); m/z (ESI) C$_{16}$H$_{20}$N$_5$OCl requires 333.1356, found [M+H]$^+$ 333.1354.

Example 46

1-(3-chloro-5-(2-(methylthio)pyrimidin-5-yl)pyridin-4-yl)piperidine-4-carboxamide E46

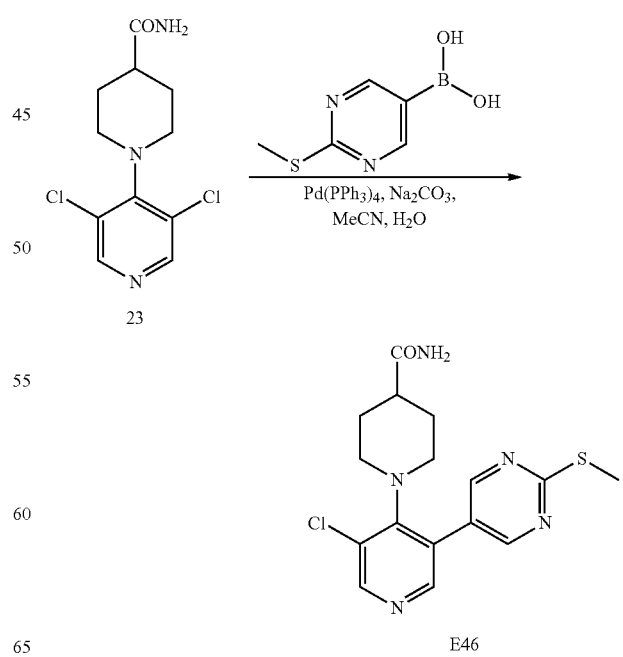

General procedure E was followed using 1-(3,5-dichloropyridin-4-yl)piperidine-4-carboxamide (75 mg, 0.27 mmol), 2-(methylthio)pyrimidine-5-boronic acid (58 mg, 0.34 mmol), tetrakis(triphenylphosphine)palladium(0) (16 mg, 5 mol %), acetonitrile (3 mL) and 0.5 M sodium carbonate (0.77 mL, 0.38 mmol). The crude product was purified by flash column chromatography on silica gel (CH$_2$Cl$_2$, EtOH, 96:4-82:18, biotage 25+S) to furnish the title compound as an off white solid (11 mg, 11%), along with recovered 1-(3,5-dichloropyridin-4-yl)piperidine-4-carboxamide as a white solid (41 mg, 55% RSM), LC-MS (ESI, 4 min) R$_t$ 2.14 min, m/z 364 (100%, [M+H]$^+$); m/z (ESI) C$_{16}$H$_{18}$N$_5$OSCl requires 363.09206, found [M+H]$^+$ 363.0922.

Example 47

1-(3-chloro-5-(1,3-dimethyl-1H-pyrazol-4-yl)pyridin-4-yl)piperidine-4-carboxamide E47

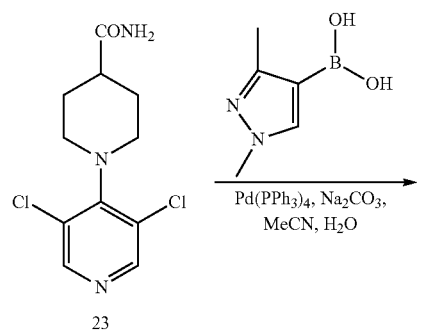

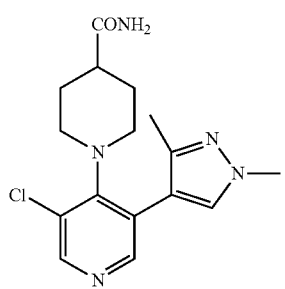

E47

General procedure E was followed using 1-(3,5-dichloropyridin-4-yl)piperidine-4-carboxamide (75 mg, 0.27 mmol), 1,3-dimethyl-4-pinacolboranyl-1H-pyrazole (76 mg, 0.34 mmol), tetrakis(triphenylphosphine)palladium(0) (16 mg, 5 mol %), acetonitrile (3 mL) and 0.5 M sodium carbonate (0.77 mL, 0.38 mmol). The crude product was purified by flash column chromatography on silica gel (CH$_2$Cl$_2$, EtOH, 94:6-80:20, biotage 25+S) to furnish the title compound as a white solid (16 mg, 18%), along with recovered 1-(3,5-dichloropyridin-4-yl)piperidine-4-carboxamide (30 mg, 40% RSM), LC-MS (ESI, 4 min) R$_t$ 1.40 min, m/z 334 (100%, [M+H]$^+$); m/z (ESI) C$_{16}$H$_{20}$N$_5$OCl requires 333.1356, found [M+H]$^+$ 333.1356.

Example 48

1-(3,5-dichloropyridin-4-yl)piperidine-4-carbonitrile E48

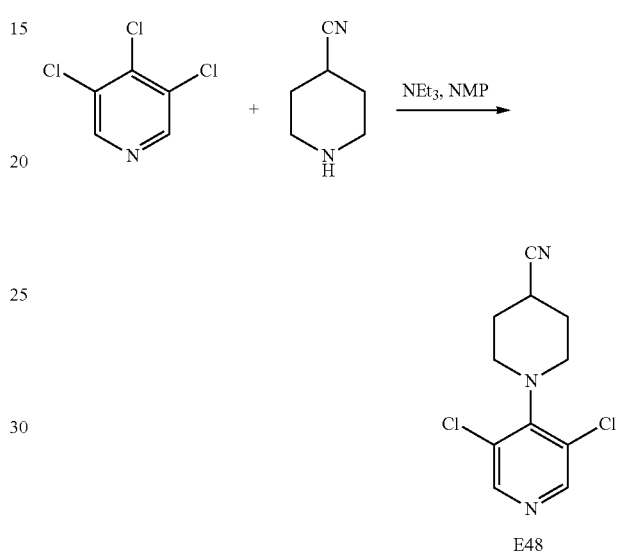

General procedure C was followed using 3,4,5-trichloropyridine (0.50 g, 2.7 mmol), isonipecotamide (0.30 mg, 2.7 mmol), NMP (15 mL) and triethylamine (0.76 mL, 5.5 mmol). The crude product was purified by flash column chromatography on silica gel (CH$_2$Cl$_2$, MeOH, 99:1) to furnish the title compound as a white solid (228 mg, 33%), m/z (ESI) C$_{11}$H$_{12}$Cl$_2$N$_3$ requires 256.0403 found [M+H]$^+$ 256.0409.

Example 49

1-(3,5-dichloropyridin-4-yl)-4-methylpiperidine-4-carbonitrile E49

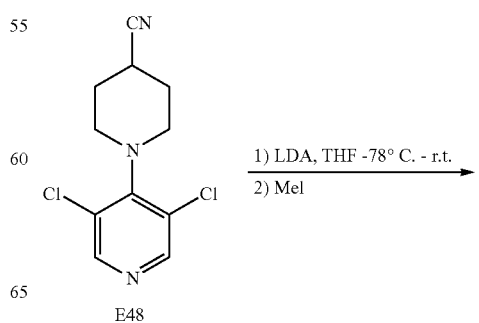

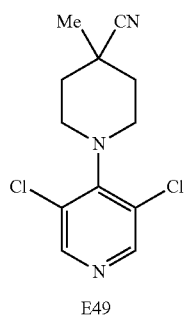

E49

To a solution of 1-(3,5-dichloropyridin-4-yl)piperidine-4-carbonitrile E48 (90 mg, 0.35 mmol) in THF (1.5 mL), at −78° C., was added a 1M solution of LDA in THF (0.38 mL, 0.38 mmol). The mixture was stirred for 30 min at −78° C. before warming to r.t. After 60 min, methyl iodide (31 µL, 0.5 mmol) was added. The mixture was stirred for a further 60 min at r.t. for 1 h, before addition of water (5 mL). The mixture was extracted with $CH_2Cl_2$ (3×5 mL) and the combined organic extracts were dried over $MgSO_4$ and concentrated under reduced pressure to dryness. The crude product was purified by flash column chromatography on silica gel (hexane, EtOAc, 100:0-80:20, biotage 25+M) to furnish the title compound as a white solid (34 mg, 36%), along with recovered 1-(3,5-dichloropyridin-4-yl)piperidine-4-carbonitrile (23 mg, 25%), LC-MS (ESI, 4 min) $R_t$ 3.09 min, m/z 270 (100%, W); m/z (ESI) $C_{12}H_{13}Cl_2N_3$ requires 269.0487 found $[M+H]^+$ 289.0488.

Example 50

1-(3-chloro-5-(4-fluorophenyl)pyridin-4-yl)piperidine-4-carboxamide E50

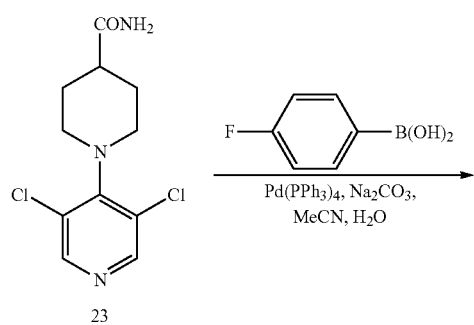

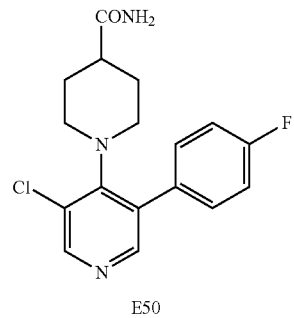

E50

General procedure D was followed using 1-(3,5-dichloropyridin-4-yl)piperidine-4-carboxamide (24 mg, 0.088 mmol), 4-fluorobenzene boronic acid (15 mg, 0.11 mmol) and tetrakis(triphenylphosphine)palladium(0) (5 mg, 5 mol %), acetonitrile (1 mL) and 0.5 M sodium carbonate (0.25 mL, 0.12 mmol) for 30 min. The crude product was purified by preparative tlc on silica gel ($CH_2Cl_2$, MeOH, 10:1) to give impure title compound (19 mg) which was further purified by preparative hplc ($CH_3CN$, $H_2O$, gradient 1:9 to 9:1) to furnish the title compound as a white solid, LC-MS (ESI, 3.5 min) $R_t$ 1.71 min, m/z 334 (100%, $[M+H]^+$); m/z (ESI) $C_{17}H_{18}ClFN_3O$ requires 334.1117 found $[M+H]^+$ 334.1116.

Example 51

1-(3-chloro-5-(4-trifluoromethyl)phenyl)pyridin-4-yl)piperidine-4-carboxamide E51

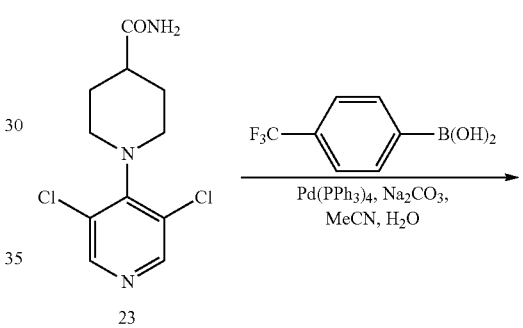

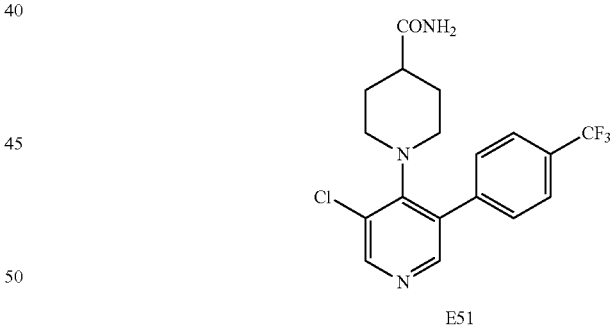

E51

General procedure D was followed using 1-(3,5-dichloropyridin-4-yl)piperidine-4-carboxamide (24 mg, 0.088 mmol), (4-trifluoromethyl)benzene boronic acid (20 mg, 0.11 mmol) and tetrakis(triphenylphosphine)palladium(0) (5 mg, 5 mol %), acetonitrile (1 mL) and 0.5 M sodium carbonate (0.25 mL, 0.12 mmol) for 30 min. The crude product was purified by preparative tlc on silica gel ($CH_2Cl_2$, MeOH, 10:1) followed by preparative hplc ($CH_3CN$, $H_2O$, gradient 1:9 to 9:1) to furnish the title compound as a white solid (10 mg, 30%), LC-MS (ESI, 3.5 min) $R_t$ 2.26 min, m/z 384 (100%, $[M+H]^+$); m/z (ESI) $C_{18}H_{18}ClF_3N_3O$ requires 384.1085 found $[M+H]^+$ 384.1084.

Example 52

1-(3-(4-fluoro-3-methylphenyl)pyridin-4-yl)piperidine-4-carboxamide E52

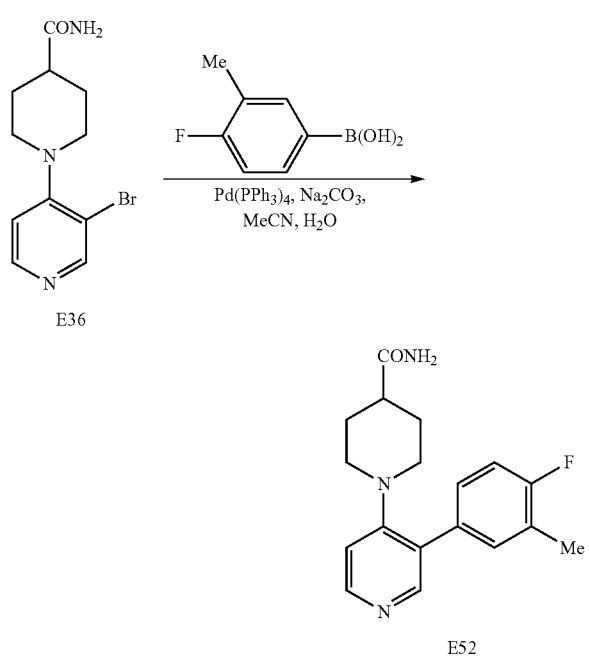

E52

General procedure D was followed using 1-(3-bromopyridin-4-yl)piperidine-4-carboxamide E36 (25 mg, 0.088 mmol), 4-fluoro-3-methylphenylboronic acid (16 mg, 0.11 mmol), tetrakis(triphenylphosphine)palladium(0) (5 mg, 5 mol %), 0.5 M sodium carbonate (0.25 mL, 0.12 mmol) and acetonitrile (1 mL) for 50 min. The crude product was purified by preparative tlc (CH$_2$Cl$_2$, MeOH, 10:1) to furnish the title compound as a white solid (15 mg, 56%), LC-MS (ESI 3.5 min) R$_t$ 1.46 min, m/z 314 (100%, [M+H]$^+$); m/z (ESI) C$_{18}$H$_{21}$FN$_3$O requires 314.1663 found [M+H]$^+$ 314.1658.

Example 53

1-(3-(3,5-dimethylisoxazol-4-yl)pyridin-4-yl)piperidine-4-carboxamide E53

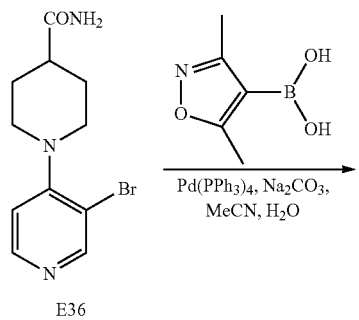

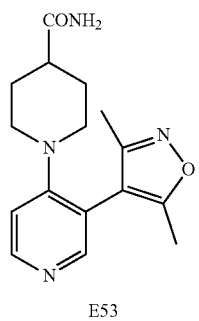

E53

General procedure E was followed using 1-(3-bromopyridin-4-yl)piperidine-4-carboxamide E36 (100 mg, 0.35 mmol), 3,5-dimethyl-4-isoxazole boronic acid (74 mg, 0.53 mmol), tetrakis(triphenylphosphine)palladium(0) (20 mg, 5 mol %), acetonitrile (4 mL) and 0.5 M sodium carbonate (1.1 mL, 0.53 mmol). The crude product was purified by flash column chromatography on silica gel (CH$_2$Cl$_2$, EtOH, 97:3-80:20, biotage 25+S) to furnish the title compound as a white solid (18 mg, 17%), along with 1-(3-bromopyridin-4-yl)piperidine-4-carboxamide (10 mg, 10% RSM), LC-MS (ESI, 4 min) R$_t$ 0.76 min, m/z 301 (100%, [M+H]$^+$); m/z (ESI, R$_t$ 1.22 min) C$_{16}$H$_{20}$N$_4$O$_2$ requires 300.1587, found [M+H]$^+$ 300.1591.

Examples 54 and 55

8-(3,5-dichloropyridin-4-yl)-1-phenyl-1,3,8-triazaspiro[4.5]decan-4-one E54 and 1-(3,5-dichloropyridin-4-yl)-4-(phenylamino)piperidine-4-carboxamide E55

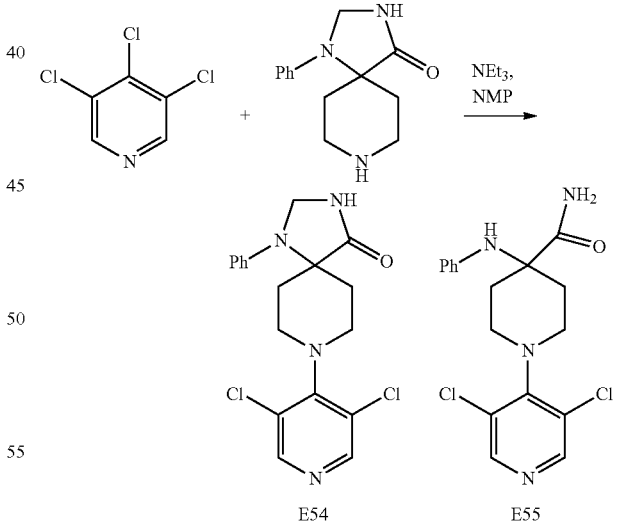

General procedure D was followed using 3,4,5-trichloropyridine (120 mg, 0.66 mmol), 1-phenyl-1,3,8-triazaspiro[4,5]decan-4-one (150 mg, 0.66 mmol), NMP (3.6 ml) and triethylamine (0.19 ml, 1.3 mmol) to give a crude orange/white oily solid (105 mg). The crude product was purified by flash column chromatography on silica gel (hexane, EtOAc, 80:20-10:90, biotage 25+S) to furnish impure title compound E54 as an off white solid (39 mg) and impure title compound E55 as an off white solid (97 mg). Both products where further purified by recrystallisation in EtOAc/Et$_2$O to furnish title compound E54 as an off white solid (13 mg, 5%) and title compound E55 as an off white solid (46 mg, 19%).

8-(3,5-dichloropyridin-4-yl)-1-phenyl-1,3,8-triazaspiro[4.5]decan-4-one E54: LC-MS (ESI, 4 min) R$_t$ 3.26 min, m/z 377 (100%, [M+H]$^+$); m/z (ESI) C$_{18}$H$_{18}$N$_4$Cl$_2$O requires 376.0858, found [M+H]$^+$ 364.0869.

1-(3,5-dichloropyridin-4-yl)-4-(phenylamino)piperidine-4-carboxamide E55: LC-MS (ESI, 4 min) R$_t$ 2.99 min, m/z 365 (100%, [M+H]$^+$); m/z (ESI) C$_{17}$H$_{18}$N$_4$Cl$_2$O requires 364.0858, found [M+H]$^+$ 364.0851.

Example 56

1-(3-chloro-5-(pyrimidin-5-yl)pyridin-4-yl)piperidine-4-carboxamide E56

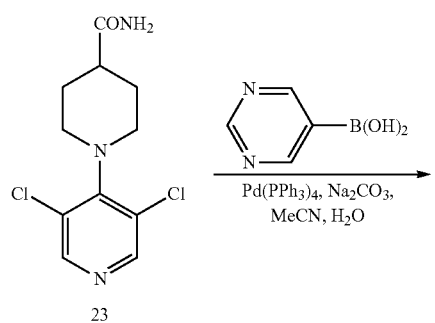

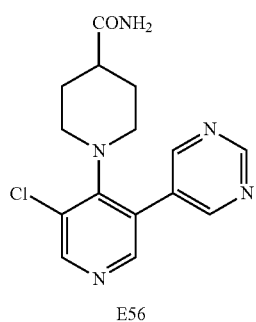

General procedure D was followed using 1-(3,5-dichloropyridin-4-yl)piperidine-4-carboxamide 23 (24 mg, 0.088 mmol), pyrimidin-5-yl boronic acid (12 mg, 0.11 mmol) and tetrakis(triphenylphosphine)palladium(0) (5 mg, 5 mol %), acetonitrile (1 mL) and a 0.5 M sodium carbonate (0.25 mL, 0.12 mmol) for 30 min. The crude product was purified by preparative tlc on silica gel (CH$_2$Cl$_2$, MeOH, 10:1) to furnish the title compound as a white solid (26 mg, 95%), LC-MS (ESI, 3.5 min) R$_t$ 1.19 min, m/z 318 (100%, [M+H]$^+$); m/z (ESI) C$_{15}$H$_{17}$ClN$_5$O requires 318.1116 found [M+H]$^+$ 318.1114.

Example 57

1-(3-(thiophen-3-yl)pyridin-4-yl)piperidine-4-carboxamide E57

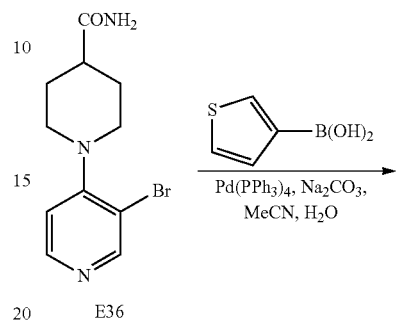

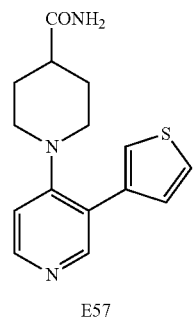

General procedure D was followed using 1-(3-bromopyridin-4-yl)piperidine-4-carboxamide E36 (17 mg, 0.060 mmol), thiophene-3-boronic acid (9.2 mg, 0.072 mmol), tetrakis(triphenylphosphine)palladium(0) (3.5 mg, 5 mol %), 0.5 M sodium carbonate (0.17 mL, 0.084 mmol) and acetonitrile (1 mL) for 50 min. The crude product was purified by preparative tlc (CH$_2$Cl$_2$, MeOH, 10:1) to furnish the title compound as a white solid (13 mg, 76%), LC-MS (ESI, 3.5 min) R$_t$ 1.12 min, m/z 288 (100%, [M+H]$^+$); m/z (ESI) C$_{15}$H$_{18}$N$_3$OS requires 288.1165 found [M+H]$^+$ 288.1163.

Example 58

1-(3-chloro-5-(1,3,5-trimethyl-1H-pyrazol-4-yl)pyridin-4-yl)piperidine-4-carboxamide E58

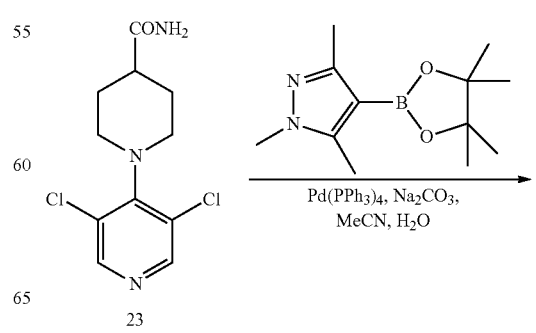

-continued

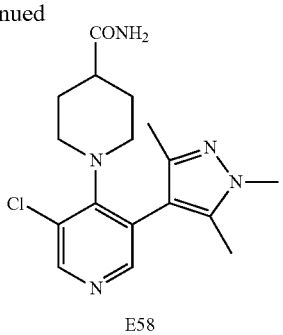

E58

General procedure E was followed using 1-(3,5-dichloropyridin-4-yl)piperidine-4-carboxamide 23 (75 mg, 0.27 mmol), 1,3,5-trimethyl-1H-pyrazole-4-boronic pinacol ester (65 mg, 0.27 mmol), tetrakis(triphenylphosphine)palladium (0) (16 mg, 5 mol %), acetonitrile (3 mL) and 0.5 M sodium carbonate (0.77 mL, 0.38 mmol). The crude product was purified by flash column chromatography on silica gel ($CH_2Cl_2$, EtOH, 94:6-80:20, biotage 25+S) to furnish the title compound as a very pale yellow solid (34 mg, 35%), along with recovered 1-(3,5-dichloropyridin-4-yl)piperidine-4-carboxamide (52 mg, 57% RSM), LC-MS (ESI, 4 min) $R_t$ 1.55 min, m/z 348 (100%, [M+H]$^+$); m/z (ESI) $C_{17}H_{22}N_5OCl$ requires 347.1513, found [M+H]$^+$ 347.1508.

Example 59

8-(3,5-dichloropyridin-4-yl)-2,8-diazaspiro[4.5]decan-1-one E59

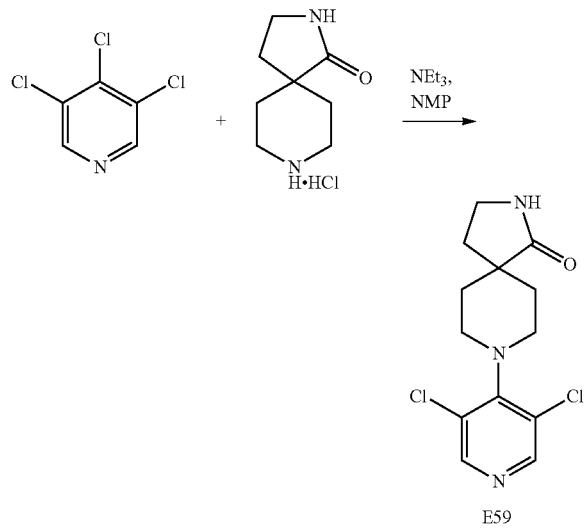

E59

General procedure C was followed using 3,4,5-trichloropyridine (100 mg, 0.55 mmol), 2,8-diazaspiro[4.5]decan-1-one.HCl (85 mg, 0.55 mmol, commercial ASW MedChem Inc.), NMP (3.0 ml) and triethylamine (0.23 ml, 1.6 mmol) to give a crude orange/white oily solid (458 mg). The crude product was purified by flash column chromatography on silica gel ($CH_2Cl_2$, MeOH, 97:3) to furnish impure title compound as an oily white solid (110 mg). Further purification by trituration in $Et_2O$ furnished the title compound as a white solid (57 mg, 35%), LC-MS (ESI, 4 min) $R_t$ 2.66 min, m/z 300 (100%, [M+H]$^+$); m/z (ESI) $C_{13}H_{15}N_3Cl_2O$ requires 299.0593, found [M+H]$^+$ 300.0665.

Example 60

8-(3-chloro-5-phenylpyridin-4-yl)-2,8-diazaspiro[4.5]decan-1-one E60

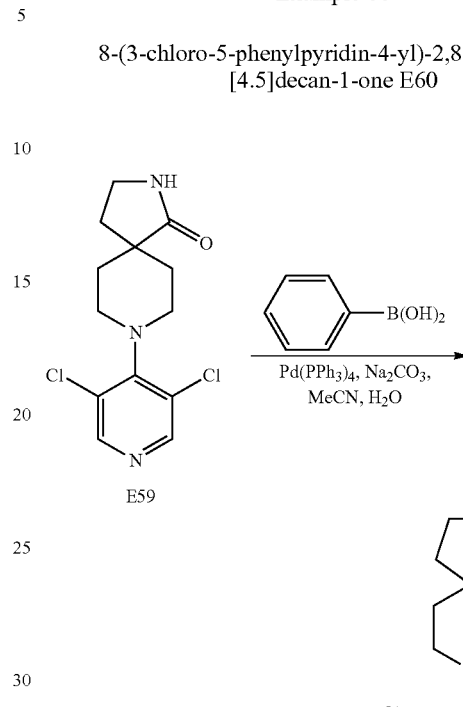

General procedure E was followed using 8-(3,5-dichloropyridin-4-yl)-2,8-diazaspiro[4.5]decan-1-one E59 (38 mg, 0.13 mmol), phenyl boronic acid (19 mg, 0.16 mmol), tetrakis (triphenylphosphine)palladium(0) (7.3 mg, 5 mol %), acetonitrile (1.4 ml) and 0.5 M sodium carbonate (0.35 ml, 0.18 mmol). The crude product was purified by flash column chromatography on silica gel ($CH_2Cl_2$, MeOH, 97:3) followed by preparative hplc ($CH_3CN$, $H_2O$, gradient 1:9 to 9:1) to furnish the title compound as a white solid (12 mg, 28%), along with recovered starting material as a clear colourless oil (10 mg, 23% RSM), LC-MS (ESI, 4 min) $R_t$ 2.22 min, m/z 342 (100%, [M+H]$^+$); m/z (ESI) $C_{19}H_{20}N_3ClO$ requires 341.1295, found [M+H]$^+$ 341.1301.

Example 61

(1-(3,5-dichloropyridin-4-yl)piperidin-4-yl)methanol E61

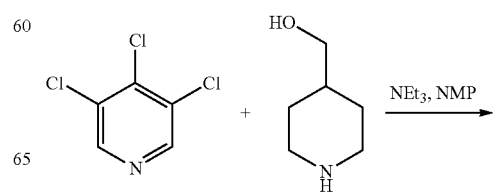

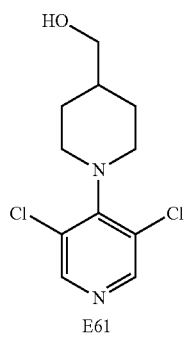

E61

General procedure C was followed using 3,4,5-trichloropyridine (50 mg, 0.27 mmol), piperidin-4-ylmethanol (35 mg, 0.30 mmol), triethylamine (76 µL, 0.54 mmol) and NMP (1.5 mL). The crude product was purified by flash column chromatography on silica gel (hexane, EtOAc, 85:15) to furnish the title compound as white solid (51 mg, 71%), LC-MS (ESI, 3.5 min) $R_t$ 2.49 min, m/z 261 (100%, [M+H]$^+$); m/z (ESI) $C_{11}H_{15}Cl_2N_2O$ requires 261.0556 found [M+H]$^+$ 261.0558; HPLC $R_t$ 6.68 min, 100%.

Example 62

(R,S)-1-(3-chloro-5-phenylpyridin-4-yl)pyrrolidine-3-carbonitrile E62

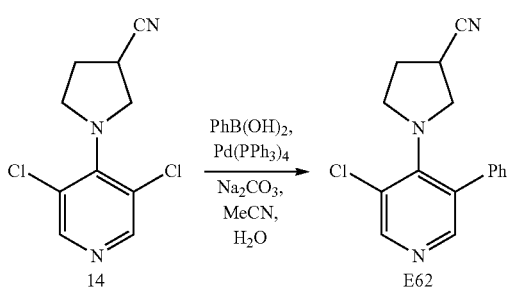 [SMILES: N#CC1CCN(c2c(Cl)cncc2Cl)C1 ; N#CC1CCN(c2c(Cl)cncc2-c2ccccc2)C1]

General procedure D was followed using (R,S)-1-(3,5-dichloropyridin-4-yl)pyrrolidine-3-carbonitrile 14 (25 mg, 0.10 mmol), benzene boronic acid (15 mg, 0.12 mmol), tetrakis(triphenylphosphine)palladium(0) (6 mg, 5 mol %), 0.5 M sodium carbonate (0.29 mL, 0.14 mmol) and acetonitrile (1 mL) for 30 min. The crude product was purified preparative hplc (CH$_3$CN, H$_2$O, gradient 1:9 to 9:1) to furnish the title compound as white solid (8 mg, 27%), LC-MS (ESI, 3.5 min) $R_t$ 1.64 min, m/z 284 (100%, [M+Na]$^+$).

Example 63 ethyl 1-(3,5-dichloropyridin-4-yl)-4-methylpiperidine-4-carboxylate E63

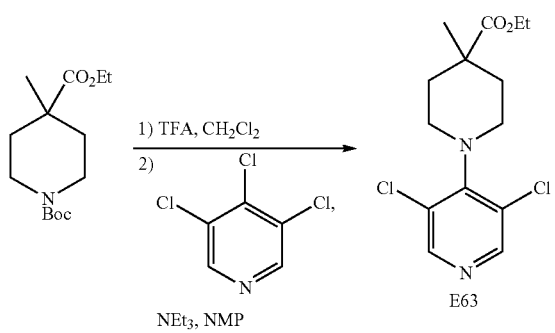 [SMILES: CCOC(=O)C1(C)CCN(C(=O)OC(C)(C)C)CC1 ; Clc1cncc(Cl)c1Cl ; CCOC(=O)C1(C)CCN(c2c(Cl)cncc2Cl)CC1]

To a solution of ethyl N-Boc-4-methylpiperidine-4-carboxylate (130 mg, 0.47 mmol) in CH$_2$Cl$_2$ (8 mL) was added trifluoroacetic acid (0.86 mL, 11 mmol) and the reaction stirred at r.t. for 2 hr before evaporation and aziotrope with toluene (2×25 ml). The crude was dissolved in NMP (4.3 ml) and 3,4,5-trichloropyridine (135 mg, 0.74 mmol) was added followed by triethylamine (0.42 mL, 3.0 mmol) and the mixture was heated in a microwave reactor at 220° C. for 60 min. The mixture was poured into a saturated solution of sodium hydrogen carbonate (50 mL) and extracted with EtOAc (2×100 mL). The combined organic extracts were washed with water (2×50 mL), brine (50 mL), dried (MgSO$_4$) and concentrated under reduced pressure to give a crude pale brown/orange oil (175 mg). The crude product was purified by flash column chromatography on silica gel (cyclohexane, EtOAc, 99:1-88:12, biotage 25+S) to furnish the title compound as a clear colourless oil (85 mg, 56%), LC-MS (ESI, 4 min) $R_t$ 3.36 min, m/z 317 (100%, [M+H]$^+$); m/z (ESI) $C_{14}H_{18}N_2O_2Cl_2$ requires 316.0745, found [M+H]$^+$ 316.0745.

Example 64

(R,S)-1-(3-chloro-5-phenylpyridin-4-yl)pyrrolidine-3-carboxamide E64

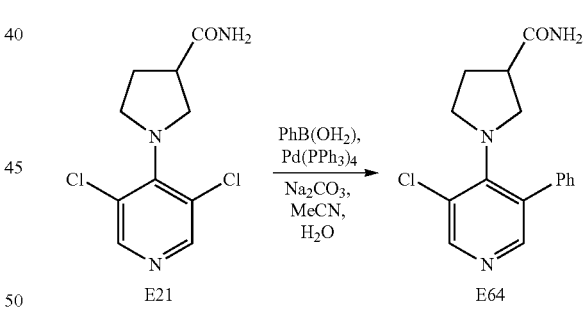

General procedure D was followed using (R,S)-1-(3,5-dichloropyridin-4-yl)pyrrolidine-3-carboxamide E21 (23 mg, 0.088 mmol), benzene boronic acid (13 mg, 0.11 mmol) and tetrakis(triphenylphosphine)palladium(0) (5 mg, 5 mol %), acetonitrile (1 mL) and 0.5 M sodium carbonate (0.25 mL, 0.12 mmol) for 30 min. The crude product was purified by preparative tlc on silica gel (CH$_2$Cl$_2$, MeOH, 10:1), to give a white solid (14 mg), followed by preparative hplc (H$_2$O, MeCN, gradient 90:10 to 10:90 over 30 min) to furnish the title compound as a white solid, LC-MS (ESI, 3.5 min) $R_t$ 1.32 min, m/z 302 (100%, [M+H]$^+$); m/z (ESI) $C_{16}H_{17}ClN_3O$ requires 302.1055 found [M+H]$^+$ 302.1047.

Example 65

1-(5-chloro-3,4'-bipyridin-4-yl)piperidine-4-carboxamide E65

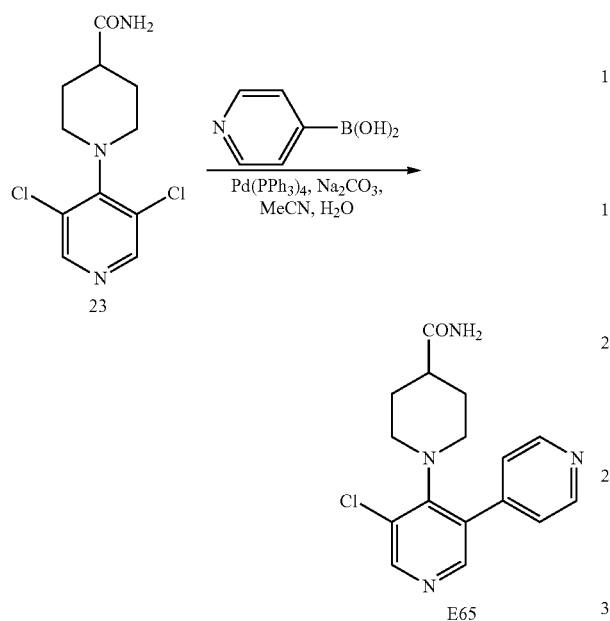

General procedure D was followed using 1-(3,5-dichloropyridin-4-yl)piperidine-4-carboxamide 23 (24 mg, 0.088 mmol), pyridin-4-yl boronic acid (12 mg, 0.11 mmol), tetrakis(triphenylphosphine)palladium(0) (5 mg, 5 mol %), acetonitrile (1 mL) and 0.5 M sodium carbonate (0.25 mL, 0.12 mmol) for 30 min. The crude product was purified by preparative tlc on silica gel ($CH_2Cl_2$, MeOH, 10:1) to furnish the title compound as a white solid (5 mg, 18%), LC-MS (ESI, 3.5 min) $R_t$ 1.10 min, m/z 317 (100%, [M+H]$^+$); m/z (ESI) $C_{16}H_{18}ClN_4O$ requires 317.1164 found [M+H]$^+$ 317.1160

Example 66

1-(3-cyclopropylpyridin-4-yl)piperidine-4-carboxamide E66

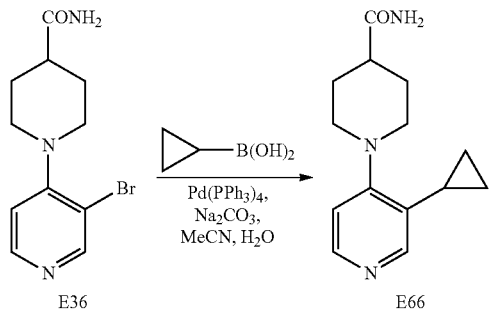

General procedure D was followed using 1-(3-bromopyridin-4-yl)piperidine-4-carboxamide E36 (25 mg, 0.088 mmol), cyclopropyl boronic acid (9.4 mg, 0.44 mmol), tetrakis (triphenylphosphine)palladium(0) (5 mg, 5 mol %), 0.5 M sodium carbonate (0.25 mL, 0.12 mmol) and acetonitrile (1 mL) for 50 min. The crude product was purified by preparative tlc on silica ($CH_2Cl_2$, MeOH 10:1) to furnish the title compound as a white solid (4 mg, 19%), LC-MS (ESI, 3.5 min) $R_t$ 0.97 min, m/z 246 (100%, [M+H]$^+$); m/z (ESI) $C_{14}H_{19}N_3O$ requires 246.1601 found [M+H]$^+$ 246.1596.

Example 67

1-(3-(1H-pyrazol-4-yl)pyridin-4-yl)piperidine-4-carboxamide E67

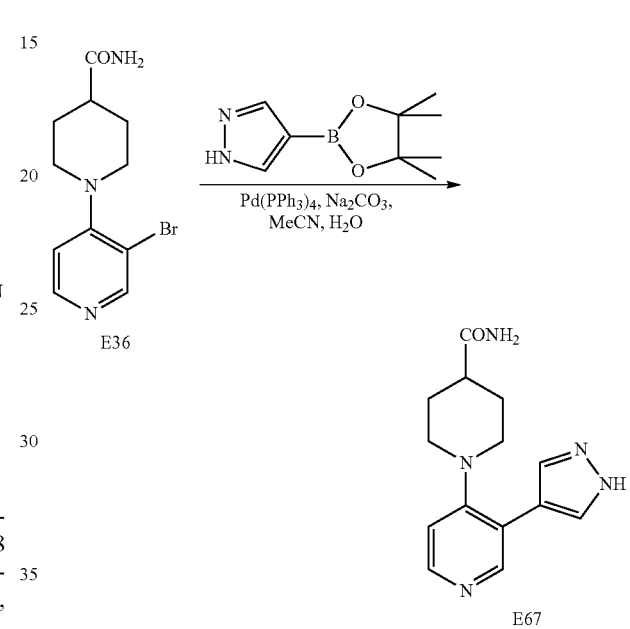

General procedure D was followed using 1-(3-bromopyridin-4-yl)piperidine-4-carboxamide E36 (25 mg, 0.088 mmol), 1H-pyrazol-4-boronic acid pinnacol ester (21 mg, 0.11 mmol), tetrakis(triphenylphosphine)palladium(0) (5 mg, 5 mol %), 0.5 M sodium carbonate (0.25 mL, 0.12 mmol) and acetonitrile (1 mL) for 50 min. The crude product was purified by preparative hplc ($H_2O$, MeCN, 95:5) to furnish the title compound as a white solid (11 mg, 46%), m/z (ESI) $C_{14}H_{18}N_5O$ requires 272.1506 found [M+H]$^+$ 272.1509.

Example 68

1-(3-phenylpyridin-4-yl)piperidine-4-carboxamide E68

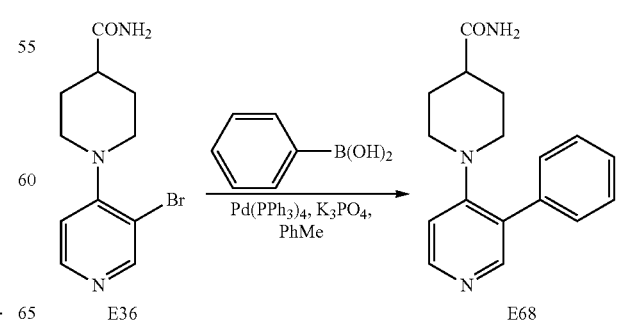

To a mixture of 1-(3-bromopyridin-4-yl)piperidine-4-carboxamide E36 (20 mg, 0.070 mmol), phenylboronic acid (17 mg, 0.14 mmol) and tetrakis (triphenylphosphine)palladium (0) (8 mg, 10 mol %) in toluene (1.5 mL) was added a potassium phosphate (45 mg, 0.21 mmol). The mixture was heated at 170° C. in a microwave reactor for 45 min, then poured into a saturated solution of sodium hydrogen carbonate (25 mL). The mixture was extracted with EtOAc (2×20 mL) and the combined organic extracts were washed with brine (25 mL), dried (MgSO$_4$) and the solvent was removed under reduced pressure. The crude product was purified by flash column chromatography on silica gel (CH$_2$Cl$_2$, MeOH, 95:5) to furnish the title compound as a white solid (5 mg, 25%), LC-MS (ESI, 3.5 min) R$_t$ 1.28 min, m/z 282 (100%, [M+H]$^+$), m/z (ESI) C$_{17}$H$_{20}$N$_3$O requires 282.1601 found [M+H]$^+$ 282.1597.

Example 69

(1-(3,5-dichloropyridin-4-yl)piperidin-4-yl)methanamine E69

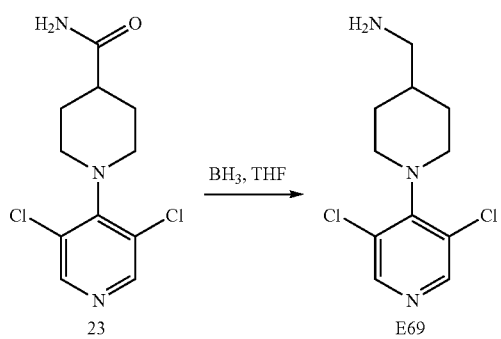 [SMILES: NC(=O)C1CCN(c2c(Cl)cncc2Cl)CC1 ; NCC1CCN(c2c(Cl)cncc2Cl)CC1]

To a solution of 1-(3,5-dichloropyridin-4-yl)piperidine-4-carboxamide 23 (30 mg, 0.11 mmol) in THF (2 mL), at 0° C., was added a 1M solution of borane THF complex in THF (11.1 mL, 1.1 mmol). The reaction was stirred for 1 hour before warming to r.t. and stirring for a further 18 hr. To the reaction was added 2M HCl (2 ml), the mixture diluted with water (20 ml) and extracted with EtOAc (2×20 mL) and the combined organic extracts were washed with brine (25 mL). The combined aqueous extracts were basified with saturated sodium hydrogen carbonate and then extracted with EtOAc (2×20 mL). The combined organic extracts were washed with brine (20 mL), dried (MgSO$_4$) and concentrated under reduced pressure to give a crude colourless oil (8 mg). The crude product was purified by flash column chromatography on silica gel (CH$_2$Cl$_2$, MeOH, 97:3 to CH$_2$Cl$_2$, 1 M methanolic NH$_3$, 9:1) to furnish the title compound, LC-MS (ESI, 3.5 min) R$_t$ 1.45 min, m/z 260 (91%, [M+H]$^+$).

Example 70

1-(3-chloro-5-(4-dimethylamino)pyridin-4-yl)piperidine-4-carboxamide E70

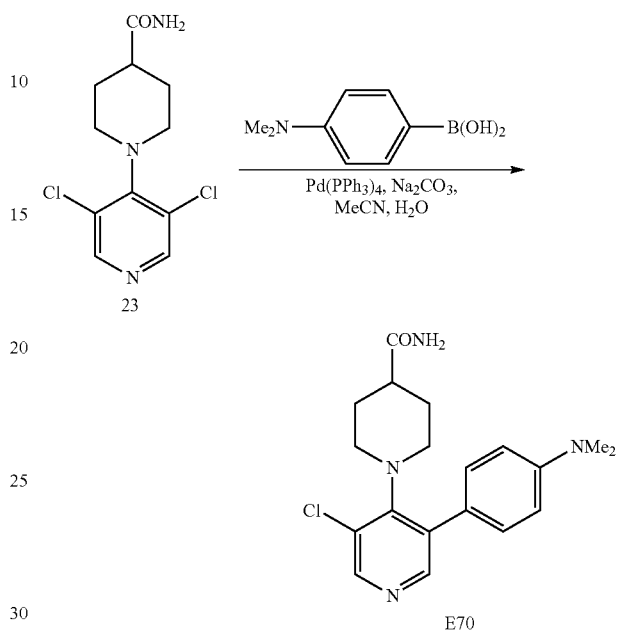

General procedure D was followed using 1-(3,5-dichloropyridin-4-yl)piperidine-4-carboxamide 23 (24 mg, 0.088 mmol), (4-dimethylamino)benzene boronic acid (17 mg, 0.11 mmol), tetrakis(triphenylphosphine)palladium(0) (5 mg, 5 mol %), acetonitrile (1 mL) and 0.5 M sodium carbonate (0.25 mL, 0.12 mmol) for 30 min. The crude product was purified by preparative tlc on silica gel (CH$_2$Cl$_2$, MeOH, 10:1) followed by preparative hplc (CH$_3$CN, H$_2$O, gradient 1:9 to 9:1) to furnish the title compound as a white solid (4 mg, 13%), LC-MS (ESI, 3.5 min) R$_t$ 1.54 min, m/z 359 (100%, [M+H]$^+$); m/z (ESI) C$_{19}$H$_{24}$Cl$_3$N$_4$O requires 359.1633 found [M+H]$^+$ 359.1633.

Example 71

1-(3-chloro-5-(1-methyl-1H-pyrazol-4-yl)pyridin-4-yl)piperidine-4-carboxamide E71

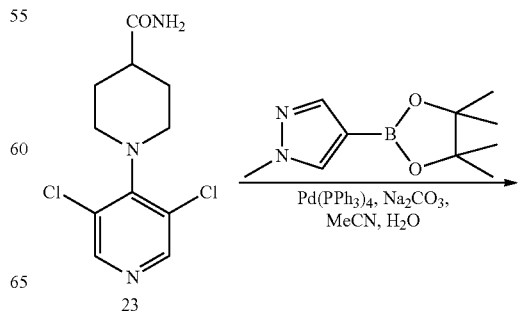

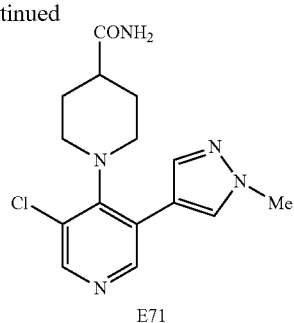

E71

General procedure D was followed using 1-(3,5-dichloro-pyridin-4-yl)piperidine-4-carboxamide 23 (24 mg, 0.088 mmol), 1-methyl-1H-pyrazole-4-boronic acid pinacol ester (20 mg, 0.11 mmol), tetrakis(triphenylphosphine)palladium (0) (5 mg, 5 mol %), acetonitrile (1 mL) and 0.5 M sodium carbonate (0.25 mL, 0.12 mmol) for 30 min. The crude product was purified by preparative tlc on silica gel ($CH_2Cl_2$, MeOH, 10:1) to furnish the title compound as a white solid (8 mg, 29%), LC-MS (ESI, 3.5 min) $R_t$ 1.20 min, m/z 320 (100%, $[M+H]^+$); m/z (ESI) $C_{15}H_{19}ClN_5O$ requires 320.1273 found $[M+H]^+$ 320.1272.

Example 72

1-(5-chloro-6'-(dimethylamino)-3,3'-bipyridin-4-yl)piperidine-4-carboxamide E72

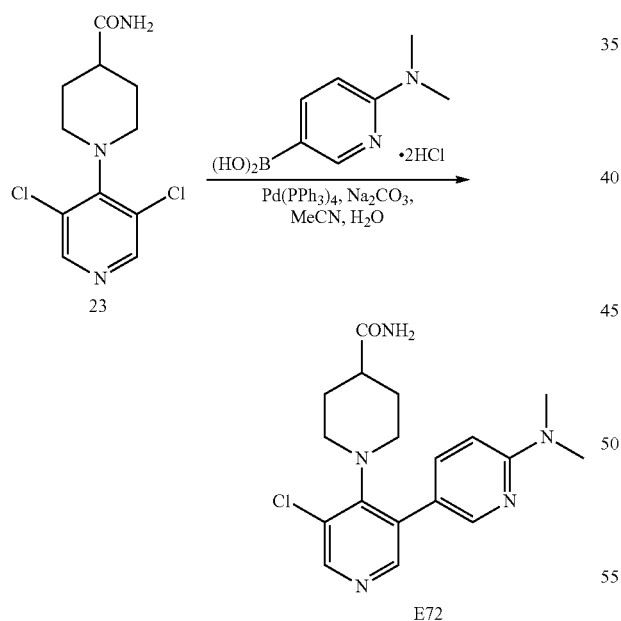

E72

General procedure E was followed using 1-(3,5-dichloro-pyridin-4-yl)piperidine-4-carboxamide 23 (50 mg, 0.18 mmol), 2-(N,N-dimethylamino)pyridine-5-boronic acid 2HCl salt (55 mg, 0.23 mmol), tetrakis(triphenylphosphine)palladium(0) (11 mg, 5 mol %), acetonitrile (2 mL) and 0.5 M sodium carbonate (1.3 mL, 0.66 mmol). The crude product was purified by flash column chromatography on silica gel ($CH_2Cl_2$, EtOH, 96:4-82:18, biotage 25+S) followed by preparative tlc ($CH_2Cl_2$, MeOH, 9:1) to furnish the title compound as an off white solid (6 mg, 9%), LC-MS (ESI, 4 min) $R_t$ 1.28 min, m/z 360 (100%, $[M+H]^+$); m/z (ESI) $C_{17}H_{22}N_5OCl$ requires 359.1513, found $[M+H]^+$ 359.1511.

Example 73

N-(1-(3,5-dichloropyridin-4-yl)piperidin-4-yl)acetamide E73

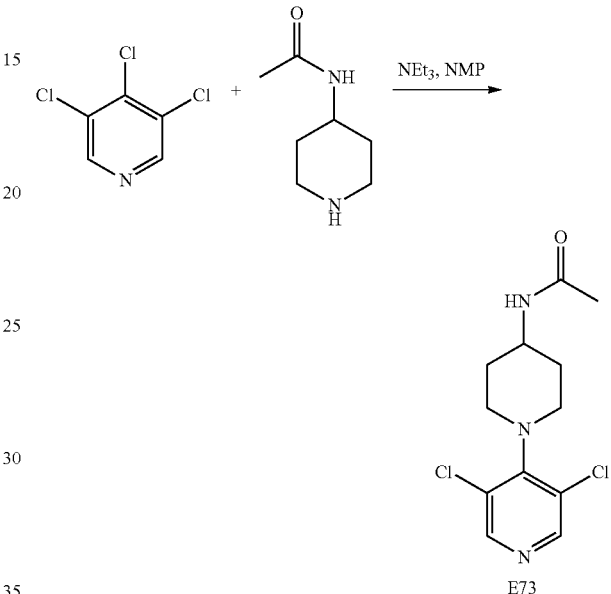

E73

General procedure C was followed using 3,4,5-trichloropyridine (50 mg, 0.27 mmol), 4-acetamidopiperidine (43 mg, 0.30 mmol), triethylamine (76 µL, 0.54 mmol) and NMP (1.5 mL). The crude product was purified by flash column chromatography on silica gel (hexane, EtOAc, MeOH, 1:1:0.05) to furnish the title compound as white solid (7 mg, 9%), LC-MS (ESI, 3.5 min) $R_t$ 2.25 min; m/z (ESI) $C_{12}H_{16}Cl_2N_3O$ requires 288.0665 found $[M+H]^+$ 288.0664; HPLC $R_t$ 5.98 min, 100%.

Example 74

1-(3-chloro-5-(4-methoxyphenyl)pyridin-4-yl)pyrrolidine-3-carboxamide E74

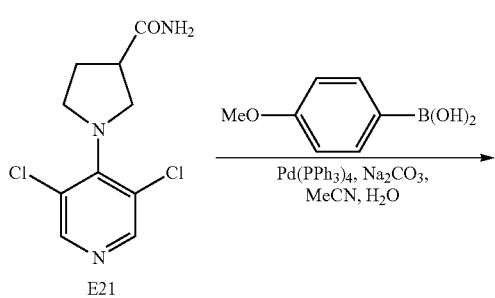

E21

87
-continued

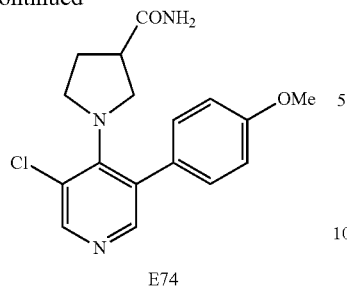

E74

General procedure D was followed using 1-(3,5-dichloropyridin-4-yl)pyrrolidine-3-carboxamide E21 (23 mg, 0.088 mmol), 4-methoxybenzene boronic acid (13 mg, 0.11 mmol), tetrakis(triphenylphosphine)palladium(0) (5 mg, 5 mol %), acetonitrile (1 mL) and 0.5 M sodium carbonate (0.25 mL, 0.12 mmol) for 30 min. The crude product was purified by preparative tlc on silica gel ($CH_2Cl_2$, MeOH, 10:1) to give impure title compound as a white solid (15 mg). Further purification by preparative hplc ($H_2O$, MeCN, gradient 90:10 to 10:90 over 30 min) furnished the title compound as a white solid, LC-MS (ESI, 3.5 min) $R_t$ 1.40 min, m/z 332 (100%, [M+H]$^+$); m/z (ESI, 3.5 min) $C_{17}H_{18}ClN_3NaO_2$ requires 354.0980 found [M+Na]$^+$ 354.0980

Example 75

1-(5-chloro-3,3'-bipyridin-4-yl)piperidine-4-carboxamide E75

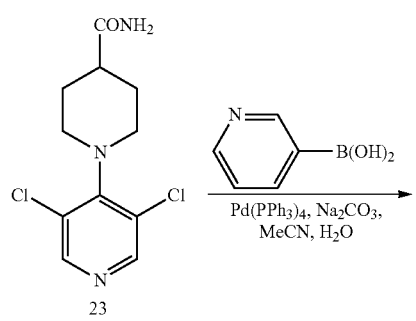

E75

General procedure D was followed using 1-(3,5-dichloropyridin-4-yl)piperidine-4-carboxamide 23 (24 mg, 0.088 mmol), pyridin-3-yl boronic acid (12 mg, 0.11 mmol), tetrakis(triphenylphosphine)palladium(0) (5 mg, 5 mol %), acetonitrile (1 mL) and 0.5 M sodium carbonate (0.25 mL, 0.12 mmol) for 30 min. The crude product was purified by preparative tlc on silica gel ($CH_2Cl_2$, MeOH, 10:1) to furnish the title compound as a white solid (7 mg, 25%), LC-MS

88

(ESI, 3.5 min) $R_t$ 1.06 min, m/z 317 (100%, [M+H]$^+$); m/z (ESI) $C_{16}H_{18}ClN_4O$ requires 317.1164 found [M+H]$^+$ 317.1161.

Example 76

1-(3-chloro-5-(2-methoxypyrimidin-5-yl)pyridin-4-yl)piperidine-4-carboxamide E76

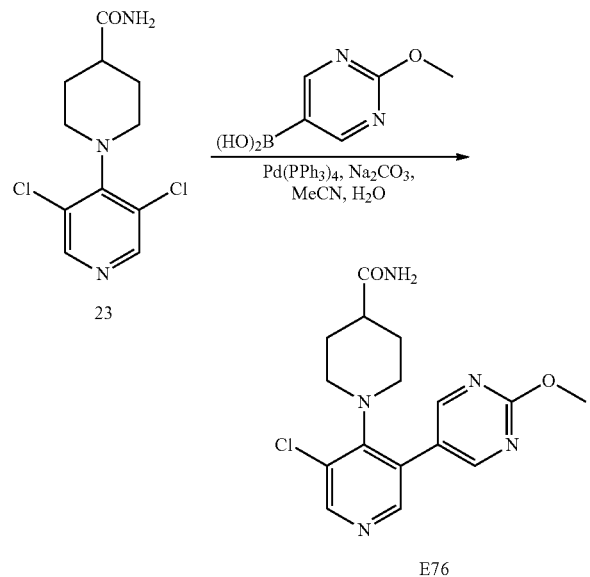

E76

General procedure E was followed using 1-(3,5-dichloropyridin-4-yl)piperidine-4-carboxamide 23 (75 mg, 0.27 mmol), 2-methoxypyrimidine-5-boronic acid (53 mg, 0.34 mmol), tetrakis(triphenylphosphine)palladium(0) (16 mg, 5 mol %), acetonitrile (3 mL) and 0.5 M sodium carbonate (0.77 mL, 0.38 mmol). The crude product was purified by flash column chromatography on silica gel ($CH_2Cl_2$, EtOH, 96:4-82:18, biotage 25+S) to furnish the title compound as an off white solid (20 mg, 21%), along with recovered 1-(3,5-dichloropyridin-4-yl)piperidine-4-carboxamide as a white solid (32 mg, 43% RSM), LC-MS (ESI, 4 min) $R_t$ 1.76 min, m/z 348 (100%, [M+H]$^+$); m/z (ESI) $C_{16}H_{18}N_5O_2Cl$ requires 347.1149, found [M+H]$^+$ 347.1147.

Example 77

1-(3-chloro-5-(3,4-difluorophenyl)pyridin-4-yl)piperidine-4-carboxamide E77

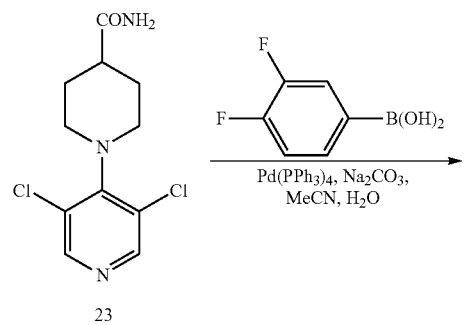

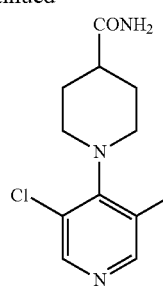
E77

General procedure D was followed using 1-(3,5-dichloropyridin-4-yl)piperidine-4-carboxamide 23 (24 mg, 0.088 mmol), 3,4-difluorobenzene boronic acid (17 mg, 0.11 mmol), tetrakis(triphenylphosphine)palladium(0) (5 mg, 5 mol %), acetonitrile (1 mL) and 0.5 M sodium carbonate (0.25 mL, 0.12 mmol) for 30 min. The crude product was purified by preparative tlc on silica gel ($CH_2Cl_2$, MeOH, 10:1), to give impure title compound as a white solid (16 mg) followed by preparative hplc ($CH_3CN$, $H_2O$, gradient 1:9 to 9:1) to furnish the title compound as a white solid, LC-MS (ESI, 3.5 min) $R_t$ 1.91 min, m/z 352 (100%, $[M+H]^+$); m/z (ESI) $C_{17}H_{16}ClF_2N_3O$ requires 352.1023 found $[M+H]^+$ 352.1017.

Example 78

1-(3-chloro-5-(1H-pyrazol-4-yl)pyridin-4-yl)piperidine-4-carboxamide E78

General procedure D was followed using 1-(3,5-dichloropyridin-4-yl)piperidine-4-carboxamide 23 (24 mg, 0.088 mmol), 1H-pyrazole-4-boronic acid pinacol ester (12 mg, 0.11 mmol), tetrakis(triphenylphosphine)palladium(0) (5 mg, 5 mol %), acetonitrile (1 mL) and 0.5 M sodium carbonate (0.25 mL, 0.12 mmol) for 30 min. The crude product was purified by preparative tlc on silica gel ($CH_2Cl_2$, MeOH, 10:1) to furnish the title compound as a white solid (18 mg, 67%), LC-MS (ESI, 3.5 min) $R_t$ 1.06 min, m/z 306 (100%, $[M+H]^+$); m/z (ESI) $C_{14}H_{17}ClN_5O$ requires 306.1116 found $[M+H]^+$ 306.1114.

Example 79

1-(3-chloro-5-(thiophen-2-yl)pyridin-4-yl)piperidine-4-carboxamide E79

General procedure E was followed using 1-(3,5-dichloropyridin-4-yl)piperidine-4-carboxamide 23 (75 mg, 0.27 mmol), 2-thiophene boronic acid (44 mg, 0.34 mmol), tetrakis(triphenylphosphine)palladium(0) (16 mg, 0.014 mmol), acetonitrile (3 mL) and 0.5 M sodium carbonate (0.77 mL, 0.38 mmol). The crude product was purified by flash column chromatography on silica gel ($CH_2Cl_2$, EtOH, 96:4-80:20, biotage 25+S) to yield the a mixture of starting material and product (50 mg, 2:5), along with dehalogenated monochloro starting material (7 mg, 11%). The product/starting material mixture was further purified by preparative hplc ($CH_3CN$, $H_2O$, gradient 1:9 to 9:1, 15 min) to furnish the title compound (9 mg, 10%) as a clear colourless oil, along with recovered 1-(3,5-dichloropyridin-4-yl)piperidine-4-carboxamide (30 mg, 40%) as a white solid, LC-MS (ESI, 4 min) $R_t$ 2.31 min, m/z 322 (100%, $[M+H]^+$); m/z (ESI) $C_{15}H_{16}N_3OSCl$ requires 321.0703, found $[M+H]^+$ 321.0700.

Example 80

1-(3-bromo-5-chloropyridin-4-yl)piperidine-4-carboxamide E80

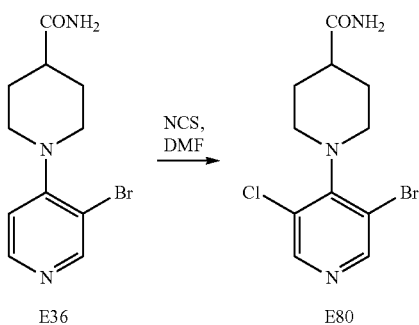 [SMILES: NC(=O)C1CCN(c2ccncc2Br)CC1 ; NC(=O)C1CCN(c2c(Cl)cncc2Br)CC1]

To a solution of 1-(3-bromopyridin-4-yl)piperidine-4-carboxamide E36 (100 mg, 0.35 mmol) in DMF (7.00 mL) was added N-chlorosuccinimide (94 mg, 0.70 mmol). The reaction was heated to 80° C. and stirred for 8 hours before partitioning between EtOAc and water (100 ml each), the separated organic layer was washed with water (2×75 ml), brine (20 mL), dried (MgSO$_4$) and concentrated under reduced pressure to give a crude clear pale yellow oil (82 mg). The crude product was purified by flash column chromatography on silica gel (CH$_2$Cl$_2$, EtOH, 98:2-84:16, biotage 25+S) followed by flash column chromatography on silica gel (CH$_2$Cl$_2$, EtOH, 96:4-82:18, biotage 14+M) to give a mixture of title compound and 1-(3,5-dichloropyridin-4-yl)piperidine-4-carboxamide by-product as a white solid (20 mg). The mixture was further purified by preparative hplc (MeOH, H$_2$O, 9:20, 25 min) to furnish the title compound as a white solid, LC-MS (ESI, 4 min) R$_t$ 2.46 min, m/z 320 (100%, [M+H]$^+$); m/z (ESI) C$_{11}$H$_{13}$N$_3$OClBr requires 316.9931, found [M+H]$^+$ 318.0003.

Example 81

1-(3-(4-trifluoromethylphenyl)pyridin-4-yl)piperidine-4-carboxamide E81

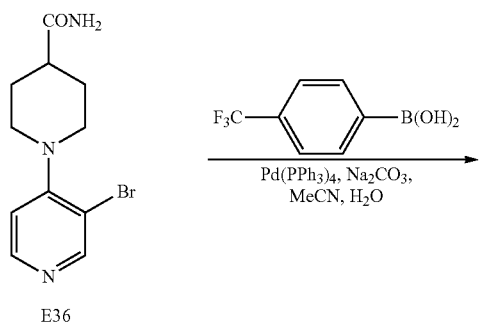

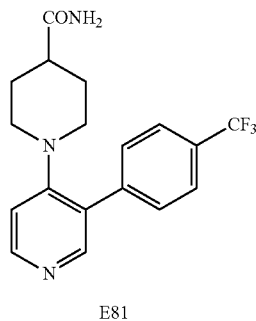

General procedure D was followed using 1-(3-bromopyridin-4-yl)piperidine-4-carboxamide E36 (25 mg, 0.088 mmol), 4-trifluoromethyphenyllboronic acid (20 mg, 0.11 mmol), tetrakis (triphenylphosphine)palladium(0) (5 mg, 5 mol %), 0.5 M sodium carbonate (0.25 mL, 0.12 mmol) and acetonitrile (1 mL) for 50 min. The crude product was purified by preparative tlc on silica gel (CH$_2$Cl$_2$, MeOH, 10:1) to furnish the title compound as a white solid (28 mg, 91%), LC-MS (ESI, 3.5 min) R$_t$ 1.51 min, m/z 350 (100%, [M+H]$^+$); m/z (ESI) C$_{18}$H$_{19}$F$_3$N$_3$O requires 350.1475 found [M+H]$^+$ 350.1478.

Examples 82 and 83

1-(3-bromo-5-o-tolylpyridin-4-yl)piperidine-4-carboxamide E82 and 1-(3,5-dio-tolylpyridin-4-yl)piperidine-4-carboxamide E83

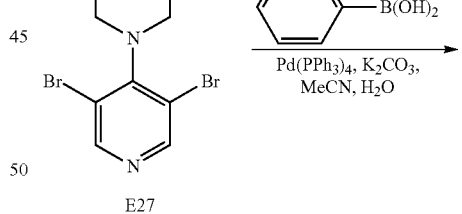

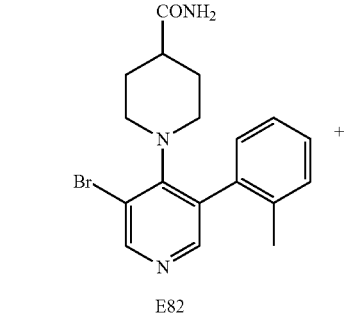

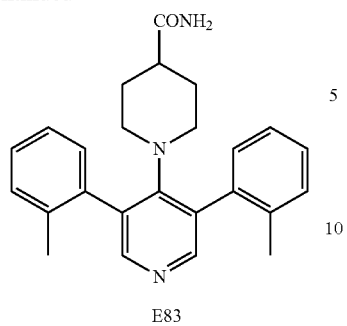

E83

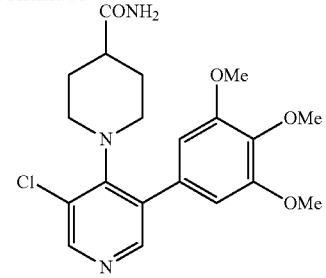

E84

To a solution of 1-(3,5-dibromopyridin-4-yl)piperidine-4-carboxamide E27 (50 mg, 0.14 mmol), o-tolylboronic acid (77 mg, 0.56 mmol) and potassium phosphate (0.20 g, 0.96 mmol) in toluene (4 mL) was added tetrakis(triphenylphosphine)palladium(0) (18 mg, 10 mol %). The mixture was heated at 170° C. in a microwave reactor for 45 min, then poured into a saturated solution of sodium hydrogen carbonate (25 mL). The mixture was extracted with EtOAc (2×25 mL) and the combined organic extracts were washed with water (25 mL), brine (25 mL), dried (MgSO$_4$) and the solvent was removed under reduced pressure. The crude product was purified by flash column chromatography on silica gel (CH$_2$Cl$_2$, MeOH, 98:2) to yield impure title compound as a white solid (23 mg). Further purification by preparative hplc furnished both title compounds as white solids. 1-(3-bromo-5-o-tolylpyridin-4-yl)piperidine-4-carboxamide E82: (13 mg, 24%), LC-MS (ESI, 3.5 min) R$_t$ 1.85 min, m/z 376 (100%, [M+H]$^+$); m/z (ESI) C$_{25}$H$_{28}$N$_3$O requires 374.0863 found [M+H]$^+$ 374.0860.

1-(3,5-dio-tolylpyridin-4-yl)piperidine-4-carboxamide E83: (3.3 mg, 6%), LC-MS (ESI, 3.5 min) R$_t$ 1.66 min, m/z 386 (100%, [M+H]$^+$); m/z (ESI) C$_{18}$H$_{21}$BrN$_3$O requires 386.2227 found [M+H]$^+$ 386.2225.

Example 84

1-(3-chloro-5-(3,4,5-trimethoxyphenyl)pyridin-4-yl)piperidine-4-carboxamide E84

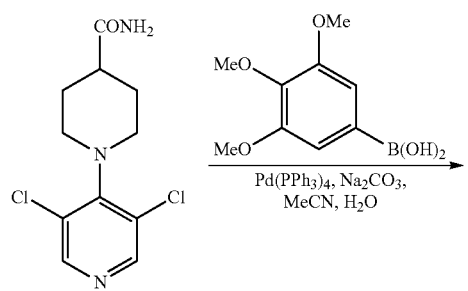

23

General procedure D was followed using 1-(3,5-dichloropyridin-4-yl)piperidine-4-carboxamide 23 (24 mg, 0.088 mmol), 3,4,5-trimethoxyphenyllboronic acid (22 mg, 0.11 mmol), tetrakis(triphenylphosphine)palladium(0) (5 mg, 5 mol %), 0.5 M sodium carbonate (0.25 mL, 0.12 mmol) and acetonitrile (1 mL) for 30 min. The crude product was purified by preparative tlc on silica gel (CH$_2$Cl$_2$, MeOH, 10:1) to give impure title compound as a colourless oil (17 mg). Further purification by preparative hplc furnished the title compound, LC-MS (ESI, 3.5 min) R$_t$ 1.71 min, m/z 406 (100%, [M+H]$^+$); m/z (ESI) C$_{20}$H$_{25}$ClN$_3$O$_4$ requires 406.1528 found [M+H]$^+$ 406.1526.

Example 85

1-(5-(4-methoxyphenyl)pyrimidin-4-yl)piperidine-4-carboxamide E85

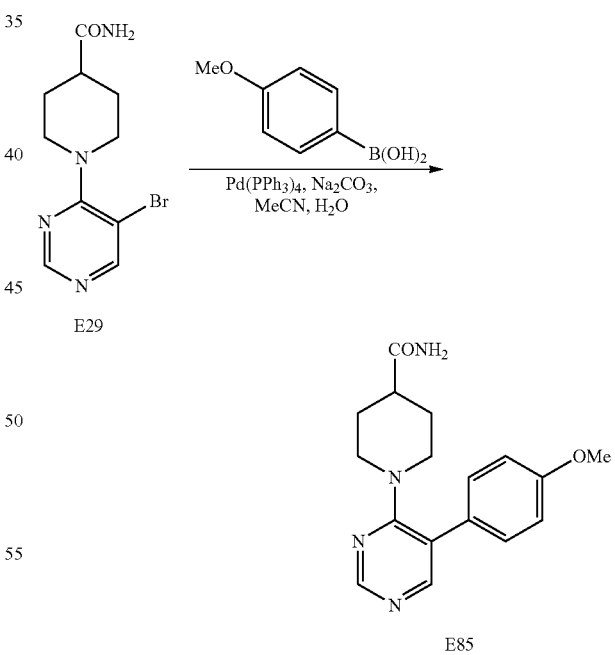

General procedure D was followed using 1-(5-bromopyrimidin-4-yl)piperidine-4-carboxamide E29 (11 mg, 0.039 mmol), 4-methoxyphenyllboronic acid (7 mg, 0.046 mmol), tetrakis(triphenylphosphine)palladium(0) (2.5 mg, 5 mol %), 0.5 M sodium carbonate (0.11 mL, 0.054 mmol) and acetonitrile (1 mL) for 30 min. The crude product was purified by preparative tlc on silica gel (CH$_2$Cl$_2$, MeOH, 10:1) to furnish the title compound as a white solid (5 mg, 41%), LC-MS (ESI, 3.5 min) $R_t$ 1.33 min, m/z 312 (100%, [M+H]$^+$)

Example 86

1-(3-chloro-5-phenylpyridin-4-yl)piperidine-4-carbonitrile E86

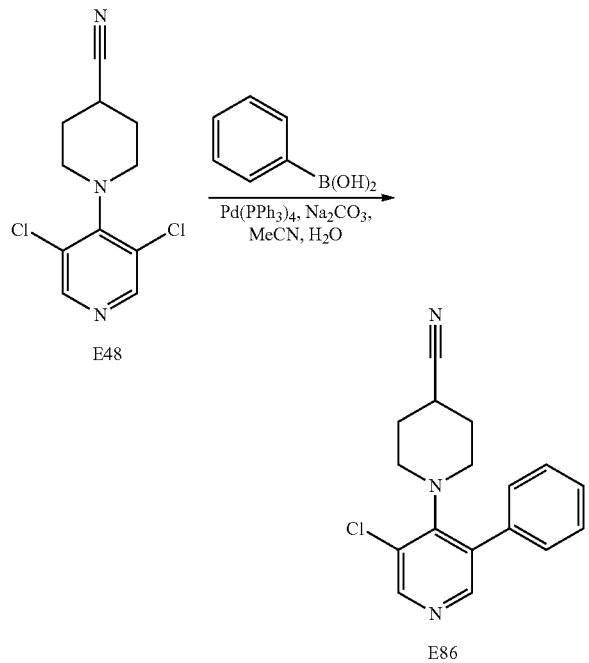

General procedure D was followed using 1-(3,5-dichloropyridin-4-yl)piperidine-4-carbonitrile E48 (100 mg, 0.39 mmol), phenylboronic acid (57 mg, 0.47 mmol), tetrakis(triphenylphosphine)palladium(0) (22 mg, 5 mol %), 0.5 M sodium carbonate (1.1 mL, 0.55 mmol) and acetonitrile (3.5 mL) for 45 min. The crude product was purified by preparative hplc (H$_2$O, MeCN, 90:10-10:90, 30 min) to furnish the title compound (25 mg, 22%), LC-MS (ESI, 3.5 min) $R_t$ 2.24 min, m/z 298 (100%, [M+H]$^+$).

Example 87

1-(3-chloro-5-phenylpyridin-4-yl)piperidine-4-carboxylic acid E87

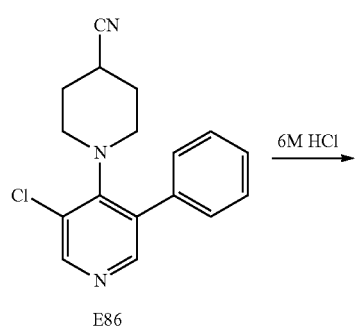

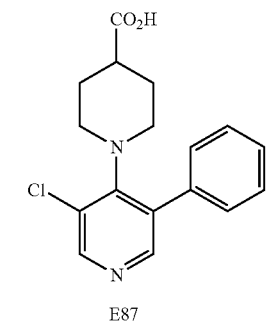

A solution of 1-(3-chloro-5-phenylpyridin-4-yl)piperidine-4-carbonitrile E86 (16 mg, 0.054 mmol) was heated in 6M hydrochloric acid (1 mL) for 2 hours at 100° C. The reaction was concentrated under reduced pressure and purified on an SCX-2 cartridge (MeOH, followed by 0.5 M NH$_3$ in MeOH). The crude product was purified by preparative tlc on silica gel (CH$_2$Cl$_2$, MeOH, 10:1) to furnish the title compound (5 mg, 30%), LC-MS (ESI, 4 min) $R_t$ 2.13 min, m/z 317 (100%, M+H]$^+$).

Example 88

1-(3,5-dichloropyridin-4-yl)piperidine-4-carboxylic acid E88

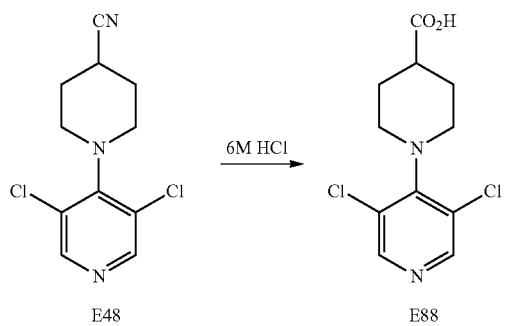 [SMILES: N#CC1CCN(c2c(Cl)cncc2Cl)CC1 ; O=C(O)C1CCN(c2c(Cl)cncc2Cl)CC1]

A solution of 1-(3,5-dichloropyridin-4-yl)piperidine-4-carbonitrile E48 (25 mg, 0.097 mmol) was heated in 6M hydrochloric acid (2 mL) for 3 hours at 100° C. The reaction was concentrated under reduced pressure and purified on an SCX-2 cartridge (MeOH, followed by 0.5 M NH$_3$ in MeOH). The crude product (16 mg) was purified by preparative tlc on silica gel (CH$_2$Cl$_2$, MeOH, 10:1) to furnish the title compound, LC-MS (ESI, 4 min) $R_t$ 2.83 min, m/z 275 (100%, M+H]$^+$); m/z (ESI) C$_{11}$H$_{12}$Cl$_2$N$_2$O$_2$ requires 275.0349 found [M+H]$^+$ 275.0349.

Example 89 benzyl 2-(1-(3-chloro-5-phenylpyridin-4-yl)piperidine-4-carboxamido) ethylcarbamate E89

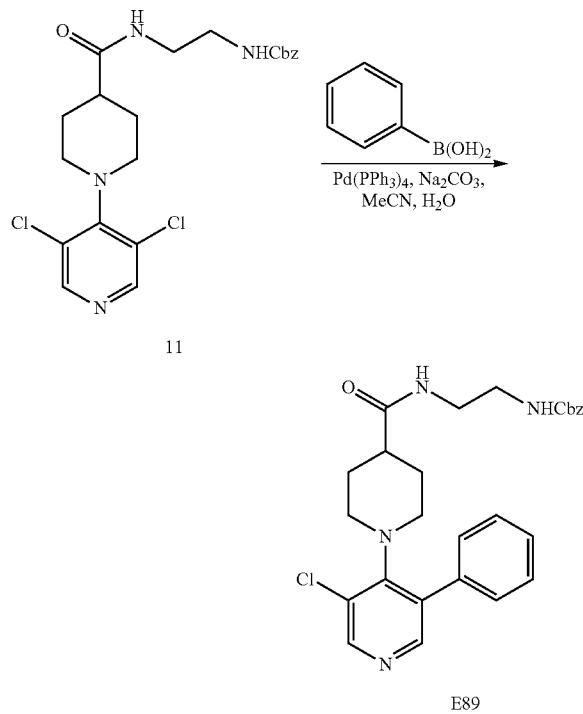

General procedure D was followed using benzyl-2-(1-(3,5-dichloropyridin-4-yl)piperidine-4-carboxamido)ethyl carbamate 11 (105 mg, 0.23 mmol), phenyllboronic acid (34 mg, 0.28 mmol), tetrakis(triphenylphosphine)palladium(0) (13 mg, 5 mol %), 0.5 M sodium carbonate (0.65 mL, 0.33 mmol) and acetonitrile (2.5 mL) for 45 min. The crude product was purified by preparative tlc on silica gel (CH$_2$Cl$_2$, MeOH, 10:1) to give impure title compound (32 mg). Further purification by preparative hplc furnished the title compound, LC-MS (ESI, 3.5 min) R$_t$ 2.43 min, m/z 494 (100%, [M+H]$^+$).

Example 90

N-(2-aminoethyl)-1-(3-chloro-5-phenylpyridin-4-yl)piperidine-4-carboxamide E90

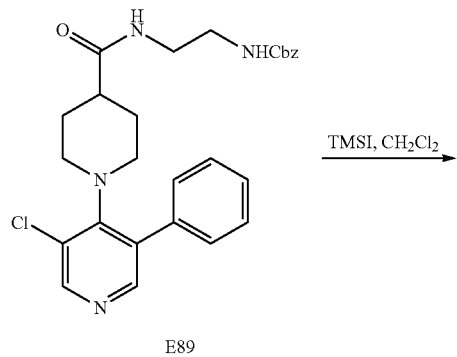

To a solution of benzyl-2-(1-(3-chloro-5-phenylpyridin-4-yl)piperidine-4-carboxamido) ethylcarbamate E89 (39 mg, 0.079 mmol) in CH$_2$Cl$_2$ (2 mL), at 0° C., was added TMSI (34 µL, 0.24 mmol). The reaction was warmed to r.t. over 3 hours and then concentrated under reduced pressure and purified on an SCX-2 cartridge (MeOH, followed by 0.5 M NH$_3$ in MeOH) to furnish the title compound (23 mg, 81%), LC-MS (ESI, 3.5 min) R$_t$ 1.33 min, m/z 359 (40%, [M+H]$^+$); m/z (ESI) C$_{19}$H$_{24}$ClN$_4$O requires 359.1623 found [M+H]$^+$ 359.1633.

Example 91

1-(3,5-bis(4-methoxyphenyl)pyridin-4-yl)piperidine-4-carboxamide E91

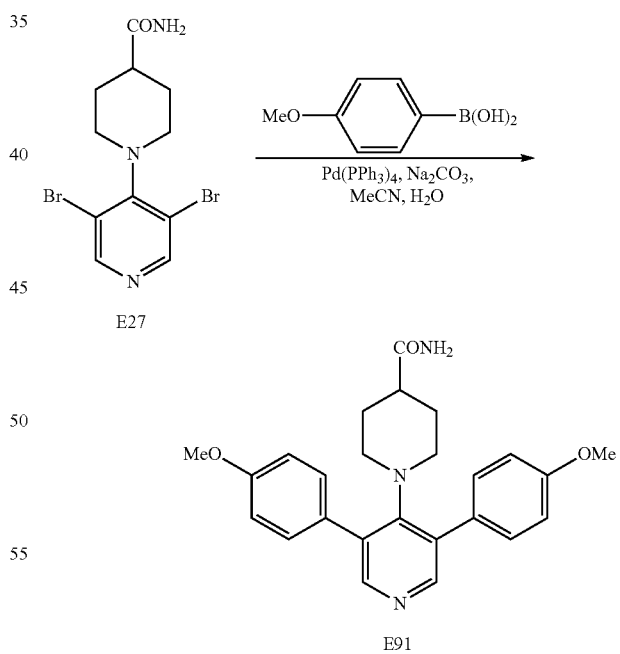

General procedure D was followed using 1-(3,5-dibromopyridin-4-yl)piperidine-4-carboxamide E27 (50 mg, 0.14 mmol), 4-methoxyphenylboronic acid (25 mg, 0.15 mmol), tetrakis(triphenylphosphine)palladium(0) (8 mg, 5 mol %), acetonitrile (1.4 mL) and 0.5 M sodium carbonate (0.27 mL, 0.16 mmol) for 30 min. The crude product was purified by flash column chromatography on silica gel (CH$_2$Cl$_2$, MeOH, 98:2) to furnish the title compound as a white solid (39 mg), LC-MS (ESI, 3.5 min) R$_t$ 1.68 min, m/z 418 (100%, [M+H]$^+$).

Example 92

Activity Assay

Inhibitory activity of the Wnt pathway was assessed using a luciferase reporter cell based assay. A luciferase reporter cell line was developed in HEK293 cells, which contained an estrogen receptor-DSH (ER-DSH) construct and a TCF-luciferase-IRES-GFP construct.

A high-throughput assay was performed by inducing TCF-dependent transcription in the ER-DSH HEK293 cell line by the addition of estrogen (2 μM) resulting in at least a 14-fold increase in reporter activity measured at 24 hours.

Subsequent primary and secondary deconvolution assays were used to evaluate the compounds. Firstly, compounds were tested for inhibitory activity in HEK293 cells transiently transfected with a TCF-luciferase reporter plasmid alone or in combination with an ER-inducible DSH plasmid. Induction of the pathway was brought about with either estradiol or BIO. A TK-*Renilla* luciferase plasmid was used as a co-transfected control to identify compounds with specificity for Wnt signalling compared to general transcription.

Particular compounds of the invention possess and IC50 in the above-mentioned luciferase assay of less than 10 μM. Preferred compounds have an IC50 of less than 1 μM and most preferred compounds have an IC50 of less than 0.5 μM.

Illustrative activity values for particular compounds of the invention in the Luciferase reporter assay described above are shown in Table A below:

TABLE A

| Example/Compound Number | IC50 in Luciferase reporter assay (ER-DSH HEK293 cells) assay described in Example 92 (μM) |
|---|---|
| E1 | 12.6 |
| E2 | 30.0 |
| E4 | 0.17 |
| E9 | 12.1 |
| E12 | 22.9 |
| E13 | 7.0 |
| E21 | 0.76 |
| E27 | 0.21 |
| E29 | 16.2 |
| E33 | 5.0 |
| E35 | 7.66 |
| E37 | 1.64 |
| E43 | 0.032 |
| E47 | 0.44 |
| E50 | 0.11 |
| E59 | 3.43 |
| E60 | 0.033 |
| E65 | 0.44 |
| E68 | 1.15 |
| E74 | 0.26 |
| E85 | 1.58 |
| E86 | 0.09 |
| E87 | 0.74 |

Compounds were then further tested in similar assays in which the pathway was induced by constitutive expression of DN-LRP (a component of the Wnt receptor), Ax-2 (a dominant negative form of axin), DN-β-catenin (a stabilised form of (β-catenin) and VP16-TCF (a TCF transcription factor active in the absence of (β-catenin).

The growth inhibitory activity of compounds was also determined against a small panel of human colorectal cell lines (HCT116, HT29, and SW480).

Certain compounds were found to have a GI$_{50}$ against the HT29 cell line of less than 100 μM and an IC$_{50}$ against the Luciferase reporter vector of less than 100 μM.

The invention claimed is:

1. A compound of the formula (I):

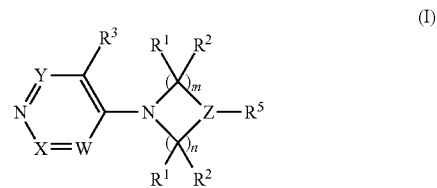

wherein
W, X and Y are each independently CH, C(R$^4$) or N;
Z is C(R$^6$);
R$^1$ and R$^2$ are each independently hydrogen or C$_{1-6}$ alkyl; or R$^1$ and R$^2$ taken together with the carbon atom to which they are attached may form a 5- or 6-membered carbocycle or heterocycle, either of which is optionally substituted with 1, 2, 3, 4 or 5 R$^a$;
R$^3$ and R$^4$ are each independently halo or a group selected from C$_{1-6}$ alkyl, C$_{1-6}$ alkoxy, carbocyclyl and heterocyclyl, any of which is optionally substituted with 1, 2, 3, 4 or 5 R$^a$;
wherein R$^5$ and R$^6$ taken together with the carbon atom to which they are attached form a 5- or 6-membered heterocycle containing a ring amide group, wherein the heterocycle is unsubstituted;
each R$^a$ is independently selected from halogen, trifluoromethyl, cyano, oxo, nitro, —OR$^b$, —C(O)R$^b$, —C(O)OR$^b$, —OC(O)R$^b$, —S(O)$_l$R$^b$, —N(R$^b$)R$^c$, —N(R$^b$)C(O)R$^c$, —C(O)N(R$^b$)R$^c$, —S(O)$_l$N(R$^b$)R$^c$ and R$^d$;
R$^b$ and R$^c$ are each independently hydrogen or R$^d$;
R$^d$ is selected from hydrocarbyl (e.g. C$_{1-6}$alkyl), carbocyclyl, carbocyclyl-C$_{1-6}$alkyl, and heterocyclyl, each of which is optionally substituted with 1, 2, 3, 4 or 5 substituents independently selected from halogen, cyano, amino, hydroxy, C$_{1-6}$ alkyl, C$_{1-6}$ alkoxy;
l is 0, 1 or 2; and
m and n are each independently 1, 2 or 3;
or a pharmaceutically acceptable salt or N-oxide thereof.

2. A compound according to claim 1, which is of the formula (II):

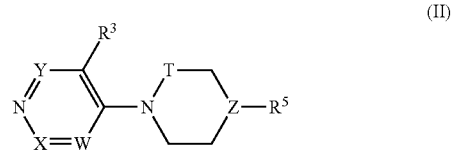

wherein T is a bond or —CH$_2$—.

3. A compound according to claim 1, wherein X and Y are each CH.

4. A compound according to claim 1, wherein W is C(R$^4$) or N.

5. A compound according to claim 4, wherein R$^4$ is halo.

6. A compound according to claim 1, wherein R$^3$ is halo or a group selected from C$_{1-6}$ alkyl, aryl or heteroaryl, any of which is optionally substituted with 1, 2, 3, 4 or 5 R$^a$.

7. A compound according to claim 6, wherein $R^3$ is halo or a group selected from $C_{1-6}$ alkyl, phenyl, pyrazolyl, triazolyl, oxazolyl, isoxazolyl, pyridinyl, pyridazinyl, pyrimidinyl and thiophenyl, any of which is optionally substituted with 1, 2, 3, 4 or 5 $R^a$.

8. A compound according to claim 1, wherein $R^5$ and $R^6$ taken together with the carbon atom to which they are attached form oxazolidone or 2-oxopyrrolidine.

9. A compound which is selected from any one of the following:
- 8-(3,5-dichloropyridin-4-yl)-2,8-diazaspiro[4.5]decan-1-one;
- 8-(3-chloro-5-phenylpyridin-4-yl)-2,8-diazaspiro[4.5]decan-1-one;

or a pharmaceutically acceptable salt or N-oxide thereof.

10. A compound of the formula (I) as defined in claim 1, or a pharmaceutically acceptable salt or N-oxide thereof, with the proviso that $R^4$ is not an optionally substituted imidazolyl group.

11. A pharmaceutical formulation comprising a compound of claim 1 or a pharmaceutically acceptable salt or N-oxide thereof and a pharmaceutically acceptable carrier or excipient.

* * * * *